(12) United States Patent
Kehler et al.

(10) Patent No.: US 10,150,771 B2
(45) Date of Patent: Dec. 11, 2018

(54) TRIAZOLOPYRAZINONES AS PDE1 INHIBITORS

(71) Applicant: H. Lundbeck A/S, Valby (DK)

(72) Inventors: Jan Kehler, Lyngby (DK); Lars Kyhn Rasmussen, Vanløse (DK); Mikkel Jessing, København Ø (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 15/517,348

(22) PCT Filed: Oct. 9, 2015

(86) PCT No.: PCT/EP2015/073417
§ 371 (c)(1),
(2) Date: Apr. 6, 2017

(87) PCT Pub. No.: WO2016/055618
PCT Pub. Date: Apr. 14, 2016

(65) Prior Publication Data
US 2017/0298072 A1    Oct. 19, 2017

(30) Foreign Application Priority Data
Oct. 10, 2014    (DK) .................................. 2014 00582

(51) Int. Cl.
*C07D 487/04*    (2006.01)
(52) U.S. Cl.
CPC .................................. *C07D 487/04* (2013.01)
(58) Field of Classification Search
CPC .................................................. C07D 487/04
See application file for complete search history.

(56) References Cited

U.S. PATENT DOCUMENTS

| 10,011,606 | B2 | 7/2018 | Kehler et al. |
| 2006/0135767 | A1 | 6/2006 | Feng et al. |
| 2008/0194592 | A1 | 8/2008 | Mates et al. |
| 2010/0190771 | A1 | 7/2010 | Claffey et al. |
| 2011/0281832 | A1 | 11/2011 | Li et al. |
| 2016/0083391 | A1 | 3/2016 | Burdi et al. |
| 2016/0083400 | A1 | 3/2016 | Burdi et al. |
| 2016/0311831 | A1 | 10/2016 | Kehler et al. |
| 2016/0318939 | A1 | 11/2016 | Kehler et al. |
| 2017/0291901 | A1 | 10/2017 | Juhl et al. |
| 2017/0291903 | A1 | 10/2017 | Kehler et al. |

FOREIGN PATENT DOCUMENTS

| EP | 2305262 | 4/2011 |
| GB | 973361 | 10/1964 |
| JP | 2015-052588 | 2/2016 |
| JP | 2016-011511 | 2/2016 |
| WO | WO 2004/018474 | 3/2004 |
| WO | WO 2004/026876 | 4/2004 |
| WO | WO 2004/099211 | 11/2004 |
| WO | WO 2008/070095 | 6/2008 |
| WO | WO 2008/139293 | 11/2008 |
| WO | WO 2009/121919 A1 | 10/2009 |
| WO | WO 2010/026214 A1 | 3/2010 |
| WO | WO 2010/065152 | 6/2010 |
| WO | WO 2010/084438 | 7/2010 |
| WO | WO 2011/153136 | 12/2011 |
| WO | WO 2012/040048 | 3/2012 |
| WO | WO 2012/040230 | 3/2012 |
| WO | WO 2012/171016 | 12/2012 |
| WO | WO 2013/053690 | 4/2013 |
| WO | WO 2013/110768 | 8/2013 |
| WO | WO 2013/192225 | 12/2013 |
| WO | WO 2013/192229 | 12/2013 |
| WO | WO 2014/151409 | 9/2014 |
| WO | WO 2016/042775 | 3/2016 |
| WO | WO 2016/055618 | 4/2016 |
| WO | WO 2016/147659 | 9/2016 |
| WO | WO 2016/170064 A1 | 10/2016 |
| WO | WO 2016/174188 | 11/2016 |
| WO | WO 2017/139186 | 8/2017 |
| WO | WO 2018/073251 A1 | 4/2018 |
| WO | WO 2018/078038 A1 | 5/2018 |
| WO | WO 2018/078042 A1 | 5/2018 |

OTHER PUBLICATIONS

U.S. Appl. No. 15/481,083, filed Apr. 6, 2017, Juhl et al.
U.S. Appl. No. 15/615,380, filed Jun. 6, 2017, Kehler et al.
[No Author Listed] FDA mulls drug to slow late-stage Alzheimer's. CNN Health. Sep. 24, 2003; http://www.cnn.com/2003/HEALTH/conditions/09/24/alzheimers.drug.ap/index.html [obtained Oct. 9, 2010].
Berge et al., Pharmaceutical Salts. J Pharm Sci. Jan. 1977;66(1):1-19.
Bernard et al., Transcriptional architecture of the primate neocortex. Neuron. Mar. 22, 2012;73(6):1083-99. doi: 10.1016/j.neuron.2012.03.002.
Blokland et al., PDE inhibition and cognition enhancement. Expert Opin Ther Pat. Apr. 2012;22(4):349-54. doi: 10.1517/13543776.2012.674514.
CAS Registry No. 1296334-75-2 (May 18, 2011).
Damasio et al., Alzheimer's Disease and Related Dementias. Cecil Textbook of Medicine. 20th edition. 1996;2:1992-1996.
Finlander et al., Phosphorus Pentoxide in Organic Synthesis V. Phosphorus Pentoxide and Amine Hydrochlorides as Reagents in the Synthesis of 1,5-dihydro-l-methyl-4H-pyrazolo[3,4-dlpyrimidin-4-ones. Chemica Scripta. 1983;22( 4):171-176 (Chemical Abstracts Only).
Francis et al., Mammalian cyclic nucleotide phosphodiesterases: molecular mechanisms and physiological functions. Physiol Rev. Apr. 2011;91(2):651-90. doi: 10.1152/physrev.00030.2010.

(Continued)

*Primary Examiner* — Paul V Ward
(74) *Attorney, Agent, or Firm* — Wolf, Greenfield & Sacks, P.C.

(57) ABSTRACT

The present invention provides triazolopyrazinones as PDE1 inhibitors and their use as a medicament, in particular for the treatment of neurodegenerative disorders and psychiatric disorders.

8 Claims, No Drawings

(56) References Cited

OTHER PUBLICATIONS

Medina, (2011) Therapeutic Utility of Phosphodiesterase Type I Inhibitors in Neurological Conditions. Front Neurosci. 2011; 5:21. Published online Feb. 18, 2011. Prepublished online Jan. 19, 2011. doi: 10.3389/fnins.2011.00021.

International Search Report and Written Opinion dated Jun. 2, 2016 for Application No. PCT/EP2016/058910.

International Search Report and Written Opinion dated Jul. 21, 2016 for Application No. PCT/EP2016/059583.

International Search Report and Written Opinion dated May 15, 2017 for Application No. PCT/EP2017/058332.

Chan, S., et al. (2011) "PDE1 Isozymes, Key Regulators of Pathological Vascular Remodeling," Curr. Opin. Pharmacol. 11(6):720-724.

International Search Report PCT/EP2015/073417 (WO 2016/055618) (2015) (4 pages).

Written Opinion of the International Searching Authority PCT/EP2015/073417 (WO 2016/055618) (2015) (5 pages).

International Search Report and Written Opinion dated Dec. 11, 2017 for Application No. PCT/EP2017/076481.

International Search Report and Written Opinion dated Feb. 2, 2018 for Application No. PCT/EP2017/077497.

International Search Report and Written Opinion dated Feb. 7, 2018 for Application No. PCT/EP2017/077503.

TRIAZOLOPYRAZINONES AS PDE1 INHIBITORS

CROSS-REFERENCE TO RELATED APPLICATIONS

This application is a § 371 National Stage Application of PCT/EP2015/073417 (filed on Oct. 9, 2015; pending), which application claims benefit of DK Patent Application No. PA 2014 00582, filed on Oct. 10, 2014. Each of these applications is hereby incorporated by reference in its entirety.

FIELD OF THE INVENTION

The present invention provides compounds that are PDE1 enzyme inhibitors and their use as a medicament, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of cN-concentrations in all cells, and their varied regulatory mechanisms provide for integration and crosstalk with myriad signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91: 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is Ca2+-dependently regulated via calmodulin (CaM, a 16 kDa Ca2+-binding protein) complexed with four Ca2+(for review, Sharron H. Francis, Mitsi A. Blount, and Jackie D. Corbin. Physiol Rev 2011, 91: 651-690). Thus, this family represents an interesting regulatory link between cyclic nucleotides and intracellular Ca2+. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain that contains two Ca2+/CaM binding domains and two phosphorylation sites differentiate their corresponding proteins and modulate their biochemical functions. PDE1 is a dual substrate PDE and the PDE1C-subtype has equal activity towards cAMP and cGMP (Km≈1-3 µM), whereas the subtypes PDE1A and PDE1B has a preference for cGMP (Km for cGMP=1-3 µM and for cAMP=10-30 µM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signalling pathways, preferably in the nervous system and PDE1 inhibitors can enhance the levels of the second messengers cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5 (Feb.), 21) have suggested the potential for the therapeutic use of PDE1 inhibitors in neurological disorders, like e.g. Alzheimer's, Parkinson's and Huntington's Diseases and in psychiatric disorders like e.g. Attention Deficit hyperactivity Disorder (ADHD), restless leg syndrome, depression, narcolepsy, cognitive impairment and cognitive impairment associated with schizophrenia (CIAS). There have also been patent applications claiming that PDE1 inhibitors are useful in diseases that may be alleviated by the enhancement of progesterone-signalling such as female sexual dysfunction.

The compounds of the invention may offer alternatives to current marketed treatments for neurodegenerative and/or psychiatric disorders, which are not efficacious in all patients. Hence, there remains a need for alternative methods of treatment.

Two compounds, namely 1,2,4-Triazolo[4,3-a]pyrazin-8 (7H)-one, 7-[(4-chlorophenyl)methyl]-3-methyl-(CAS Registry Number: 946270-18-4) and 1,2,4-Triazolo[4,3-a] pyrazin-8(7H)-one, 7-[(4-chlorophenyl)methyl]-3-propyl-(CAS Registry Number: 946237-23-6) are known in the prior art, but have not been disclosed as PDE1 inhibitors or for use as a medicament.

SUMMARY OF THE INVENTION

PDE1 enzymes are expressed in the Central Nervous System (CNS), making this gene family an attractive source of new targets for the treatment of psychiatric and neurodegenerative disorders.

The objective of the present invention is to provide compounds that are PDE1 inhibitors, and as such are useful to treat neurodegenerative disorders and psychiatric disorders.

Accordingly, the present invention relates to compounds of formula (I)

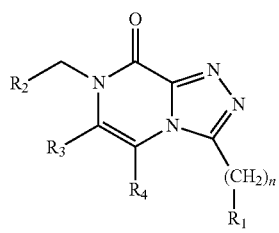

(I)

wherein
n is 0 or 1;
$R_1$ is selected from the group consisting of linear or branched $C_1$-$C_8$ alkyl, such as $C_1$ to $C_3$ alkyl, oxetanyl, tetrahydrofuranyl, tetrahydropyranyl and saturated monocyclic $C_3$-$C_8$ cycloalkyl; or
$R_1$ is selected from the group consisting oxetanyl, tetrahydrofuranyl, tetrahydropyranyl, saturated monocyclic $C_3$-$C_8$ cycloalkyl, each substituted one or two times with methyl or hydroxy, and linear or branched $C_1$-$C_8$ alkyl substituted one or more times, preferably one, two or three times, with fluorine; and
$R_2$ is selected from the group consisting of, linear or branched $C_1$-$C_8$ alkyl, phenyl, saturated monocyclic $C_3$-$C_8$ cycloalkyl, saturated bicyclic $C_4$-$C_{10}$ cycloalkyl, saturated tricyclic $C_7$-$C_{10}$ cycloalkyl, oxetanyl, tetrahydrofuranyl and tetrahydropyranyl; or
$R_2$ is selected from the group consisting of phenyl substituted with a substituent selected from the group consisting of halogen, linear or branched $C_1$-$C_3$ alkyl, difluoromethyl, trifluoromethyl and methoxy; saturated monocyclic $C_3$-$C_8$ cycloalkyl, substituted one or two times with substituents selected from the group consisting of fluorine and methyl; and oxetanyl, tetrahydrofuranyl and tetrahydropyranyl, each substituted one or two times with substituents selected from the group consisting of fluorine and methyl;
$R_3$ is selected from the group consisting of linear or branched $C_1$-$C_4$ alkyl, phenyl, substituted phenyl, halogen, tetrahydrofuranyl, benzyl, where the phenyl ring of the benzyl can be optionally substituted with one or more substituents chosen from haliogen, methyl, alkoxy or the phenyl ring of the benzyl can be substituted with an aromatic ring og heteroaromatic ring like e.g. pyridine;
$R_4$ is selected from the group consisting of linear or branched $C_1$-$C_4$ alkyl, halogen, and tetrahydrofuranyl.

Reference to Compound I includes the free base of Compound I, pharmaceutically acceptable salts of Compound I, such as acid addition salts of Compound I, racemic mixtures of Compound I, or the corresponding enantiomer and/or optical isomer of Compound I, and polymorphic and amorphic forms of Compound I as well as tautomeric forms of Compound I.

DETAILED DESCRIPTION OF THE INVENTION

Embodiments of the Invention

The following notation is applied: an embodiment of the invention is identified as Ei, where i is an integer indicating the number of the embodiment. An embodiment Ei' specifying a specific embodiment of a previously listed embodiment Ei is identified as Ei' (Ei), e.g. E2(E1) means "in an embodiment E2 of embodiment E1".

Where an embodiment is a combination of two embodiments the notation is similarly Ei"(Ei and Ei'), e.g. E3(E2 and E1) means "in an embodiment E3 of any of embodiments E2 and E1"

Where an embodiment is a combination of more than two embodiments the notation is similarly Ei'''(Ei, Ei' and Ei"), e.g. E4(E1, E2 and E3) means "in an embodiment E4 of any of embodiments E1, E2 and E3"

In a first embodiment E1 the present invention relates to compounds of formula (I) (Compound I):

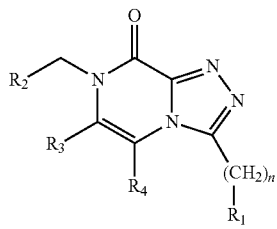

Compound (I)

wherein
n is 0 or 1;
$R_1$ is selected from the group consisting linear or branched $C_1$-$C_8$ alkyl, such as $C_1$ to $C_3$ alkyl, oxetanyl, tetrahydrofuranyl, tetrahydropyranyl and saturated monocyclic $C_3$-$C_8$ cycloalkyl; or
$R_1$ is selected from the group consisting oxetanyl, tetrahydrofuranyl, tetrahydropyranyl, saturated monocyclic $C_3$-$C_8$ cycloalkyl, each substituted one or two times with methyl or hydroxy, and linear or branched $C_1$-$C_8$ alkyl substituted one or more times, preferably one, two or three times, with fluorine; and
$R_2$ is selected from the group consisting of, linear or branched $C_1$-$C_8$ alkyl, phenyl, saturated monocyclic $C_3$-$C_8$ cycloalkyl, saturated bicyclic $C_4$-$C_{10}$ cycloalkyl, saturated tricyclic $C_7$-$C_{10}$ cycloalkyl, oxetanyl, tetrahydrofuranyl and tetrahydropyranyl; or
$R_2$ is selected from the group consisting of phenyl substituted with a substituent selected from the group consisting of halogen, $C_1$-$C_3$ alkyl, difluoromethyl, trifluoromethyl and methoxy; saturated monocyclic $C_3$-$C_8$ cycloalkyl, substituted one or two times with substituents selected from the group consisting of fluorine and methyl; and oxetanyl, tetrahydrofuranyl and tetrahydropyranyl, each substituted one or two times with substituents selected from the group consisting of fluorine and methyl;
$R_3$ is selected from the group consisting of linear or branched $C_1$-$C_4$ alkyl, phenyl, substituted phenyl, halogen and tetrahydrofuranyl; benzyl, where the phenyl ring of the benzyl can be optionally substituted with one or more substituents chosen from haliogen, methyl, alkoxy or the phenyl ring of the benzyl can be substituted with an aromatic ring og heteroaromatic ring like e.g. pyridine;

$R_4$ is selected from the group consisting of linear or branched $C_1$-$C_4$ alkyl, halogen, and tetrahydrofuranyl;
with the proviso that compound I is not 1,2,4-Triazolo[4,3-a]pyrazin-8(7H)-one, 7-[(4-chlorophenyl)methyl]-3-methyl-(CAS Registry Number: 946270-18-4) or 1,2,4-Triazolo[4,3-a]pyrazin-8(7H)-one, 7-[(4-chlorophenyl)methyl]-3-propyl-(CAS Registry Number: 946237-23-6).
E2(E1) $R_1$ is selected from methyl, ethyl, propyl and isopropyl.
E3(E2) $R_1$ is propyl
E4(E1) $R_2$ is phenyl
E5(E1) $R_2$ is substituted phenyl, wherein the substituent is selected from the group consisting of fluorine, chlorine and methoxy.
E6(E1) $R_2$ is substituted phenyl, wherein the substituent is selected from the group consisting of difluoromethyl and trifluoromethyl.
E7(E1) $R_2$ is saturated monocyclic $C_5$-$C_7$ cycloalkyl.
E8(E1, E3 and E7) $R_1$ is propyl and $R_2$ is saturated monocyclic $C_5$-$C_7$ cycloalkyl.
E9(E1) $R_2$ is adamantyl.
E10(E1) $R_2$ is a saturated spirooctan.
E11(E1) n is 0.
E12(E1) n is 1.
E13(E1) $R_3$ is methyl or ethyl.
E14(E1) $R_3$ is substituted phenyl, wherein the substituent is selected from the group consisting of phenyl, fluorine, and methyl.
E15(E1) $R_3$ is bromine.
E16(E1) $R_4$ is methyl or ethyl.
E17(E1) $R_4$ is bromine.
E18(E1), the compound of formula (I) is selected among the compounds listed in Table 1, in the form of the free base, one or more tautomers thereof or a pharmaceutically acceptable salt thereof.
E19(E1 to E18) the compound has an PDE1A, PDE1B or PDE1C $IC_{50}$ value, determined as described in the section "PDE1 inhibition assay", of 10 micro molar or less, such as 5 micro molar or less, such as 4 micro molar or less, such as 3 micro molar or less, such as 2 micro molar or less, such as 1 micro molar or less, such as 500 nM or less, such as 400 nM or less, such as 300 nM or less, such as 200 nM or less, such as 100 nM or less.
E20(E1) a compound selected from the compounds listed in Table 1 or pharmaceutically acceptable salts thereof.
E21(E1 to E20) the compound is for use as a medicament.
E22(E1 to E21) the compound is for use in the treatment of attention-deficit/hyperactivity disorder (ADHD).
E23(E1 to E20) a pharmaceutical composition comprising a therapeutically effective amount of a compound of any of embodiments (E1) to (E15), and one or more pharmaceutically acceptable carriers, diluents and excipients.
E24(E23) the pharmaceutical composition is for the treatment of attention-deficit/hyperactivity disorder (ADHD).
E25(E1 to E20) a method of treating a subject suffering from attention-deficit/hyperactivity disorder (ADHD), which method comprises administering to said subject an amount of a compound of formula I effective in inhibiting PDE1.
E26 (E1 to E21) the compound is for use in the treatment of cognitive problems in e.g. schizophrenia or Alzheimers disease.

DEFINITIONS

PDE1 Enzymes

The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms unless otherwise specified.

Substituents

As used in the context of the present invention, the terms "halo" and "halogen" are used interchangeably and refer to fluorine, chlorine, bromine or iodine.

A given range may interchangeably be indicated with "-" (dash) or "to", e.g. the term "$C_1$-$C_3$ alkyl" is equivalent to "$C_1$ to $C_3$ alkyl".

The terms "$C_1$-$C_3$ alkyl", "$C_1$-$C_4$ alkyl", "$C_1$-$C_5$ alkyl", "$C_1$-$C_6$ alkyl", "$C_1$-$C_7$ alkyl" and "$C_1$-$C_8$ alkyl" refer to a linear (i.e. unbranched) or branched saturated hydrocarbon having from one up to eight carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, n-hexyl, n-heptyl and n-octyl.

The term saturated monocyclic $C_3$ to $C_{10}$ cycloalkyl refers to cyclopropyl, cyclobutyl, cyclopentyl, cyclohexyl, cycloheptyl, cyclooctyl, cyclononyl and cyclodecatyl.

Corrrespondingly, the term saturated monocyclic $C_3$ to $C_8$ cycloalkyl refers to cyclopropyl, cyclobutyl, cyclopentyl, cyclohexyl, cycloheptyl and cyclooctyl.

The term saturated bicyclic $C_4$ to $C_{10}$ cycloalkyl refers to bicyclic ring comprising carbon and hydrogen atoms. Saturated bicyclic $C_4$ to $C_{10}$ cycloalkyl include spiro rings, fused rings and bridged rings, such as, but not limited to bicyclo [1.1.0]butanylbicyclobutanyl, bicyclo[2.1.0]pentanylbicyclopentanyl, bicyclo[2.2.0]hexanylbicyclohexanyl, bicyclo[2.2.1]heptanylbicycloheptanyl, bicyclo[2.2.2]octanylbicyclooctanyl, bicyclo[3.2.2]nonanyl and decahydronaphtalenylbicyclodecanyl.

The term saturated tricyclic $C_7$ to $C_{10}$ cycloalkyl refers to tricyclic ring comprising carbon and hydrogen atoms such as, but not limited to, adamantyl.

The expression "$C_1$-$C_3$ alkoxy" refers to a linear or branched saturated alkoxy group having from one to three carbon atoms, inclusive, with the open valency on the oxygen. Examples of such groups include methoxy, ethoxy, propoxy and isopropoxy.

Isomeric Forms

Where compounds of the present invention contain one or more chiral centers reference to any of the compounds will, unless otherwise specified, cover the enantiomerically or diastereomerically pure compound as well as mixtures of the enantiomers or diastereomers in any ratio.

For example reference to the compound 3-Propyl-7-((tetrahydro-2H-pyran-3-yl)methyl)-[1,2,4]triazolo[4,3-a]pyrazin-8(7H)-one without any further specification covers (R)-3-Propyl-7-((tetrahydro-2H-pyran-3-yl)methyl)-[1,2,4]triazolo[4,3-a]pyrazin-8(7H)-one, (S)-3-Propyl-7-((tetrahydro-2H-pyran-3-yl)methyl)-[1,2,4]triazolo[4,3-a]pyrazin-8(7H)-one as well as mixtures of the enantiomers in any ratio, including the racemic mixture (±)3-Propyl-7-((tetrahydro-2H-pyran-3-yl)methyl)-[1,2,4]triazolo[4,3-a]pyrazin-8(7H)-one.

The above also applies where compounds of the invention contain more than two chiral centers.

PDE1 Inhibitors

In the context of the present invention a compound is considered to be a PDE1 inhibitor if the amount required to reach the $IC_{50}$ level of any of the three PDE1 isoforms is 10 micro molar or less, preferably less than 9 micro molar, such as 8 micro molar or less, such as 7 micro molar or less, such as 6 micro molar or less, such as 5 micro molar or less, such as 4 micro molar or less, such as 3 micro molar or less, more preferably 2 micro molar or less, such as 1 micro molar or less, in particular 500 nM or less. In preferred embodiments the amount of PDE1 inhibitor required to reach the $C_{50}$ level of PDE1B is 400 n M or less, such as 300 nM or less, 200 nM or less, 100 nM or less, or even 80 nM or less, such as 50 nM or less, for example 25 nM or less.

Pharmaceutically Acceptable Salts

The present invention also comprises salts of the compounds of the invention, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Therapeutically Effective Amount

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

Pharmaceutical Compositions

The present invention further provides a pharmaceutical composition comprising a therapeutically effective amount of a compound of formula (I) and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21$^{st}$ Edition, Gennaro, Ed., Mack Publishing Co., Easton, Pa., 2005.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

The present invention also provides a process for making a pharmaceutical composition comprising mixing a therapeutically effective amount of a compound of formula (I) and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound which has the same utility as of a free base. When a compound of formula (I) contains a free base such salts are prepared in a conventional manner by treating a solution or suspension of a free base of formula (I) with a pharmaceutically acceptable acid. Representative examples of suitable organic and inorganic acids are described above.

For parenteral administration, solutions of the compounds of formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, and subcutaneous administration. The compounds of formula (I) may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula (I) and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tableting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Treatment of Disorders

As mentioned above, the compounds of formula (I) are PDE1 enzyme inhibitors and as such are useful to treat associated neurological and psychiatric disorders.

The invention thus provides a compound of formula (I) or a pharmaceutically acceptable acid addition salt thereof, as well as a pharmaceutical composition containing such a compound, for use in the treatment of a neurodegenerative disorder, psychiatric disorder or drug addiction in mammals including humans; wherein the neurodegenerative disorder is selected from the group consisting of Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline; and wherein the psychiatric disorder is selected from the group consisting of schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type; and wherein the drug addiction is an alcohol, amphetamine, cocaine, or opiate addiction.

The compounds of formula (I) or pharmaceutically acceptable salts thereof may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The present invention provides a method of treating a mammal, including a human, suffering from a neurodegenerative disorder selected from a cognition disorder or movement disorder, which method comprises administering to the subject a therapeutically effective amount of a compound of formula (I).

This invention further provides a method of treating a neurodegenerative disorder or condition in a mammal, including a human, which method comprises administering to said mammal an amount of a compound of formula (I) effective in inhibiting PDE1.

This invention also provides a method of treating a subject suffering from a psychiatric disorder, which method comprises administering to the subject a therapeutically effective amount of a compound of formula (I). Examples of psychiatric disorders that can be treated according to the present invention include, but are not limited to, Attention Deficit Hyperactivity Disorder (ADHD) schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type; and the anxiety disorder is selected from panic disorder; agoraphobia; a specific phobia; social phobia; obsessive-compulsive disorder; post-traumatic stress disorder; acute stress disorder; and generalized anxiety disorder.

It has been found that the compounds of formula (I) or pharmaceutically acceptable salts thereof may advantageously be administered in combination with at least one neuroleptic agent (which may be a typical or an atypical antipsychotic agent) to provide improved treatment of psychiatric disorders such as schizophrenia. The combinations, uses and methods of treatment of the invention may also provide advantages in treatment of patients who fail to respond adequately or who are resistant to other known treatments.

The present invention thus provides a method of treating a mammal suffering from a psychiatric disorder, such as schizophrenia, which method comprises administering to the mammal a therapeutically effective amount of a compound of formula (I), either alone or as combination therapy together with at least one neuroleptic agent.

The term "neuroleptic agent" as used herein refers to drugs, which have the effect on cognition and behaviour of antipsychotic agent drugs that reduce confusion, delusions, hallucinations, and psychomotor agitation in patients with psychoses. Also known as major tranquilizers and antipsychotic drugs, neuroleptic agents include, but are not limited to: typical antipsychotic drugs, including phenothiazines, further divided into the aliphatics, piperidines, and piperazines, thioxanthenes (e.g., cisordinol), butyrophenones (e.g., haloperidol), dibenzoxazepines (e.g., loxapine), dihydroindolones (e.g., molindone), diphenylbutylpiperidines (e.g., pimozide), and atypical antipsychotic drugs, including benzisoxazoles (e.g., risperidone), sertindole, olanzapine, quetiapine, osanetant and ziprasidone.

Particularly preferred neuroleptic agents for use in the invention are sertindole, olanzapine, risperidone, quetiapine, aripiprazole, haloperidol, clozapine, ziprasidone and osanetant.

The present invention further provides a method of treating a subject suffering from a cognition disorder, which method comprises administering to the subject a therapeutically effective amount of a compound of formula (I). Examples of cognition disorders that can be treated according to the present invention include, but are not limited to, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a movement disorder, which method comprises administering to the subject a therapeutically effective amount of a compound of formula (I). Examples of movement disorders that can be treated according to the present invention include, but are not limited to, Huntington's disease and dyskinesia associated with dopamine agonist therapy. This invention further provides a method of treating a movement disorder selected from Parkinson's disease and restless leg syndrome, which comprises administering to the subject a therapeutically effective amount of a compound of formula (I).

This invention also provides a method of treating a mood disorder, which method comprises administering to the subject a therapeutically effective amount of a compound of formula (I). Examples of mood disorders and mood episodes that can be treated according to the present invention include, but are not limited to, major depressive episode of the mild, moderate or severe type, a manic or mixed mood episode, a hypomanic mood episode; a depressive episode with a typical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder. It is understood that a mood disorder is a psychiatric disorder.

This invention further provides a method of treating a disorder comprising as a symptom a deficiency in attention and/or cognition in a mammal, including a human, which method comprises administering to said mammal an amount of a compound of formula (I) effective in treating said disorder.

Other disorders that can be treated according to the present invention are obsessive/compulsive disorders, Tourette's syndrome and other tic disorders.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temporal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the present invention, the neurodegenerative disorder or condition involves neurodegeneration of striatal medium spiny neurons in a mammal, including a human.

In a further embodiment of the present invention, the neurodegenerative disorder or condition is Huntington's disease. All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Compounds of the Invention

TABLE 1

Compounds of the invention

| Compound | PDE1C inhibition[a] (nM or %) | PDE1B inhibition[a] (nM or %) | PDE1A inhibition[a] (nM or %) |
|---|---|---|---|
| 3-Propyl-7-((tetrahydro-2H-pyran-3-yl)methyl)-[1,2,4]triazolo[4,3-a]pyrazin-8(7H)-one, stereoisomer 1 | 68% | 57% | 48% |
| 3-Propyl-7-((tetrahydro-2H-pyran-3-yl)methyl)-[1,2,4]triazolo[4,3-a]pyrazin-8(7H)-one, stereoisomer 2 | 48% | 33% | 26% |
| 7-(Cyclohexylmethyl)-3-propyl-[1,2,4]triazolo[4,3-a]pyrazin-8(7H)-one | 47 nM | 81 nM | 96 nM |
| 7-(Cyclopentylmethyl)-3-propyl-[1,2,4]triazolo[4,3-a]pyrazin-8(7H)-one | 95 nM | 820 nM | 840 nM |
| 3-Propyl-7-((tetrahydro-2H-pyran-4-yl)methyl)-[1,2,4]triazolo[4,3-a]pyrazin-8(7H)-one | 1600 nM | 47% | 42% |
| 7-Isobutyl-3-propyl-[1,2,4]triazolo[4,3-a]pyrazin-8(7H)-one | 970 nM | 2700 nM | 3300 nM |
| 7-(Cyclopropylmethyl)-3-propyl-[1,2,4]triazolo[4,3-a]pyrazin-8(7H)-one | 1300 nM | 2000 nM | 3600 nM |
| 7-Ethyl-3-propyl-[1,2,4]triazolo[4,3-a]pyrazin-8(7H)-one | 52% | 71% | 49% |
| 7-(Oxetan-3-ylmethyl)-3-propyl-[1,2,4]triazolo[4,3-a]pyrazin-8(7H)-one | 57% | 46% | 37% |
| 7-(Cycloheptylmethyl)-3-propyl-[1,2,4]triazolo[4,3-a]pyrazin-8(7H)-one | 33 nM | 28 nM | 54 nM |
| 3-Propyl-7-((tetrahydrofuran-3-yl)methyl)-[1,2,4]triazolo[4,3-a]pyrazin-8(7H)-one, stereisomer 1 | 55% | 67% | 35% |
| 3-Propyl-7-((tetrahydrofuran-3-yl)methyl)-[1,2,4]triazolo[4,3-a]pyrazin-8(7H)-one, stereisomer 2 | 74% | 4000 nM | 60% |
| 7-Benzyl-3-propyl-[1,2,4]triazolo[4,3-a]pyrazin-8(7H)-one | 110 nM | 400 nM | 770 nM |
| 7-(2-Fluorobenzyl)-3-propyl-[1,2,4]triazolo[4,3-a]pyrazin-8(7H)-one | 130 nM | 1000 nM | 860 nM |
| 7-(3-Fluorobenzyl)-3-(tetrahydro-2H-pyran-4-yl)-[1,2,4]triazolo[4,3-a]pyrazin-8(7H)-one | 140 nM | 680 nM | 730 nM |
| 7-(3-Fluorobenzyl)-3-propyl-[1,2,4]triazolo[4,3-a]pyrazin-8(7H)-one | 190 nM | 1200 nM | 1100 nM |
| 7-(3-Methylbenzyl)-3-propyl-[1,2,4]triazolo[4,3-a]pyrazin-8(7H)-one | 170 nM | 1600 nM | 1500 nM |
| 3-Propyl-7-(4-(trifluoromethyl)benzyl)-[1,2,4]triazolo[4,3-a]pyrazin-8(7H)-one | 2100 nM | 570 nM | 1200 nM |
| 7-(3-Fluorobenzyl)-3-((tetrahydrofuran-3-yl)methyl)-[1,2,4]triazolo[4,3-a]pyrazin-8(7H)-one | 420 nM | 1900 nM | 1200 nM |
| 3-Propyl-7-(2-(trifluoromethyl)benzyl)-[1,2,4]triazolo[4,3-a]pyrazin-8(7H)-one | 41% | 46% | 44% |
| 7-(2-Chlorobenzyl)-3-propyl-[1,2,4]triazolo[4,3-a]pyrazin-8(7H)-one | 430 nM | 2500 nM | 2000 nM |
| 7-(4-Chlorobenzyl)-3-propyl-[1,2,4]triazolo[4,3-a]pyrazin-8(7H)-one | 170 nM | 83 nM | 620 nM |
| 7-(4-Chlorobenzyl)-3-(tetrahydrofuran-3-yl)-[1,2,4]triazolo[4,3-a]pyrazin-8(7H)-one | 750 nM | 840 nM | 500 nM |

TABLE 1-continued

Compounds of the invention

| Compound | PDE1C inhibition[a] (nM or %) | PDE1B inhibition[a] (nM or %) | PDE1A inhibition[a] (nM or %) |
|---|---|---|---|
| 7-Hexyl-3-(tetrahydro-2H-pyran-4-yl)-[1,2,4]triazolo[4,3-a]pyrazin-8(7H)-one | 1100 nM | 1000 nM | 1260 nM |
| 7-(4-Fluorobenzyl)-3-propyl-[1,2,4]triazolo[4,3-a]pyrazin-8(7H)-one | 360 nM | 1200 nM | 970 nM |
| 7-(4-Chlorobenzyl)-3-ethyl-[1,2,4]triazolo[4,3-a]pyrazin-8(7H)-one | 2400 nM | 800 nM | 1000 nM |
| 7-(3-Chlorobenzyl)-3-propyl-[1,2,4]triazolo[4,3-a]pyrazin-8(7H)-one | 160 nM | 1300 nM | 1400 nM |
| 7-(4-Methylbenzyl)-3-propyl-[1,2,4]triazolo[4,3-a]pyrazin-8(7H)-one | 780 nM | 930 nM | 1000 nM |
| 7-(2-Methylbenzyl)-3-propyl-[1,2,4]triazolo[4,3-a]pyrazin-8(7H)-one | 2400 nM | 42% | 53% |
| 3-Cyclopentyl-7-(3-fluorobenzyl)-[1,2,4]triazolo[4,3-a]pyrazin-8(7H)-one | 800 nM | 290 nM | 420 nM |
| 7-Isopentyl-3-(tetrahydro-2H-pyran-4-yl)-[1,2,4]triazolo[4,3-a]pyrazin-8(7H)-one | 1100 nM | 55% | 47% |
| 3-Cyclopropyl-7-(3-fluorobenzyl)-[1,2,4]triazolo[4,3-a]pyrazin-8(7H)-one | 210 nM | 780 nM | 500 nM |
| 3-Cyclohexyl-7-(3-fluorobenzyl)-[1,2,4]triazolo[4,3-a]pyrazin-8(7H)-one | 120 nM | 590 nM | 810 nM |
| 7-(3-Fluorobenzyl)-3-(tetrahydro-2H-pyran-2-yl)-[1,2,4]triazolo[4,3-a]pyrazin-8(7H)-one, stereoisomer 1 | 390 nM | 2200 nM | 3200 nM |
| 7-(3-Fluorobenzyl)-3-(tetrahydro-2H-pyran-2-yl)-[1,2,4]triazolo[4,3-a]pyrazin-8(7H)-one, stereoisomer 2 | 470 nM | 3400 nM | 3200 nM |
| 7-(3-Fluorobenzyl)-3-(tetrahydrofuran-3-yl)-[1,2,4]triazolo[4,3-a]pyrazin-8(7H)-one, stereoisomer 1 | 240 nM | 2100 nM | 1800 nM |
| 7-(3-Fluorobenzyl)-3-(tetrahydrofuran-3-yl)-[1,2,4]triazolo[4,3-a]pyrazin-8(7H)-one, stereoisomer 2 | 240 nM | 1800 nM | 2100 nM |
| 7-(3-Fluorobenzyl)-3-(2-fluoroethyl)-[1,2,4]triazolo[4,3-a]pyrazin-8(7H)-one | 620 nM | 3000 nM | 2900 nM |
| 3-(1,1-Difluoroethyl)-7-(3-fluorobenzyl)-[1,2,4]triazolo[4,3-a]pyrazin-8(7H)-one | 550 nM | 2700 nM | 2500 nM |
| 7-(3-Fluorobenzyl)-3-(tetrahydro-2H-pyran-3-yl)-[1,2,4]triazolo[4,3-a]pyrazin-8(7H)-one, stereoisomer 1 | 350 nM | 2700 nM | 1800 nM |
| 7-(3-Fluorobenzyl)-3-(tetrahydro-2H-pyran-3-yl)-[1,2,4]triazolo[4,3-a]pyrazin-8(7H)-one, stereoisomer 2 | 200 nM | 1300 nM | 1800 nM |
| 7-(3-Fluorobenzyl)-3-(tetrahydrofuran-2-yl)-[1,2,4]triazolo[4,3-a]pyrazin-8(7H)-one Stereoisomer 1 | 700 nM | 4400 nM | 2700 nM |
| 7-(3-Fluorobenzyl)-3-(tetrahydrofuran-2-yl)-[1,2,4]triazolo[4,3-a]pyrazin-8(7H)-one Stereoisomer 2 | 240 nM | 660 nM | 890 nM |
| 7-(3-Fluorobenzyl)-3-((tetrahydrofuran-2-yl)methyl)-[1,2,4]triazolo[4,3-a]pyrazin-8(7H)-one, stereoisomer 1 | 870 nM | 3700 nM | 67% |
| 7-(3-Fluorobenzyl)-3-((tetrahydrofuran-2-yl)methyl)-[1,2,4]triazolo[4,3-a]pyrazin-8(7H)-one, stereoisomer 2 | 1200 nM | 67% | 49% |
| 7-(3-Fluorobenzyl)-3-(2,2,2-trifluoroethyl)-[1,2,4]triazolo[4,3-a]pyrazin-8(7H)-one | 380 nM | 1400 nM | 2000 nM |
| 7-(3-Fluorobenzyl)-3-(oxetan-3-yl)-[1,2,4]triazolo[4,3-a]pyrazin-8(7H)-one | 1700 nM | 7200 nM | 67% |
| 7-(3-Fluorobenzyl)-3-(1-fluoroethyl)-[1,2,4]triazolo[4,3-a]pyrazin-8(7H)-one, stereoisomer 2 | 1000 nM | 4000 nM | 2900 nM |
| 7-(3-Fluorobenzyl)-3-(1-fluoroethyl)-[1,2,4]triazolo[4,3-a]pyrazin-8(7H)-one, stereoisomer 1 | 420 nM | 2600 nM | 1400 nM |
| 7-(3-Fluorobenzyl)-3-(heptan-3-yl)-[1,2,4]triazolo[4,3-a]pyrazin-8(7H)-one, | 480 nM | 1600 nM | 3200 nM |
| 7-(3-Fluorobenzyl)-3-((tetrahydrofuran-3-yl)methyl)-[1,2,4]triazolo[4,3-a]pyrazin-8(7H)-one, stereoisomer 1 | 720 nM | 2500 nM | 2500 nM |

TABLE 1-continued

Compounds of the invention

| Compound | PDE1C inhibition[a] (nM or %) | PDE1B inhibition[a] (nM or %) | PDE1A inhibition[a] (nM or %) |
|---|---|---|---|
| 7-(3-Fluorobenzyl)-3-((tetrahydrofuran-3-yl)methyl)-[1,2,4]triazolo[4,3-a]pyrazin-8(7H)-one, stereoisomer 2 | 510 nM | 2000 nM | 2100 nM |
| 7-((4,4-Dimethylcyclohexyl)methyl)-3-propyl-[1,2,4]triazolo[4,3-a]pyrazin-8(7H)-one | 110 nM | 110 nM | 130 nM |
| 7-(Cycloheptylmethyl)-3-(tetrahydro-2H-pyran-4-yl)-[1,2,4]triazolo[4,3-a]pyrazin-8(7H)-one | 42 nM | 33 nM | 43 nM |
| 7-(((3r,5r,7r)-Adamantan-1-yl)methyl)-3-propyl-[1,2,4]triazolo[4,3-a]pyrazin-8(7H)-one | 63 nM | 210 nM | 180 nM |
| 7-((4-Methylcyclohexyl)methyl)-3-propyl-[1,2,4]triazolo[4,3-a]pyrazin-8(7H)-one | 65 nM | 53 nM | 83 nM |
| 7-((1-Methylcyclohexyl)methyl)-3-propyl-[1,2,4]triazolo[4,3-a]pyrazin-8(7H)-one | 260 nM | 950 nM | 1300 nM |
| 7-((4,4-Difluorocyclohexyl)methyl)-3-propyl-[1,2,4]triazolo[4,3-a]pyrazin-8(7H)-one | 760 nM | 420 nM | 450 nM |
| 7-(Cyclopentylmethyl)-3-(tetrahydro-2H-pyran-4-yl)-[1,2,4]triazolo[4,3-a]pyrazin-8(7H)-one | 110 nM | 990 nM | 1100 nM |
| 7-(Cyclohexylmethyl)-3-(tetrahydro-2H-pyran-4-yl)-[1,2,4]triazolo[4,3-a]pyrazin-8(7H)-one | 87 nM | 190 nM | 220 nM |
| 3-Propyl-7-(spiro[2.5]octan-6-ylmethyl)-[1,2,4]triazolo[4,3-a]pyrazin-8(7H)-one | 92 nM | 53 nM | 86 nM |
| 7-((3-Methylcyclohexyl)methyl)-3-propyl-[1,2,4]triazolo[4,3-a]pyrazin-8(7H)-one | 83 nM | 230 nM | 320 nM |
| 7-((2-Methylcyclohexyl)methyl)-3-propyl-[1,2,4]triazolo[4,3-a]pyrazin-8(7H)-one | 240 nM | 260 nM | 320 nM |
| 7-(((1r,3r,5r,7r)-Adamantan-2-yl)methyl)-3-propyl-[1,2,4]triazolo[4,3-a]pyrazin-8(7H)-one | 63 nM | 210 nM | 179 nM |
| 7-((4-Fluorocyclohexyl)methyl)-3-propyl-[1,2,4]triazolo[4,3-a]pyrazin-8(7H)-one | 610 nM | 560 nM | 660 nM |
| 7-(3-Fluorobenzyl)-3-((1s,4s)-4-hydroxycyclohexyl)-[1,2,4]triazolo[4,3-a]pyrazin-8(7H)-one | 350 nM | 1000 nM | 1800 nM |
| 7-(3-Fluorobenzyl)-3-((1r,4r)-4-hydroxycyclohexyl)-[1,2,4]triazolo[4,3-a]pyrazin-8(7H)-one | 200 nM | 630 nM | 1000 nM |
| 7-(((1s,4s)-4-methylcyclohexyl)methyl)-3-propyl-[1,2,4]triazolo[4,3-a]pyrazin-8(7H)-one | 36 nM | 24 nM | 111 nM |
| 7-(((1r,4r)-4-methylcyclohexyl)methyl)-3-propyl-[1,2,4]triazolo[4,3-a]pyrazin-8(7H)-one | 120 nM | 40 nM | 79 nM |
| 6-bromo-7-(3-fluorobenzyl)-3-propyl-[1,2,4]triazolo[4,3-a]pyrazin-8(7H)-one | 20 nM | 99 nM | 63 nM |
| 6-bromo-7-(3-fluorobenzyl)-3-(tetrahydro-2H-pyran-4-yl)-[1,2,4]triazolo[4,3-a]pyrazin-8(7H)-one | 24 nM | 150 nM | 114 nM |
| 6-bromo-7-(cyclopentylmethyl)-3-(tetrahydro-2H-pyran-4-yl)-[1,2,4]triazolo[4,3-a]pyrazin-8(7H)-one | 6 nM | 140 nM | 164 nM |
| 6-bromo-7-(cyclohexylmethyl)-3-(tetrahydro-2H-pyran-4-yl)-[1,2,4]triazolo[4,3-a]pyrazin-8(7H)-one | 3 nM | 17 nM | 12 nM |
| 6-bromo-7-(cycloheptylmethyl)-3-(tetrahydro-2H-pyran-4-yl)-[1,2,4]triazolo[4,3-a]pyrazin-8(7H)-one | 3 nM | 4 nM | 13 nM |
| 6-benzyl-7-methyl-3-(tetrahydro-2H-pyran-4-yl)-[1,2,4]triazolo[4,3-a]pyrazin-8(7H)-one | 2800 nM | 1600 nM | 2000 nM |
| 7-(4-methoxybenzyl)-6-methyl-3-(tetrahydro-2H-pyran-4-yl)-[1,2,4]triazolo[4,3-a]pyrazin-8(7H)-one | 37 nM | 34 nM | 54 nM |
| 7-(4-methoxybenzyl)-6-methyl-3-propyl-[1,2,4]triazolo[4,3-a]pyrazin-8(7H)-one | 44 nM | 32 nM | 66 nM |
| 7-((4-methoxycyclohexyl)methyl)-6-methyl-3-propyl-[1,2,4]triazolo[4,3-a]pyrazin-8(7H)-one (cis) | n.d. | n.d. | n.d. |

TABLE 1-continued

Compounds of the invention

| Compound | PDE1C inhibition[a] (nM or %) | PDE1B inhibition[a] (nM or %) | PDE1A inhibition[a] (nM or %) |
|---|---|---|---|
| 7-((4-methoxycyclohexyl)methyl)-6-methyl-3-propyl-[1,2,4]triazolo[4,3-a]pyrazin-8(7H)-one (trans) | n.d. | n.d. | n.d. |
| Cis 6-methyl-7-((4-methylcyclohexyl)methyl)-3-propyl-[1,2,4]triazolo[4,3-a]pyrazin-8(7H)-one | n.d. | n.d. | n.d. |
| Trans 6-methyl-7-((4-methylcyclohexyl)methyl)-3-propyl-[1,2,4]triazolo[4,3-a]pyrazin-8(7H)-one | n.d. | n.d. | n.d. |
| 7-((4-methoxycyclohexyl)methyl)-6-methyl-3-(tetrahydro-2H-pyran-4-yl)-[1,2,4]triazolo[4,3-a]pyrazin-8(7H)-one (cis) | n.d. | n.d. | n.d. |
| 7-((4-methoxycyclohexyl)methyl)-6-methyl-3-(tetrahydro-2H-pyran-4-yl)-[1,2,4]triazolo[4,3-a]pyrazin-8(7H)-one (trans) | n.d. | n.d. | n.d. |
| Cis 6-methyl-7-((4-methylcyclohexyl)methyl)-3-(tetrahydro-2H-pyran-4-yl)-[1,2,4]triazolo[4,3-a]pyrazin-8(7H)-one | n.d. | n.d. | n.d. |
| Trans 6-methyl-7-((4-methylcyclohexyl)methyl)-3-(tetrahydro-2H-pyran-4-yl)-[1,2,4]triazolo[4,3-a]pyrazin-8(7H)-one | n.d. | n.d. | n.d. |
| 6-([1,1'-biphenyl]-4-ylmethyl)-7-(cyclohexylmethyl)-3-(tetrahydro-2H-pyran-4-yl)-[1,2,4]triazolo[4,3-a]pyrazin-8(7H)-one | 0.10 nM | 0.17 nM | 0.33 nM |
| 7-(3-fluorobenzyl)-6-(3-methylbenzyl)-3-(tetrahydro-2H-pyran-4-yl)-[1,2,4]triazolo[4,3-a]pyrazin-8(7H)-one | 2 nM | 9 nM | 6 nM |
| 7-(cyclohexylmethyl)-6-(3-methylbenzyl)-3-(tetrahydro-2H-pyran-4-yl)-[1,2,4]triazolo[4,3-a]pyrazin-8(7H)-one | 1 nM | 3 nM | 2 nM |
| 7-(cyclopentylmethyl)-6-(3-methylbenzyl)-3-(tetrahydro-2H-pyran-4-yl)-[1,2,4]triazolo[4,3-a]pyrazin-8(7H)-one | 4 nM | 37 nM | 17 nM |
| 7-(cycloheptylmethyl)-6-(4-fluorobenzyl)-3-(tetrahydro-2H-pyran-4-yl)-[1,2,4]triazolo[4,3-a]pyrazin-8(7H)-one | 4 nM | 9 nM | 3 nM |
| 6-benzyl-7-(cycloheptylmethyl)-3-(tetrahydro-2H-pyran-4-yl)-[1,2,4]triazolo[4,3-a]pyrazin-8(7H)-one | 2 nM | 4 nM | 1 nM |
| 6,7-bis(3-fluorobenzyl)-3-(tetrahydro-2H-pyran-4-yl)-[1,2,4]triazolo[4,3-a]pyrazin-8(7H)-one | 8 nM | 40 nM | 47 nM |
| 7-(cyclohexylmethyl)-6-(3-fluorobenzyl)-3-(tetrahydro-2H-pyran-4-yl)-[1,2,4]triazolo[4,3-a]pyrazin-8(7H)-one | 6 nM | 22 nM | 24 nM |
| 7-(cyclopentylmethyl)-6-(3-fluorobenzyl)-3-(tetrahydro-2H-pyran-4-yl)-[1,2,4]triazolo[4,3-a]pyrazin-8(7H)-one | 27 nM | 220 nM | 369 nM |
| 7-(3-fluorobenzyl)-6-(4-fluorobenzyl)-3-(tetrahydro-2H-pyran-4-yl)-[1,2,4]triazolo[4,3-a]pyrazin-8(7H)-one | 10 nM | 43 nM | 46 nM |
| 7-(cyclohexylmethyl)-6-(4-fluorobenzyl)-3-(tetrahydro-2H-pyran-4-yl)-[1,2,4]triazolo[4,3-a]pyrazin-8(7H)-one | 6 nM | 17 nM | 12 nM |
| 7-(cyclopentylmethyl)-6-(4-fluorobenzyl)-3-(tetrahydro-2H-pyran-4-yl)-[1,2,4]triazolo[4,3-a]pyrazin-8(7H)-one | 12 nM | 140 nM | 142 nM |
| 7-(cycloheptylmethyl)-6-(2-methylbenzyl)-3-(tetrahydro-2H-pyran-4-yl)-[1,2,4]triazolo[4,3-a]pyrazin-8(7H)-one | 14 nM | 39 nM | 25 nM |

TABLE 1-continued

| Compounds of the invention | | | |
|---|---|---|---|
| Compound | PDE1C inhibition[a] (nM or %) | PDE1B inhibition[a] (nM or %) | PDE1A inhibition[a] (nM or %) |
| 7-(cycloheptylmethyl)-6-(4-methylbenzyl)-3-(tetrahydro-2H-pyran-4-yl)-[1,2,4]triazolo[4,3-a]pyrazin-8(7H)-one | 0.37 nM | 1 nM | 0.86 nM |
| 7-(cyclohexylmethyl)-6-(4-methylbenzyl)-3-(tetrahydro-2H-pyran-4-yl)-[1,2,4]triazolo[4,3-a]pyrazin-8(7H)-one | 1 nM | 2 nM | 1 nM |
| 7-(cyclopentylmethyl)-6-(4-methylbenzyl)-3-(tetrahydro-2H-pyran-4-yl)-[1,2,4]triazolo[4,3-a]pyrazin-8(7H)-one | 3 nM | 19 nM | 21 nM |
| 7-(cyclohexylmethyl)-6-(2-methylbenzyl)-3-(tetrahydro-2H-pyran-4-yl)-[1,2,4]triazolo[4,3-a]pyrazin-8(7H)-one | 10 nM | 44 nM | 41 nM |
| 7-(cyclopentylmethyl)-6-(2-methylbenzyl)-3-(tetrahydro-2H-pyran-4-yl)-[1,2,4]triazolo[4,3-a]pyrazin-8(7H)-one | 23 nM | 260 nM | 251 nM |
| 6-benzyl-7-(cyclopentylmethyl)-3-(tetrahydro-2H-pyran-4-yl)-[1,2,4]triazolo[4,3-a]pyrazin-8(7H)-one | 5 nM | 46 nM | 65 nM |
| 6-benzyl-7-(cyclohexylmethyl)-3-(tetrahydro-2H-pyran-4-yl)-[1,2,4]triazolo[4,3-a]pyrazin-8(7H)-one | 4 nM | 11 nM | 11 nM |
| 7-(3-fluorobenzyl)-6-(4-methylbenzyl)-3-(tetrahydro-2H-pyran-4-yl)-[1,2,4]triazolo[4,3-a]pyrazin-8(7H)-one | 1 nM | 6 nM | 7 nM |
| 7-(3-fluorobenzyl)-6-(2-methylbenzyl)-3-(tetrahydro-2H-pyran-4-yl)-[1,2,4]triazolo[4,3-a]pyrazin-8(7H)-one | 17 nM | 82 nM | 91 nM |
| 6-benzyl-7-(4-fluorobenzyl)-3-(tetrahydro-2H-pyran-4-yl)-[1,2,4]triazolo[4,3-a]pyrazin-8(7H)-one | 6 nM | 12 nM | 15 nM |
| (R)-7-(3-fluorobenzyl)-3-propyl-6-(tetrahydrofuran-3-yl)-[1,2,4]triazolo[4,3-a]pyrazin-8(7H)-one | 290 nM | 1800 nM | 2976 nM |
| (S)-7-(3-fluorobenzyl)-3-propyl-6-(tetrahydrofuran-3-yl)-[1,2,4]triazolo[4,3-a]pyrazin-8(7H)-one | 270 nM | 1100 nM | 1105 nM |
| 7-(3-fluorobenzyl)-6-methyl-3-propyl-[1,2,4]triazolo[4,3-a]pyrazin-8(7H)-one | 46 nM | 190 nM | 236 nM |
| 7-(3-fluorobenzyl)-6-ethyl-3-propyl-[1,2,4]triazolo[4,3-a]pyrazin-8(7H)-one | 50 nM | 180 nM | 117 nM |
| 6-benzyl-7-(3-fluorobenzyl)-3-(tetrahydro-2H-pyran-4-yl)-[1,2,4]triazolo[4,3-a]pyrazin-8(7H)-one | 5 nM | 18 nM | 32 nM |
| (R)-7-(3-fluorobenzyl)-3-propyl-5-(tetrahydrofuran-3-yl)-[1,2,4]triazolo[4,3-a]pyrazin-8(7H)-one | 260 nM | 2300 nM | 1605 nM |
| (S)-7-(3-fluorobenzyl)-3-propyl-5-(tetrahydrofuran-3-yl)-[1,2,4]triazolo[4,3-a]pyrazin-8(7H)-one | 260 nM | 1000 nM | 1784 nM |
| 7-(3-fluorobenzyl)-3-propyl-5-methyl-[1,2,4]triazolo[4,3-a]pyrazin-8(7H)-one | 260 nM | 1000 nM | 1365 nM |
| 7-(3-fluorobenzyl)-3-propyl-5-ethyl)-[1,2,4]triazolo[4,3-a]pyrazin-8(7H)-one | 180 nM | 510 nM | 858 nM |
| 5-bromo-7-(3-fluorobenzyl)-3-propyl-[1,2,4]triazolo[4,3-a]pyrazin-8(7H)-one | 72 nM | 180 nM | 149 nM | n.d. means "not determined"

[a]IC50 refers to the concentration (nM) of the compound required to reach 50% inhibition of the enzyme at the specified substrate concentration % inhib refers to the % inhibition of the enzyme at a concentration of 10 micro molar of the compound.

EXPERIMENTAL SECTION

Preparation of the Compounds of the Invention

General Methods

Analytical LC-MS data were obtained using one of the methods identified below.

Method 1:

A Waters Acquity UPLC-MS was used. Column: Acquity UPLC BEH C18 1.7 µm; 2.1×50 mm; Column temperature: 60° C.; Solvent system: A=water/trifluoroacetic acid (99.965:0.035) and B=acetonitrile/water/trifluoroacetic acid (94.965:5:0.035); Method:Linear gradient elution with A:B=90:10 to 0:100 in 1.0 minutes and with a flow rate of 1.2 mL/minute.

Method 2:

A Waters Acquity UPLC-MS was used. Column: Acquity UPLC BEH C18 1.7 µm; 2.1×50 mm; Column temperature: 60° C.; Solvent system: A=water/formic acid (99.9:0.1) and B=acetonitrile/water/formic acid (94.9:5:0.1); Method:Linear gradient elution with A:B=90:10 to 0:100 in 1.0 minutes and with a flow rate of 1.2 mL/minute.

Method 3:

An Agilent 1200 LCMS system with ELS detector was used. Column: Agilent TC-C18 5 µm; 2.1×50 mm; Column temperature: 50° C.; Solvent system: A=water/trifluoroacetic acid (99.9:0.1) and B=acetonitrile/trifluoroacetic acid (99.95:0.05); Method:Linear gradient elution with A:B=99:1 to 0:100 in 4.0 minutes and with a flow rate of 0.8 mL/minute.

Method 4:

An Agilent 1200 LCMS system with ELS detector was used. Column: XBridge ShieldRP18, 5 µm, 50×2.1 mm; Column temperature: 40° C.; Solvent system: A=water/NH$_3$*H2O (99.95:0.05) and B=acetonitrile; Method:Linear gradient elution with A:B=95:5 to 0:100 in 3.4 minutes and with a flow rate of 0.8 mL/minute.

Method 5:

A Waters Acquity UPLC-MS was used. Column: Acquity UPLC HSS T3 C18 1.8 µm; 2.1×50 mm; Column temperature: 60° C.; Solvent system: A=water/trifluoroacetic acid (99.965:0.035) and B=acetonitrile/water/trifluoroacetic acid (94.965:5:0.035); Method:Linear gradient elution with A:B=98:02 to 0:100 in 1.0 minutes and with a flow rate of 1.2 mL/min.

Method 6:

An Agilent 1200 LCMS system with ELS detector was used. Column: Waters XBridge ShieldRP18, 2.1*50 mm, 5 µm; Column temperature: 40° C.; Solvent system: A=water/ammonia (99.95:0.05) and B=acetonitrile; Method:Linear gradient elution with A:B=95:5 to 0:100 in 4.0 minutes and with a flow rate of 0.8 mL/min.

Method 7:

A Shimadzu 20 MS instrument equipped with atmospheric pressure photo ionisation ion source and a Shimadzu LC-20AB system was used. Column: MERCK, RP-18e 25-2 mm; Column temperature: 50° C.; Solvent system: A=water/trifluoroacetic acid (99.9625:0.0375) and B=acetonitrile/trifluoroacetic acid (99.981:0.019); Method: A linear gradient elution A:B=95:5 to A:B=5:95 in 0.7 minutes, then A:B=5:95 for 0.4 minutes, then with a linear gradient elution to A:B 95:5 for 0.4 minutes with a constant flow rate of 1.5 mL/min.

Method 8:

An Agilent 1100 LCMS system with ELS detector was used. Column: YMC ODS-AQ 5 µm; 2.0×50 mm; Column temperature: 50° C.; Solvent system: A=water/trifluoroacetic acid (99.9:0.1) and B=acetonitrile/trifluoroacetic acid (99.95:0.05); Method:Linear gradient elution with A:B=99:1 to 5:95 in 3.5 minutes and with a flow rate of 0.8 mL/min.

Method 9:

An Agilent 1100 LCMS system with ELS detector was used. Column: YMC ODS-AQ 5 µm; 2.0×50 mm; Column temperature: 50° C.; Solvent system: A=water/trifluoroacetic acid (99.9:0.1) and B=acetonitrile/trifluoroacetic acid (99.95:0.05); Method:Linear gradient elution with A:B=90:10 to 0:100 in 3.5 minutes and with a flow rate of 0.8 mL/min.

Preparative SFC was performed on a Thar 80 instrument. Exemplified conditions can be, but not limited to: Column AD 250×30 mm with 20 µm particle size; Column temperature: 38° C., Mobile phase: Supercritical CO$_2$/EtOH (0.2% NH$_3$H$_2$O)=45/55.

The Following Abbreviations have been Used:

DME dimethoxyethane
DCM dichloromethane
TEA triethyl amine
THF tetrahydrofurane
EtOAc ethyl acetate
DMF N,N-dimethylformamide
DIPEA N,N-diisopropylethyl amine
MeOH Methanol
MTBE methyl tert-butyl ether
HATU 1-[Bis(dimethylamino)methylene]-1H-1,2,3-triazolo[4,5-b]pyridinium 3-oxid hexafluorophosphate
RT room temperature
SFC Supercritical Fluid Chromatography Example 1

Intermediate 1

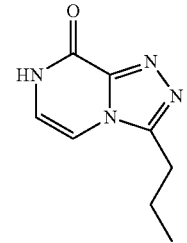

3-Propyl-[1,2,4]triazolo[4,3-a]pyrazin-8(7H)-one

To a solution of commercial available 2-chloro-3-hydrazinylpyrazine (28 g, 0.19 mol) in dichloromethane (200 mL) was added butyraldehyde (14.7 g, 0.20 mol) and the reaction was stirred at 50° C. for 2 hours before cooling to 0° C. Diacetoxyiodobenzene (71.8 g, 0.223 mol) was added at 0° C. Cooling was removed and the mixture was stirred at 20° C. for 2 hours. A saturated aq. solution of Na$_2$CO$_3$ (80 mL) was slowly poured into the reaction and the mixture was stirred for 10 minutes. The organic phase was separated, washed with brine (3×50 mL), dried over Na$_2$SO$_4$ and concentrated under vacuum. The residue was purified by flash chromatography on silica gel using a gradient of ethyl acetate and petroleum ether to give 8-chloro-3-propyl-[1,2,4]triazolo[4,3-a]pyrazine 20 g (53%).

A mixture of 8-chloro-3-propyl-[1,2,4]triazolo[4,3-a]pyrazine (10 g, 51 mmol) and conc. aq. HCl (21 mL) in dioxane (120 mL) and H₂O (50 mL) was stirred at 100° C. for 12 hours. The solution was cooled to 20° C. and sat. aq. NaHCO₃ was added to adjust pH to 8. The mixture was concentrated under vacuum, the residue was washed with water and dried to give 3-propyl-[1,2,4]triazolo[4,3-a]pyrazin-8(7H)-one 8 g (88%).

Example 2

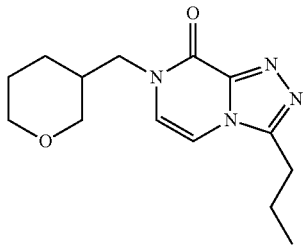 [SMILES: CCCc1nnc2c(=O)n(CC3CCCOC3)ccn12]

3-Propyl-7-((tetrahydro-2H-pyran-3-yl)methyl)-[1,2,4]triazolo[4,3-a]pyrazin-8(7H)-one Step 1:
To a solution of (tetrahydro-2H-pyran-3-yl)methanol (300 mg, 2.58 mmol) and TEA (522 mg, 5.17 mmol) in dichloromethane (10 mL) was added methanesulfonyl chloride (355 mg, 3.10 mmol) at 0° C. and the reaction was allowed to warm to 20° C. and stirred for 1 hour. The solution was washed with sat. aq. NaHCO₃ (2 mL), H₂O (3×2 mL), brine (1 mL), dried and concentrated to give (tetrahydro-2H-pyran-3-yl)methyl methanesulfonate (500 mg), which was used in the next step directly.

Step 2:
To a solution of (tetrahydro-2H-pyran-3-yl)methyl methanesulfonate (500 mg, 2.58 mmol) and 3-propyl-[1,2,4]triazolo[4,3-a]pyrazin-8(7H)-one (413 mg, 2.32 mmol) in DMF (30 mL) was added K₂CO₃ (534 mg, 3.87 mmol). The mixture was stirred at 60° C. for 4 hours. The reaction was cooled to RT and diluted with DCM (100 mL). The organic phase was washed with H₂O (2×10 mL), dried over Na₂SO₄ and evaporated. The residue was washed with MeOH (2 mL) to give 3-propyl-7-((tetrahydro-2H-pyran-3-yl)methyl)-[1,2,4]triazolo[4,3-a]pyrazin-8(7H)-one 400 mg (56%).

The racemate of 3-propyl-7-((tetrahydro-2H-pyran-3-yl)methyl)-[1,2,4]triazolo[4,3-a]pyrazin-8(7H)-one 400 mg was purified by SFC and the enantiomers numbered according to their order of elution.

Stereoisomer 1:
160 mg (40%), ¹H NMR (CDCl₃ varian 400): δ 6.93 (d, J=6.0 Hz, 1H), 6.66 (d, J=6.0 Hz, 1H), 4.03-3.94 (m, 1H), 3.89-3.74 (m, 3H), 3.60-3.50 (m, 1H), 3.37 (dd, J=11.6, 7.6 Hz, 1H), 2.97 (t, J=7.6 Hz, 2H), 2.23-2.12 (m, 1H), 1.97-1.80 (m, 3H), 1.78-1.68 (m, 1H), 1.62-1.53 (m, 1H), 1.50-1.40 (m, 1H), 1.06 (t, J=7.4 Hz, 3H). LCMS (MH+): m/z=277.2, $t_R$ (minutes, Method 3)=1.99
[α]$_D^{20}$=−11.33 (c=0.10, MeOH).

Stereoisomer 2:
170 mg (42%), ¹H NMR (CDCl₃ varian 400): δ 6.94 (d, J=6.0 Hz, 1H), 6.66 (d, J=6.4 Hz, 1H), 4.01-3.94 (m, 1H), 3.89-3.74 (m, 3H), 3.60-3.51 (m, 1H), 3.37 (dd, J=11.6, 7.6 Hz, 1H), 2.97 (t, J=7.6 Hz, 2H), 2.23-2.12 (m, 1H), 1.97-1.80 (m, 3H), 1.78-1.68 (m, 1H), 1.62-1.53 (m, 1H), 1.50-1.40 (m, 1H), 1.06 (t, J=7.4 Hz, 3H). LCMS (MH+): m/z=277.2, $t_R$ (minutes, Method 3)=1.99
[α]$_D^{20}$=+12.33 (c=0.10, MeOH).

Example 3

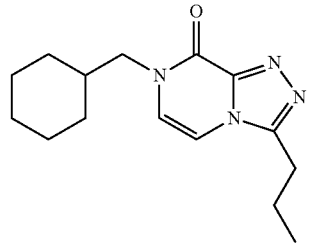 [SMILES: CCCc1nnc2c(=O)n(CC3CCCCC3)ccn12]

7-(Cyclohexylmethyl)-3-propyl-[1,2,4]triazolo[4,3-a]pyrazin-8(7H)-one

To a solution of 3-propyl-[1,2,4]triazolo[4,3-a]pyrazin-8(7H)-one (200 mg, 1.1 mmol) and (bromomethyl)cyclohexane (239 mg, 1.35 mmol) in DMF (2 mL) was added K₂CO₃ (310 mg, 2.2 mmol). The reaction was stirred at 60° C. for 4 hours and then cooled to RT. DCM (20 mL) was added and the organic phase was washed with water (2×5 mL). The organic layer was dried over Na₂SO₄ and evaporated. The residue was washed with MeOH (2 mL) to give 7-(cyclohexylmethyl)-3-propyl-[1,2,4]triazolo[4,3-a]pyrazin-8(7H)-one 190 mg (61%). ¹H NMR (CDCl₃, 400 MHz TMS): δ 6.90 (d, J=5.6 Hz, 1H), 6.62 (d, J=5.6 Hz, 1H), 3.79 (d, J=7.2 Hz, 2H), 2.96 (t, J=7.6 Hz, 2H), 1.93-1.88 (m, 3H), 1.75-1.61 (m, 5H), 1.21-1.18 (m, 3H), 1.08-1.01 (m, 5H). LCMS (MH+): m/z=275.2, $t_R$ (minutes, Method 3)=2.57

Example 4

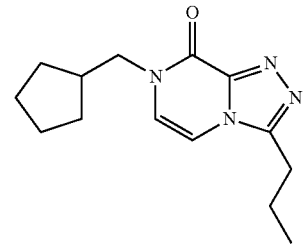 [SMILES: CCCc1nnc2c(=O)n(CC3CCCC3)ccn12]

7-(Cyclopentylmethyl)-3-propyl-[1,2,4]triazolo[4,3-a]pyrazin-8(7H)-one

To a solution of 3-propyl-[1,2,4]triazolo[4,3-a]pyrazin-8(7H)-one (200 mg, 1.1 mmol) and (bromomethyl)cyclopentane (283 mg, 1.35 mmol) in DMF (2 mL) was added K₂CO₃ (310 mg, 2.2 mmol). The reaction was stirred at 60° C. for 4 hours and then cooled to RT. The mixture was diluted with DCM (20 mL) and washed with water (2×5 mL). The organic layer was dried over Na₂SO₄ and evaporated. The crude product was washed with MeOH (2 mL) to give 7-(cyclopentylmethyl)-3-propyl-[1,2,4]triazolo[4,3-a]pyrazin-8(7H)-one 120 mg (41%). ¹H NMR (CDCl₃, 400

MHz TMS): δ 6.91 (d, J=5.6 Hz, 1H), 6.66 (d, J=5.6 Hz, 1H), 3.89 (d, J=8.0 Hz, 2H), 2.94 (t, J=7.6 Hz, 2H), 2.37-2.31 (m, 1H), 1.92-1.86 (m, 2H), 1.73-1.68 (m, 4H), 1.63-1.56 (m, 2H), 1.32-1.27 (m, 2H), 1.04 (t, J=7.4 Hz, 3H). LCMS (MH+): m/z=261.1, $t_R$(minutes, Method 3)=2.41

Example 5

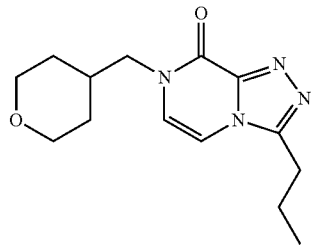 [SMILES: CCCc1nnc2c(=O)n(CC3CCOCC3)ccn12]

3-Propyl-7-((tetrahydro-2H-pyran-4-yl)methyl)-[1,2,4]triazolo[4,3-a]pyrazin-8(7H)-one To a solution of 3-propyl-[1,2,4]triazolo[4,3-a]pyrazin-8(7H)-one (200 mg, 1.1 mmol) and 4-(bromomethyl)tetrahydro-2H-pyran (241 mg, 1.35 mmol) in DMF (2 mL) was added K$_2$CO$_3$ (310 mg, 2.2 mmol). The mixture was stirred at 60° C. for 4 hours and then cooled to RT. The reaction mixture was diluted with DCM (20 mL) and washed with water (2×5 mL). The organic phase was dried over Na$_2$SO$_4$ and evaporated. The crude product was washed with MeOH (2 mL) to give 3-propyl-7-((tetrahydro-2H-pyran-4-yl)methyl)-[1,2,4]triazolo[4,3-a]pyrazin-8(7H)-one 120 mg (54%). $^1$H NMR (CDCl$_3$, 400 MHz TMS): δ 6.91 (d, J=6.0 Hz, 1H), 6.62 (d, J=6.0 Hz, 1H), 3.96 (dd, J=11.6, 3.2 Hz, 2H), 3.82 (d, J=7.6 Hz, 2H), 3.34 (td, J=11.6, 1.6 Hz, 2H), 2.94 (t, J=7.6 Hz, 2H), 2.20-2.10 (m, 1H), 1.91-1.86 (m, 2H), 1.61-1.58 (m, 2H), 1.40 (dq, J=4.0, 12.0 Hz, 2H), 1.04 (t, J=7.6 Hz, 3H). LCMS (MH+): m/z=277.1, $t_R$ (minutes, Method 3)=1.93

Example 6

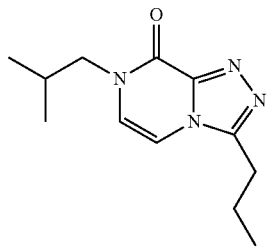 [SMILES: CCCc1nnc2c(=O)n(CC(C)C)ccn12]

7-Isobutyl-3-propyl-[1,2,4]triazolo[4,3-a]pyrazin-8(7H)-one

To a solution of 3-propyl-[1,2,4]triazolo[4,3-a]pyrazin-8(7H)-one (200 mg, 1.1 mmol) and 1-bromo-2-methylpropane (231 mg, 1.68 mmol) in DMF (2 mL) was added K$_2$CO$_3$ (185 mg, 1.34 mmol). The mixture was stirred at 60° C. for 12 hours and then cooled to RT. The reaction mixture was diluted with DCM (20 mL) and washed with water (2×5 mL). The organic phase was dried over Na$_2$SO$_4$ and evaporated. The residue was washed with MeOH (2 mL) to give 7-isobutyl-3-propyl-[1,2,4]triazolo[4,3-a]pyrazin-8(7H)-one 160 mg (61%). $^1$H NMR (CDCl$_3$, 400 MHz TMS): δ 6.93 (d, J=6.0 Hz, 1H), 6.65 (d, J=6.0 Hz, 1H), 3.78 (d, J=7.6 Hz, 2H), 2.96 (t, J=7.6 Hz, 2H), 2.20-2.14 (m, 1H), 1.95-1.88 (m, 2H), 1.06 (t, J=7.4 Hz, 3H), 0.98 (d, J=6.6 Hz, 6H). LCMS (MH+): m/z=235.2, $t_R$ (minutes, Method 3)=2.16

Example 7

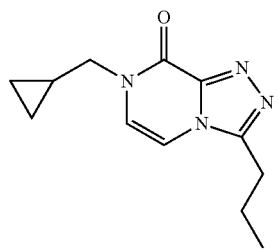 [SMILES: CCCc1nnc2c(=O)n(CC3CC3)ccn12]

7-(Cyclopropylmethyl)-3-propyl-[1,2,4]triazolo[4,3-a]pyrazin-8(7H)-one

To a solution of 3-propyl-[1,2,4]triazolo[4,3-a]pyrazin-8(7H)-one (200 mg, 1.1 mmol) and (bromomethyl)cyclopropane (227 mg, 1.68 mmol) in DMF (2 mL) was added K$_2$CO$_3$ (186 mg, 1.35 mmol). The mixture was stirred at 60° C. for 12 hours and then cooled to RT. To the reaction mixture was added DCM (20 mL) and it was washed with water (2×5 mL). The organic layer was dried over Na$_2$SO$_4$ and evaporated. The residue was washed with MeOH (2 mL) to give 7-(cyclopropylmethyl)-3-propyl-[1,2,4]triazolo[4,3-a]pyrazin-8(7H)-one 60 mg (23%). $^1$H NMR (CDCl$_3$, 400 MHz TMS): δ 6.97 (d, J=6.0 Hz, 1H), 6.82 (d, J=5.6 Hz, 1H), 3.85 (d, J=7.2 Hz, 2H), 2.97 (t, J=7.6 Hz, 2H), 1.94-1.87 (m, 2H), 1.15-1.27 (m, 1H), 1.06 (t, J=7.4 Hz, 3H), 0.60-0.68 (m, 2H), 0.45-0.42 (m, 2H). LCMS (MH+): m/z=233.2, $t_R$ (minutes, Method 3)=2.06

Example 8

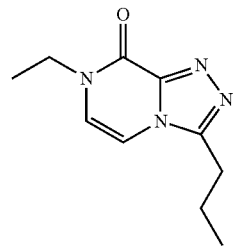

7-Ethyl-3-propyl-[1,2,4]triazolo[4,3-a]pyrazin-8(7H)-one

To a solution of 3-propyl-[1,2,4]triazolo[4,3-a]pyrazin-8(7H)-one (200 mg, 1.1 mmol) and iodoethane (262 mg, 1.68 mmol) in DMF (2 mL) was added K$_2$CO$_3$ (186 mg, 1.34 mmol). The mixture was stirred at 60° C. for 12 hours and then cooled to RT. The reaction mixture was diluted with DCM (20 mL) and washed with H$_2$O (2×5 mL). The organic layer was dried over Na$_2$SO$_4$ and evaporated. The residue was washed with MeOH (2 mL) to give 7-ethyl-3-propyl-[1,2,4]triazolo[4,3-a]pyrazin-8(7H)-one 60 mg (26%). $^1$H NMR (CDCl$_3$, 400 MHz TMS): δ 6.96 (d, J=5.8 Hz, 1H), 6.69 (d, J=5.8 Hz, 1H), 4.03 (q, J=7.1 Hz, 2H), 2.96 (t, J=7.6 Hz, 2H), 1.95-1.86 (m, 2H), 1.38 (t, J=7.2 Hz, 3H), 1.06 (t, J=7.4 Hz, 3H). LCMS (MH+): m/z=207.1, t$_R$ (minutes, Method 3)=1.81

Example 9

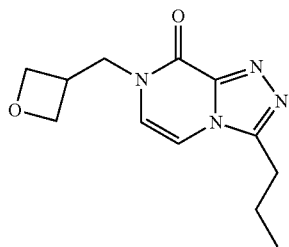 [SMILES: CCCc1nnc2c(=O)n(CC3COC3)ccn12]

7-(Oxetan-3-ylmethyl)-3-propyl-[1,2,4]triazolo[4,3-a]pyrazin-8(7H)-one

Step 1:

To a solution of oxetan-3-ylmethanol (500 mg, 5.67 mmol) and Et$_3$N (1.15 g, 11.4 mmol) in DCM (20 mL) was added methanesulfonyl chloride (780 mg, 6.81 mmol) at 0° C. Cooling was removed and the mixture was stirred at 20° C. for 1 hour. The reaction mixture was diluted with 2 M NaHCO$_3$ (5 mL) then brine (5 mL). The organic layer was dried over Na$_2$SO$_4$ and evaporated to give oxetan-3-ylmethyl methanesulfonate 920 mg (97%).

Step 2:

To a solution of 3-propyl-[1,2,4]triazolo[4,3-a]pyrazin-8(7H)-one (200 mg, 1.1 mmol) and oxetan-3-ylmethyl methanesulfonate (249 mg, 1.35 mmol) in DMF (2 mL) was added K$_2$CO$_3$ (310 mg, 2.20 mmol). The mixture was stirred at 60° C. for 4 hours and then cooled to RT. The reaction mixture was diluted with DCM (20 mL) and washed with water (2×5 mL). The organic phase was dried over Na$_2$SO$_4$ and evaporated. The residue was washed with ethyl acetate (4 mL) to give 7-(oxetan-3-ylmethyl)-3-propyl-[1,2,4]triazolo[4,3-a]pyrazin-8(7H)-one 40 mg (14%). $^1$H NMR (CDCl$_3$, 400 MHz TMS): δ 6.88 (d, J=6.0 Hz, 1H), 6.62 (d, J=6.0 Hz, 1H), 4.75 (t, J=7.2 Hz, 2H), 4.46 (t, J=6.4 Hz, 2H), 4.22 (d, J=7.2 Hz, 2H), 3.50-3.40 (m, 1H), 2.89 (t, J=7.6 Hz, 2H), 1.89-1.79 (m, 2H), 0.99 (t, J=7.6 Hz, 3H). LCMS (MH+): m/z=249.1, t$_R$ (minutes, Method 3)=1.38

Example 10

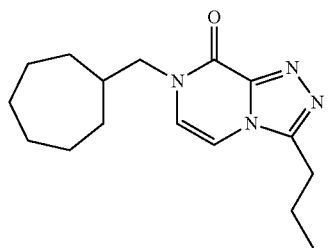 [SMILES: CCCc1nnc2c(=O)n(CC3CCCCCC3)ccn12]

7-(Cycloheptylmethyl)-3-propyl-[1,2,4]triazolo[4,3-a]pyrazin-8(7H)-one

Step 1:

To a solution of cycloheptanecarboxylic acid (200 mg, 1.41 mmol) in THF (15 mL) was added 1 M BH$_3$.THF (2.8 mL, 2.8 mmol) at 0° C. and it was then heated to 70° C. and stirred for 12 hours. The solution was cooled to 20° C. and MeOH (4 mL) was added, the reaction was stirred at 65° C. for 2 hours before it was cooled to RT and concentrated in vacuo. The residue was purified by flash chromatography on silica gel using a gradient of ethyl acetate petroleum ether to give cycloheptylmethanol 150 mg (83%).

Step 2:

To a solution of cycloheptylmethanol (150 mg, 1.17 mmol) and TEA (236 mg, 2.34 mmol) in DCM (5 mL) was added methanesulfonyl chloride (201 mg, 2.75 mmol) at 0° C. and it was allowed to warm to 20° C. and stirred for 0.5 hour. The solution was washed with sat. aq. NaHCO$_3$ (2 mL), H$_2$O (3×2 mL), brine (1 mL), dried over Na$_2$SO$_4$ and concentrated to give cycloheptylmethyl methanesulfonate (250 mg), which was used in the next step directly.

Step 3:

To a solution of cycloheptylmethyl methanesulfonate (250 mg) and 3-propyl-[1,2,4]triazolo[4,3-a]pyrazin-8(7H)-one (187 mg, 1.05 mmol) in DMF (5 mL) was added K$_2$CO$_3$ (241 mg, 1.75 mmol). The mixture was stirred at 60° C. for 12 hours. The reaction mixture was diluted with DCM (20 mL) and washed with water (2×5 mL). The organic phase was dried over Na$_2$SO$_4$ and evaporated. The residue was washed with MeOH (2 mL) to give 7-(cycloheptylmethyl)-3-propyl-[1,2,4]triazolo[4,3-a]pyrazin-8(7H)-one 100 mg (33%). $^1$H NMR (CDCl$_3$, 400 MHz TMS): δ 6.91 (d, J=6.0 Hz, 1H), 6.64 (d, J=6.0 Hz, 1H), 3.79 (d, J=7.2 Hz, 2H), 2.96 (t, J=7.6 Hz, 2H), 2.08-2.00 (m, 1H), 1.96-1.87 (m, 2H), 1.71-1.65 (m, 4H), 1.61-1.38 (m, 6H), 1.30-1.21 (m, 2H), 1.07 (t, J=7.4 Hz, 3H). LCMS (MH+): m/z=289.1, t$_R$ (minutes, Method 3)=2.31

Example 11

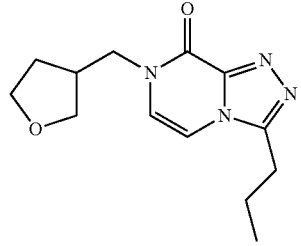 [SMILES: CCCc1nnc2c(=O)n(CC3CCOC3)ccn12]

3-Propyl-7-((tetrahydrofuran-3-yl)methyl)-[1,2,4]triazolo[4,3-a]pyrazin-8(7H)-one Step 1:

To a solution of tetrahydrofuran-3-carboxylic acid (600 mg, 5.17 mmol) in THF (15 mL) was added a solution of 1 M BH$_3$.THF in THF (10.3 mL, 10.3 mmol) at 0° C. The reaction was heated to 65° C. and stirred for 12 hours. The solution was then cooled to 20° C. and MeOH (4 mL) was added. The reaction was then stirred at 65° C. for 2 hours before cooling to RT and concentrated in vacuo. The residue was purified by flash chromatography on silica gel using a gradient of ethyl acetate and petroleum ether to give (tetrahydrofuran-3-yl)methanol 200 mg (38%).

Step 2:

To a solution of (tetrahydrofuran-3-yl)methanol (200 mg, 1.96 mmol) and TEA (396 mg, 3.92 mmol) in DCM (15 mL) was added methanesulfonyl chloride (448 mg, 3.92 mmol) at 0° C. The reaction was heated at 20° C. and stirred for 1 hour. The solution was washed with sat. aq. NaHCO$_3$ (2 mL), H$_2$O (3×2 mL), brine (1 mL) dried and concentrated to give (tetrahydrofuran-3-yl)methyl methanesulfonate (400 mg), which was used in the next step directly.

Step 3:

To a solution of (tetrahydrofuran-3-yl)methyl methanesulfonate (400 mg) and 3-propyl-[1,2,4]triazolo[4,3-a]pyrazin-8(7H)-one (348 mg, 1.95 mmol) in DMF (10 mL) was added K$_2$CO$_3$ (539 mg, 3.91 mmol). The mixture was stirred at 60° C. for 12 hours. The mixture was diluted with DCM (100 mL) and washed with H$_2$O (2×10 mL). The organic layer was dried over Na$_2$SO$_4$ and evaporated. The residue was washed with MeOH (2 mL) to give 3-propyl-7-((tetrahydrofuran-3-yl)methyl)-[1,2,4]triazolo[4,3-a]pyrazin-8(7H)-one 200 mg (39%).

The racemate of 3-propyl-7-((tetrahydrofuran-3-yl)methyl)-[1,2,4]triazolo[4,3-a]pyrazin-8(7H)-one 200 mg was purified by SFC and the enantiomers numbered according to their order of elution.

Stereoisomer 1:

160 mg (40%), $^1$H NMR (CDCl$_3$ varian 400 MHz): δ 6.95 (d, J=5.9 Hz, 1H), 6.68 (d, J=6.1 Hz, 1H), 4.08 (dd, J=13.5, 7.3 Hz, 1H), 4.00-3.94 (m, 1H), 3.86-3.74 (m, 3H), 3.63 (dd, J=9.1, 4.9 Hz, 1H), 2.97 (t, J=7.6 Hz, 2H), 2.91-2.80 (m, 1H), 2.13-2.02 (m, 1H), 1.96-1.87 (m, 2H), 1.77-1.69 (m, 1H), 1.06 (t, J=7.6 Hz, 3H). LCMS (MH+): m/z=263.1, $t_R$ (minutes, Method 3)=1.85

[α]$D^{20}$=+9.33° (c=0.10, MeOH).

Stereoisomer 2:

170 mg (43%), $^1$H NMR (CDCl$_3$ varian 400 MHz): δ 6.94 (d, J=6.0 Hz, 1H), 6.68 (d, J=6.0 Hz, 1H), 4.09 (dd, J=13.5, 7.3 Hz, 1H), 4.00-3.94 (m, 1H), 3.86-3.74 (m, 3H), 3.63 (dd, J=9.1, 4.9 Hz, 1H), 2.97 (t, J=7.6 Hz, 2H), 2.91-2.80 (m, 1H), 2.13-2.02 (m, 1H), 1.96-1.87 (m, 2H), 1.77-1.69 (m, 1H), 1.06 (t, J=7.4 Hz, 3H). LCMS (MH+): m/z=263.1, $t_R$ (minutes, Method 3)=1.86

[α]$D^{20}$=−7.67° (c=0.10, MeOH).

Example 12

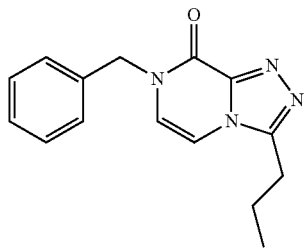 [SMILES: CCCc1nnc2c(=O)n(Cc3ccccc3)ccn12]

7-Benzyl-3-propyl-[1,2,4]triazolo[4,3-a]pyrazin-8(7H)-one

8-Chloro-3-propyl-[1,2,4]triazolo[4,3-a]pyrazine (101 mg, 0.514 mmol) and phenylmethanol (100 mg, 0.925 mmol) were dissolved in dimethoxyethane (3 mL), NaH 60% in mineral oil (41 mg, 1.0 mmol) was added, and the mixture was stirred at RT for 1 hour. Sodium iodide (154 mg, 1.03 mmol) was added and the reaction was heated at 200° C. for 20 min under microwave irradiation. The reaction was filtered and concentrated in vacuo. The crude product was purified by column chromatography using a gradient of (petroleum ether:EtOAc:5% Et$_3$N/10% MeOH/85% EtOAc=1:0:0 to 0:1:0 to 0:0:1) to afford 7-benzyl-3-propyl-[1,2,4]triazolo[4,3-a]pyrazin-8(7H)-one 65 mg (45%). %), $^1$H NMR (CDCl$_3$ 500 MHz): δ7.38 (m, 5H), 6.92 (d, J=6.0 Hz, 1H), 6.68 (d, J=6.0 Hz, 1H), 5.17 (s, 2H), 2.97 (t, J=7.6 Hz, 2H), 1.96-1.87 (m, 2H), 1.06 (t, J=7.4 Hz, 3H). LCMS (MH+): m/z=269.2, $t_R$ (minutes, Method 1)=0.50

Example 13

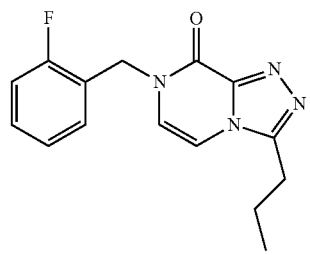 [SMILES: CCCc1nnc2c(=O)n(Cc3ccccc3F)ccn12]

7-(2-Fluorobenzyl)-3-propyl-[1,2,4]triazolo[4,3-a]pyrazin-8(7H)-one

8-Chloro-3-propyl-[1,2,4]triazolo[4,3-a]pyrazine (116 mg, 0.590 mmol), (2-fluorophenyl) methanol (134 mg, 1.06 mmol) were dissolved in dimethoxyethane (3.5 ml), NaH 60% in mineral oil (43 mg, 1.1 mmol) was added and the reaction was stirred at RT for 2 hours. Sodium iodide (177 mg, 1.18 mmol) was added and the reaction was heated at 200° C. for 20 minutes under microwave irradiation. The reaction was filtered and concentrated in vacuo. The crude product was purified by column chromatography using a gradient of (petroleum ether:EtOAc: 5% Et$_3$N/10% MeOH/85% EtOAc=1:0:0 to 0:1:0 to 0:0:1) to afford 7-(2-fluorobenzyl)-3-propyl-[1,2,4]triazolo[4,3-a]pyrazin-8(7H)-one 8 mg (9%). %), $^1$H NMR (CDCl$_3$ 500 MHz): δ7.56 (m, 1H), 7.35 (m, 1H), 7.17 (m, 1H), 7.12 (m, 1H), 6.92 (d, J=6.0 Hz, 1H), 6.82 (d, J=6.0 Hz, 1H), 5.22 (s, 2H), 2.94 (t, J=7.6 Hz, 2H), 1.92 (m, 2H), 1.06 (t, J=7.4 Hz, 3H). LCMS (MH+): m/z=287.2, $t_R$ (minutes, Method 1)=0.51

Example 14

Intermediate 2

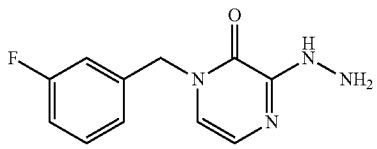 [SMILES: NNc1nccn(Cc2cccc(F)c2)c1=O]

1-(3-Fluorobenzyl)-3-hydrazinylpyrazin-2(1H)-one

Step 1:

To a solution of (3-fluorophenyl)methanamine (10.0 g, 80.0 mmol) in THF (40 mL) was slowly added ethyl 2-chloro-2-oxoacetate (9.78 mL, 87.9 mmol) at 0° C. Then the mixture was stirred at RT for 30 minutes. Then a solution of 2,2-dimethoxyethan-1-amine (10.5 mL, 95.9 mmol) and DIPEA (41.8 mL, 239 mmol) in ethylacetate (40 mL) was added to the mixture. The reaction mixture was heated at reflux overnight and then cooled to RT. To the reaction mixture was added sat. aq. NaHCO$_3$ (50 mL) and it was extracted with ethyl acetate (50 mL). The organic phase was dried over Na$_2$SO$_4$, filtered, concentrated in vacuo and purified by column chromatography on silica gel using a gradient of DCM and methanol (DCM/MeOH=100/1 to 20/1) to give N1-(2,2-dimethoxyethyl)-N2-(3-fluorobenzyl) oxalamide 15 g (66%).
Step 2:
To a solution of N1-(2,2-dimethoxyethyl)-N2-(3-fluorobenzyl)oxalamide (1.00 g, 3.52 mmol) in acetic acid (20 mL) was added trifluoroacetic acid (0.3 mL). Then the reaction was heated at 140° C. for 2 hours and cooled to RT. The crude mixture was concentrated and the residue was added to MTBE (50 mL) and sat. aq. NaHCO$_3$ (50 mL). The resulting precipitate was collected by filtration, washed with H$_2$O (50 mL) and MTBE (50 mL) to give 1-(3-fluorobenzyl)-1,4-dihydropyrazine-2,3-dione 500 mg (64%).
LCMS (MH+): m/z=221.1, t$_R$ (minutes, Method 3)=1.95
Step 3:
1-(3-Fluorobenzyl)-1,4-dihydropyrazine-2,3-dione (8.0 g, 36 mmol) was slowly added to POCl$_3$ (35 mL). The mixture was heated at 80° C. for 1 hour and then cooled to RT. The crude reaction mixture was poured onto ice-water (100 mL), pH was adjusted around 7 by addition of sat. aq. NaHCO$_3$ (1 L). The mixture was extracted with DCM (2×500 mL). The combined organic phases were dried over Na$_2$SO$_4$, filtered, concentrated and purified by column chromatography silica gel using a gradient of ethyl acetate and DCM (DCM/EtOAc=100/1 to 30/1) to give 3-chloro-1-(3-fluorobenzyl)pyrazin-2(1H)-one 6 g (69%).
Step 4:
To a solution of 3-chloro-1-(3-fluorobenzyl)pyrazin-2 (1H)-one (1 g, 4.19 mmol) in EtOH (30 mL) was added NH$_2$NH$_2$—H$_2$O (1 mL). The mixture was stirred at 40° C. overnight and then cooled to 0° C. The precipitate was filtered off and washed with water (20 mL), cold EtOH (20 mL) and dried to give 1-(3-fluorobenzyl)-3-hydrazinylpyrazin-2(1H)-one 800 mg (81%).

Example 15

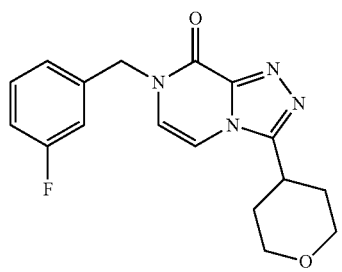 [SMILES: O=c1c2nnc(C3CCOCC3)n2ccn1Cc1cccc(F)c1]

7-(3-Fluorobenzyl)-3-(tetrahydro-2H-pyran-4-yl)-[1,2,4]triazolo[4,3-a]pyrazin-8(7H)-one Step 1:
To a cooled (0° C.) solution of 1-(3-fluorobenzyl)-3-hydrazinylpyrazin-2(1H)-one (300 mg, 1.28 mmol) in DCM (8 mL) was added dropwise a solution of tetrahydro-2H-pyran-4-carbonyl chloride (209 mg, 1.41 mmol) in DCM (2 mL). The mixture was warmed to room temperature and stirred for 1 h. To the mixture was added H$_2$O (5 mL). The organic layer was washed with water (10 mL), dried over Na$_2$SO$_4$ and concentrated to give crude N'-(4-(3-fluorobenzyl)-3-oxo-3,4-dihydropyrazin-2-yl)tetrahydro-2H-pyran-4-carbohydrazide 400 mg (90%) used for the next reaction without further purification.
Step 2:
To a solution of N'-(4-(3-fluorobenzyl)-3-oxo-3,4-dihydropyrazin-2-yl)tetrahydro-2H-pyran-4-carbohydrazide (400 mg, 1.16 mmol) in dioxane (10 mL) was added POCl$_3$ (884 mg, 5.78 mmol). The mixture was heated at reflux for 1.5 h and then cooled to room temperature. The reaction was concentrated in vacuo and the residue was adjusted to pH=7-8 by addition of sat. aq. NaHCO$_3$. The mixture was extracted with ethyl acetate (3×30 mL). The combined organic phases were washed with brine, dried over Na$_2$SO$_4$, filtered, concentrated in vacuo and purified by flash chromatography using a gradient of DCM/methanol (DCM/MeOH=50/1 to 20/1) to give 7-(3-fluorobenzyl)-3-(tetrahydro-2H-pyran-4-yl)-[1,2,4]triazolo[4,3-a]pyrazin-8(7H)-one 122 mg (32%). $^1$H NMR (DMSO-d$_6$ varian 400): δ57.69 (d, J=5.6 Hz, 1H), 7.41-7.36 (m, 1H), 7.28 (d, J=6.0 Hz, 1H), 7.21-7.12 (m, 3H), 5.11 (s, 2H), 3.94 (d, J=11.6 Hz, 2H), 3.52-3.46 (m, 2H), 1.87-1.81 (m, 4H). LCMS (MH+): m/z=329.1, t$_R$ (minutes, Method 3)=1.68

Example 16

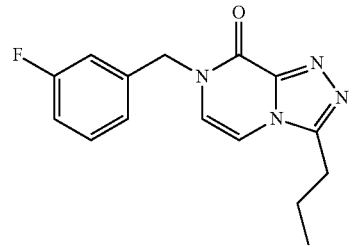 [SMILES: CCCc1nnc2c(=O)n(Cc3cccc(F)c3)ccn12]

7-(3-Fluorobenzyl)-3-propyl-[1,2,4]triazolo[4,3-a]pyrazin-8(7H)-one

Step 1:
To a solution of 2-((3-fluorobenzyl)oxy)-3-hydrazinylpyrazine (1.5 g, 6.4 mmol) in chloroform (20 ml) was added butyraldehyde (0.508 g 7.04 mmol) and the mixture was stirred for 6 hours at RT and subsequently cooled on an icebath. Iodobenzene diacetate (2.27 g, 7.04 mmol) was added and cooling removed. The reaction was stirred at RT for 16 hours. The crude reaction was concentrated onto celite and purified by flash chromatography using a gradient of ethyl acetate and heptane to yield 8-((3-fluorobenzyl)oxy)-3-propyl-[1,2,4]triazolo[4,3-a]pyrazine 1.5 g (82%).
Step 2:
To a solution of 8-((3-fluorobenzyl)oxy)-3-propyl-[1,2,4]triazolo[4,3-a]pyrazine (1.43 g, 4.99 mmol) in DME (30 ml) was added sodium iodide (1.5 g, 1.0 mmol) and the reaction was heated at 200° C. for 20 minutes under microwave irradiation. To the reaction was added with H$_2$O (50 mL) and it was extracted with DCM (3×60 mL). The combined organic phases were washed with brine, dried over MgSO$_4$, concentrated in vacuo and purified by flash chromatography using a gradient of ethyl acetate and heptane to yield 7-(3-fluorobenzyl)-3-propyl-[1,2,4]triazolo[4,3-a]pyrazin-8 (7H)-one 1.14 g (80%). $^1$H NMR (CDCl$_3$ 500 MHz): δ7.38 (m, 1H), 7.15 (m, 1H), 7.08 (m, 2H), 6.92 (d, J=6.0 Hz, 1H), 6.66 (d, J=6.0 Hz, 1H), 5.18 (s, 2H), 2.96 (t, J=7.6 Hz, 2H), 1.91 (m, 2H), 1.08 (t, J=7.4 Hz, 3H). LCMS (MH+): m/z=287.1, $t_R$(minutes, Method 1)=0.52

Example 17

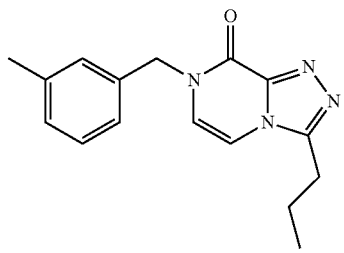 [SMILES: CCCc1nnc2c(=O)n(Cc3cccc(C)c3)ccn12]

7-(3-Methylbenzyl)-3-propyl-[1,2,4]triazolo[4,3-a]pyrazin-8(7H)-one

To a solution of 8-chloro-3-propyl-[1,2,4]triazolo[4,3-a]pyrazine (94 mg, 0.48 mmol) and m-tolylmethanol (105 mg, 0.860 mmol) in DME (3 ml) was added NaH 60% in mineral oil (34 mg, 0.86 mmol) at RT and the reaction was stirred for 1 hour.

Sodium iodide (143 mg, 0.956 mmol) was added and the reaction was heated at 200° C. for 20 minutes under microwave irradiation. The crude reaction mixture was concentrated in vacuo and purified by flash chromatography using a gradient of (petroleum ether:EtOAc:5% Et$_3$N/10% MeOH/85% EtOAc=1:0:0 to 0:1:0 to 0:0:1) to yield 44 mg 7-(3-methylbenzyl)-3-propyl-[1,2,4]triazolo[4,3-a]pyrazin-8 (7H)-one (33%). $^1$H NMR (CDCl$_3$ 500 MHz): δ7.25 (m, 1H), 7.13 (m, 3H), 6.89 (d, J=6.0 Hz, 1H), 6.64 (d, J=6.0 Hz, 1H), 5.11 (s, 2H), 2.92 (t, J=7.5 Hz, 2H), 2.33 (s, 3H), 1.89 (m, 2H), 1.02 (t, J=7.4 Hz, 3H). LCMS (MH+): m/z=283.3, $t_R$ (minutes, Method 1)=0.57

Example 18

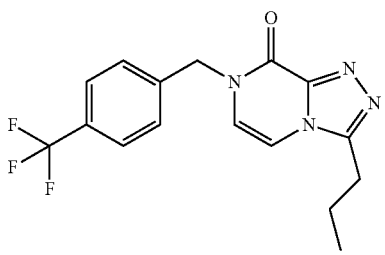 [SMILES: CCCc1nnc2c(=O)n(Cc3ccc(C(F)(F)F)cc3)ccn12]

3-Propyl-7-(4-(trifluoromethyl)benzyl)-[1,2,4]triazolo[4,3-a]pyrazin-8(7H)-one

To a solution of 8-chloro-3-propyl-[1,2,4]triazolo[4,3-a]pyrazine (82 mg, 0.42 mmol) and (4-(trifluoromethyl)phenyl)methanol (114 mg, 0.646 mmol) in DME (3.5 ml) was added NaH 60% in mineral oil (47 mg, 1.2 mmol) at RT and the mixture was stirred for 2 hours. Sodium iodide (140 mg, 0.932 mmol) was added and the reaction was heated at 200° C. for 20 minutes under microwave irradiation. The crude reaction mixture was concentrated in vacuo and purified by flash chromatography using a gradient of (petroleum ether:EtOAc:5% Et$_3$N/10% MeOH/85% EtOAc=1:0:0 to 0:1:0 to 0:0:1) to yield 31 mg 3-propyl-7-(4-(trifluoromethyl)benzyl)-[1,2,4]triazolo[4,3-a]pyrazin-8(7H)-one (19%). $^1$H NMR (CDCl$_3$ 500 MHz): δ 7.65 (m, 2H), 7.50 (m, 2H), 6.94 (d, J=6.0 Hz, 1H), 6.65 (d, J=6.0 Hz, 1H), 5.21 (s, 2H), 2.97 (t, J=7.6 Hz, 2H), 1.91 (m, 2H), 1.07 (t, J=7.4 Hz, 3H). LCMS (MH$^+$): m/z=337.2, $t_R$ (minutes, Method 1)=0.62

Example 19

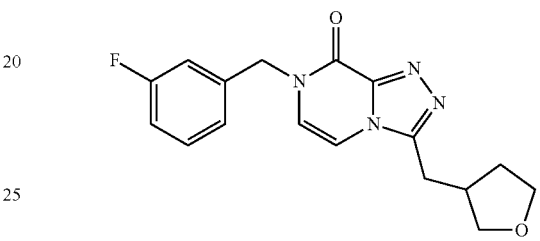

7-(3-Fluorobenzyl)-3-((tetrahydrofuran-3-yl)methyl)-[1,2,4]triazolo[4,3-a]pyrazin-8(7H)-one Step 1:

To a mixture of 2-(tetrahydrofuran-3-yl)acetic acid (1.00 g, 7.68 mmol) and SOCl$_2$ (10 ml) was added one drop of DMF and the reaction mixture was stirred at RT for 45 minutes.

The temperature was brought to 85° C. and stirred for 4 hours before being concentrated in vacuo.

The crude product was used for next step without further purification

Step 2:

To an ice-cold solution of 2-chloro-3-hydrazinylpyrazine (1.1 g, 7.7 mmol) and DIPEA (2.98 g, 23.1 mmol) in DCM (30 ml) was added 2-(tetrahydrofuran-3-yl)acetyl chloride (1.1 g, 7.7 mmol) in DCM (8.0 ml). The reaction was then allowed to warm to RT and stirred overnight.

The reaction mixture was poured into H$_2$O (100 mL) and extracted with DCM (3×50 mL). The combined organic phases were washed with brine, dried over MgSO$_4$ and concentrated in vacuo. The crude product was purified by flash chromatography using a gradient of ethyl acetate and heptane to yield N'-(3-chloropyrazin-2-yl)-2-(tetrahydrofuran-3-yl)acetohydrazide 714 mg (36%).

Step 3:

A mixture of N'-(3-chloropyrazin-2-yl)-2-(tetrahydrofuran-3-yl)acetohydrazide (200 mg, 0.779 mmol) and POCl$_3$ (597 mg, 3.90 mmol) in acetonitrile (4.5 ml) was heated for 60 min at 100° C. under microwave irradiation. To the reaction was carefully added sat. aq. K$_2$CO$_3$ (15 mL) and then H$_2$O (20 mL). The mixture was extracted with ethyl acetate (3×30 mL). The combined organic phases were washed with brine, dried over MgSO$_4$ and concentrated in vacuo. The crude product was purified by flash chromatography using a gradient of ethyl acetate and heptane to yield 8-chloro-3-((tetrahydrofuran-3-yl)methyl)-[1,2,4]triazolo[4,3-a]pyrazine 73 mg, (39%).

Step 4:

To a solution of 8-chloro-3-((tetrahydrofuran-3-yl)methyl)-[1,2,4]triazolo[4,3-a]pyrazine (72 mg, 0.30 mmol) and (3-fluorophenyl)methanol (46 mg, 0.36 mmol) dissolved in DME (2 ml) was added NaH 60% in mineral oil (22 mg, 0.54 mmol) at 0° C. The mixture was allowed to warm to RT and stirred for 3 hours. Sodium iodide (90 mg, 0.60 mmol) was added and the reaction was heated at 200° C. for 20 min under microwave irradiation. The reaction mixture was poured into H$_2$O (25 mL) and extracted with ethyl acetate (3×25 mL). The combined organic phases were washed with brine, dried over MgSO$_4$, concentrated in vacuo and purified by flash chromatography using a gradient of ethyl acetate and heptane to yield 26 mg (26%) 7-(3-fluorobenzyl)-3-((tetrahydrofuran-3-yl)methyl)-[1,2,4]triazolo[4,3-a]pyrazin-8(7H)-one. $^1$H NMR (CDCl$_3$ 600 MHz): δ7.32 (m, 1H), 7.13 (m, 1H), 7.06 (m, 2H), 7.00 (d, J=6.0 Hz, 1H), 6.72 (d, J=6.0 Hz, 1H), 5.14 (s, 2H), 3.93 (m, 2H), 3.79 (m, 1H), 3.54 (m, 1H), 3.02 (m, 2H), 2.91 (m, 1H), 2.18 (m, 1H), 1.72 (m, 1H). LCMS (MH$^+$): m/z=329.0, t$_R$ (minutes, Method 2)=0.47

Example 20

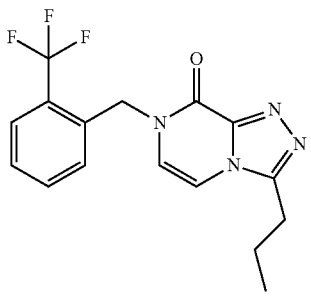 [SMILES: CCCc1nnc2c(=O)n(Cc3ccccc3C(F)(F)F)ccn12]

3-Propyl-7-(2-(trifluoromethyl)benzyl)-[1,2,4]triazolo[4,3-a]pyrazin-8(7H)-one

To a solution of 8-chloro-3-propyl-[1,2,4]triazolo[4,3-a]pyrazine (88 mg, 0.45 mmol) and (2-(trifluoromethyl)phenyl)methanol (111 mg, 0.629 mmol) in dimethoxyethane (3.5 ml) was added NaH 60% in mineral oil (35 mg, 0.88 mmol) at RT and the reaction was stirred for 2 hours. Sodium iodide (110 mg, 0.734 mmol) was added and the reaction was heated at 200° C. for 20 min under microwave irradiation. The reaction mixture was concentrated in vacuo and purified by flash chromatography using a gradient of (petroleum ether:EtOAc:5% Et$_3$N/10% MeOH/85% EtOAc=1:0:0 to 0:1:0 to 0:0:1) to yield 31 mg (17%) 3-propyl-7-(2-(trifluoromethyl)benzyl)-[1,2,4]triazolo[4,3-a]pyrazin-8(7H)-one. $^1$H NMR (CDCl$_3$ 500 MHz): δ 7.76 (m, 1H), 7.56 (m, 1H), 7.45 (m, 1H), 7.40 (m, 1H), 6.93 (d, J=6.0 Hz, 1H), 6.60 (d, J=6.0 Hz, 1H), 5.40 (s, 2H), 2.98 (t, J=7.6 Hz, 2H), 1.92 (m, 2H), 1.09 (t, J=7.4 Hz, 3H). LCMS (MH$^+$): m/z=337.2, t$_R$ (minutes, Method 1)=0.60.

Example 21

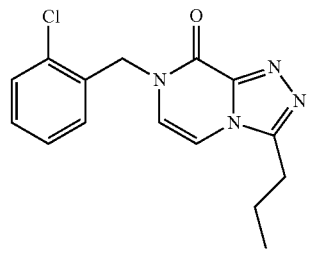 [SMILES: CCCc1nnc2c(=O)n(Cc3ccccc3Cl)ccn12]

7-(2-Chlorobenzyl)-3-propyl-[1,2,4]triazolo[4,3-a]pyrazin-8(7H)-one

To a solution of 8-chloro-3-propyl-[1,2,4]triazolo[4,3-a]pyrazine (108 mg, 0.549 mmol) and (2-chlorophenyl)methanol (153 mg, 1.07 mmol) in dimethoxyethane (3 ml) was added NaH 60% in mineral oil (40 mg, 0.99 mmol) at RT. The reaction was stirred for 2 hours. Sodium iodide (165 mg, 1.10 mmol) was added and the reaction was heated at 200° C. for 20 min under microwave irradiation. The crude mixture was concentrated in vacuo and purified by flash chromatography using a gradient of (petroleum ether:EtOAc:5% Et$_3$N/10% MeOH/85% EtOAc=1:0:0 to 0:1:0 to 0:0:1) to yield 15 mg (9%) 7-(2-chlorobenzyl)-3-propyl-[1,2,4]triazolo[4,3-a]pyrazin-8(7H)-one. $^1$H NMR (CDCl$_3$ 500 MHz): δ 7.44 (m, 2H), 7.28 (m, 2H), 6.90 (d, J=6.0 Hz, 1H), 6.76 (d, J=6.0 Hz, 1H), 5.30 (s, 2H), 2.94 (t, J=7.6 Hz, 2H), 1.88 (p, J=7.5 Hz, 2H), 1.03 (t, J=7.4 Hz, 3H). LCMS (MH$^+$): m/z=303.2, t$_R$ (minutes, Method 1)=0.56

Example 22

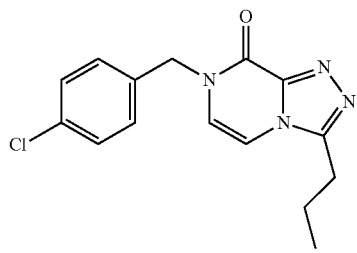 [SMILES: CCCc1nnc2c(=O)n(Cc3ccc(Cl)cc3)ccn12]

7-(4-Chlorobenzyl)-3-propyl-[1,2,4]triazolo[4,3-a]pyrazin-8(7H)-one

To an ice-cold solution of 3-propyl-[1,2,4]triazolo[4,3-a]pyrazin-8(7H)-one (201 mg, 1.13 mmol) in DMF (0.8 mL) was added sodium hydride 60% in mineral oil (122 mg, 3.05 mmol). Cooling was removed and stirring was continued for 1 hour. To the reaction was added 1-(bromomethyl)-4-chlorobenzene (624 mg, 3.04 mmol) and stirring was continued for another 3% hours. The reaction was quenched by addition of sat. aq. NH$_4$Cl (2 mL) dropwise. It was then poured into H$_2$O (20 mL) and extracted with ethyl acetate (3×20 mL). The combined organic phases were washed with brine, dried over MgSO$_4$ and concentrated in vacuo. The crude product was purified by flash chromatography using a gradient of ethyl acetate and heptane to yield 13 mg (4%) 7-(4-chlorobenzyl)-3-propyl-[1,2,4]triazolo[4,3-a]pyrazin-8(7H)-one. ¹H NMR (CDCl₃ 600 MHz): δ 7.35 (m, 2H), 7.32 (m, 2H), 6.91 (d, J=6.0 Hz, 1H), 6.61 (d, J=6.0 Hz, 1H), 5.12 (s, 2H), 2.93 (t, J=7.6 Hz, 2H), 1.89 (m, 2H), 1.04 (t, J=7.4 Hz, 3H). LCMS (MH⁺): m/z=303.2 $t_R$ (minutes, Method 1)=0.59

Example 23

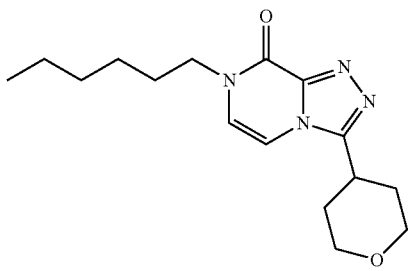 [SMILES: CCCCCCn1ccn2c(C3CCOCC3)nnc2c1=O]

7-Hexyl-3-(tetrahydro-2H-pyran-4-yl)-[1,2,4]triazolo[4,3-a]pyrazin-8(7H)-one

A solution of 3-(tetrahydro-2H-pyran-4-yl)-[1,2,4]triazolo[4,3-a]pyrazin-8(7H)-one hydrochloride (100 mg, 0.390 mmol), 1-bromohexane (148 mg, 0.898 mmol), K₂CO₃ (193 mg, 1.40 mmol) and NaI (5.84 mg, 0.039 mmol) in DMF (1.5 ml) was stirred at 80° C. over night. The reaction mixture was poured into H₂O (20 mL) and extracted with ethyl acetate (3×20 ml). The combined organic phases were washed with brine, dried over MgSO₄ and concentrated in vacuo. The residue was purified by flash chromatography on silica using a gradient of heptane, ethyl acetate and ethyl acetate+20% MeOH (Heptane/EtOAc/EtOAc+20% MeOH 1:0:0 to 0:1:0 to 0:0:1) to yield 26 mg (22%) 7-hexyl-3-(tetrahydro-2H-pyran-4-yl)-[1,2,4]triazolo[4,3-a]pyrazin-8(7H)-one. ¹H NMR (CDCl₃ 500 MHz): δ 7.02 (d, J=6.0 Hz, 1H), 6.71 (d, J=6.0 Hz, 1H), 4.13 (m, 2H), 3.96 (m, 2H), 3.61 (m, 2H), 3.23 (m, 1H), 2.21 (m, 2H), 1.96 (m, 2H), 1.77 (m, 2H), 1.35 (m, 6H), 0.91 (m, 3H). LC-MS: m/z=305.2 [M+H]⁺, $t_R$(minutes, Method 1)=0.55.

Example 24

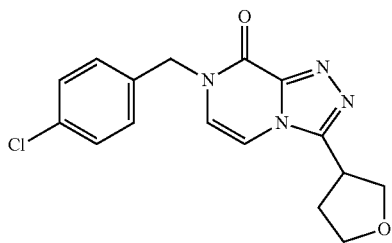 [SMILES: O=c1c2nnc(C3CCOC3)n2ccn1Cc1ccc(Cl)cc1]

7-(4-Chlorobenzyl)-3-(tetrahydrofuran-3-yl)-[1,2,4]triazolo[4,3-a]pyrazin-8(7H)-one Step 1:
To a solution of tetrahydrofuran-3-carboxylic acid (1.0 g, 8.6 mmol) in DMF (15 ml) was added HATU (3.60 g, 9.47 mmol), DIPEA (1.22 g, 1.66 ml, 9.47 mmol) and finally 2-chloro-3-hydrazinylpyrazine (1.37 g, 9.47 mmol). The mixture was stirred for 3 hours at RT. The reaction mixture was poured into sat. aq. Na₂CO₃ (20 mL) and extracted with ethyl acetate (3×20 mL). The combined organic phases were washed with brine (3×25 mL), dried over MgSO₄ and concentrated in vacuo. The crude product was purified by flash chromatography using a gradient of ethyl acetate and heptane to yield 1.1 g (53%) N'-(3-chloropyrazin-2-yl)tetrahydrofuran-3-carbohydrazide.

Step 2:
A mixture of N'-(3-chloropyrazin-2-yl)tetrahydrofuran-3-carbohydrazide (1.1 g, 4.5 mmol) and POCl₃ (20 ml) was heated at reflux for 2 hours. The reaction mixture was concentrated in vacuo and diluted with DCM (50 mL). The solution was poured onto ice-water (50 mL) and pH adjusted to basic. The phases were separated and the water phase extracted with DCM (2×50 mL). The combined organic phases were washed with brine, dried over MgSO₄, concentrated in vacuo and purified by flash chromatography using a gradient of ethyl acetate and heptane to yield 285 mg (28%) 8-chloro-3-(tetrahydrofuran-3-yl)-[1,2,4]triazolo[4,3-a]pyrazine.

Step 3:
To a solution of 8-chloro-3-(tetrahydrofuran-3-yl)-[1,2,4]triazolo[4,3-a]pyrazine (80 mg, 0.36 mmol) and (4-chlorophenyl)methanol (91 mg, 0.64 mmol) dissolved in dimethoxyethane (2.2 mL) was added NaH 60% in mineral oil (26 mg, 0.64 mmol) at RT. The reaction was stirred at RT for 2 hours. Sodium iodide (107 mg, 0.712 mmol) was added and the reaction was heated at 200° C. for 20 min under microwave irradiation. The crude reaction was poured into H₂O (25 mL) and extracted with ethyl acetate (3×25 mL). The combined organic phases were washed with brine, dried over MgSO₄ and concentrated in vacuo. The crude product was purified by flash chromatography using a gradient of ethyl acetate and heptane to yield 22 mg (19%) 7-(4-chlorobenzyl)-3-(tetrahydrofuran-3-yl)-[1,2,4]triazolo[4,3-a]pyrazin-8(7H)-one. ¹H NMR (CDCl₃ 600 MHz): δ 7.35 (m, 2H), 7.32 (m, 2H), 7.11 (d, J=6.0 Hz, 1H), 6.61 (d, J=6.0 Hz, 1H), 5.12 (m, 2H), 4.13 (m, 3H), 3.89 (m, 2H), 2.48 (m, 1H), 2.42 (m, 1H). LCMS (MH⁺): m/z=331.2 $t_R$ (minutes, Method 1)=0.53.

Example 25

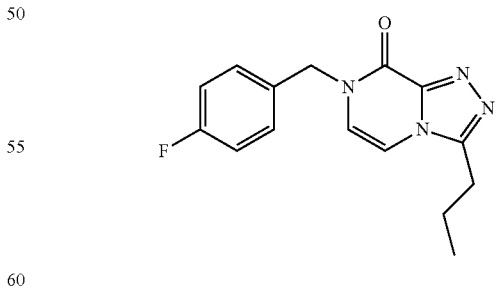

7-(4-Fluorobenzyl)-3-propyl-[1,2,4]triazolo[4,3-a]pyrazin-8(7H)-one

To a solution of 8-chloro-3-propyl-[1,2,4]triazolo[4,3-a]pyrazine (112 mg, 0.570 mmol) and (4-fluorophenyl)methanol (129 mg, 1.03 mmol) in dimethoxyethane (3.5 ml) was added NaH 60% in mineral oil (41 mg, 1.0 mmol) at RT and the mixture was stirred for 2 hours. To the reaction was added sodium iodide (171 mg, 1.14 mmol) and the reaction was heated at 200° C. for 20 min under microwave irradiation. The crude reaction was concentrated in vacuo and purified by flash chromatography using a gradient of (petroleum ether:EtOAc:5% Et$_3$N/10% MeOH/85% EtOAc=1:0:0 to 0:1:0 to 0:0:1) to yield 28 mg (16%) 7-(4-fluorobenzyl)-3-propyl-[1,2,4]triazolo[4,3-a]pyrazin-8(7H)-one. 4-chlorobenzyl)-3-(tetrahydrofuran-3-yl)-[1,2,4]triazolo[4,3-a]pyrazin-8(7H)-one. $^1$H NMR (CDCl$_3$ 500 MHz): δ 7.39 (m, 2H), 7.08 (m, 2H), 6.91 (d, J=6.0 Hz, 1H), 6.63 (d, J=6.0 Hz, 1H), 5.13 (s, 2H), 2.94 (t, J=7.6 Hz, 2H), 1.91 (m, 2H), 1.07 (t, J=7.4 Hz, 3H). (t, J=. LCMS (MH+): m/z=287.2, t$_R$ (minutes, Method 1)=0.52

Example 26

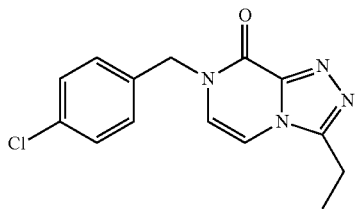 [SMILES: CCc1nnc2c(=O)n(Cc3ccc(Cl)cc3)ccn12]

7-(4-Chlorobenzyl)-3-ethyl-[1,2,4]triazolo[4,3-a]pyrazin-8(7H)-one

Step 1:
To a solution 2-chloro-3-hydrazinylpyrazine (2.00 g, 13.8 mmol) in DCM (73 ml) was added propionaldehyde (0.804 g, 13.8 mmol) and mixture was heated at reflux for 1 hour and then cooled on an ice bath.

To the cold solution was added iodobenzene diacetate (5.12 g, 15.9 mmol) and it was allowed to warm to RT overnight. The reaction was washed with H$_2$O (25 mL), then brine (25 mL) and concentrated in vacuo. The crude product was purified by flash chromatography using a gradient of ethyl acetate and heptane to yield 1.84 g (73%) 8-chloro-3-ethyl-[1,2,4]triazolo[4,3-a]pyrazine.

Step 2:
To a solution of 8-chloro-3-ethyl-[1,2,4]triazolo[4,3-a]pyrazine (101 mg, 0.553 mmol) and (4-chlorophenyl)methanol (142 mg, 0.996 mmol) in dimethoxyethane (4.5 mL) was added NaH 60% in mineral oil (40 mg, 1.0 mmol) at RT and the mixture was stirred for 2 hours. To the reaction was added sodium iodide (107 mg, 0.712 mmol) and the reaction was heated at 200° C. for 20 minutes under microwave irradiation. The reaction mixture was poured into H$_2$O (25 mL) and extracted with ethyl acetate (3×25 mL). The combined organic phases were washed with brine, dried over MgSO$_4$ and concentrated in vacuo. The crude product was purified by flash chromatography using a gradient of ethyl acetate and ethyl acetate+10% methanol to yield 21 mg (13%) yield) 7-(4-chlorobenzyl)-3-ethyl-[1,2,4]triazolo[4,3-a]pyrazin-8(7H)-one. $^1$H NMR (CDCl$_3$ 600 MHz): δ 7.36 (m, 2H), 7.31 (m, 2H), 6.91 (d, J=6.0 Hz, 1H), 6.62 (d, J=6.0 Hz, 1H), 5.13 (s, 2H), 2.96 (t, J=7.6 Hz, 2H), 1.46 (t, J=7.4 Hz, 3H). LCMS (MH$^+$): m/z=389.1, t$_R$ (minutes, Method 1)=0.53

Example 27

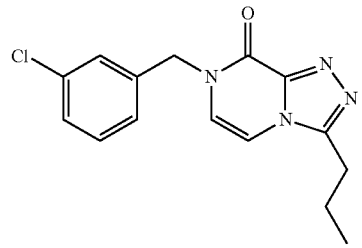 [SMILES: CCCc1nnc2c(=O)n(Cc3cccc(Cl)c3)ccn12]

7-(3-Chlorobenzyl)-3-propyl-[1,2,4]triazolo[4,3-a]pyrazin-8(7H)-one

To a solution of 8-chloro-3-propyl-[1,2,4]triazolo[4,3-a]pyrazine (97 mg, 0.49 mmol) and (3-chlorophenyl)methanol (127 mg, 0.888 mmol) in dimethoxyethane (3 ml) was added NaH 60% in mineral oil (40 mg, 1.0 mmol) at RT and the mixture was stirred for 2 hours. To the solution was added sodium iodide (148 mg, 0.987 mmol) and the reaction was heated at 200° C. for 20 min under microwave irradiation. The crude reaction was concentrated in vacuo and purified by flash chromatography using a gradient of (petroleum ether:EtOAc:5% Et$_3$N/10% MeOH/85% EtOAc=1:0:0 to 0:1:0 to 0:0:1) to yield 30 mg (20%) of 7-(3-chlorobenzyl)-3-propyl-[1,2,4]triazolo[4,3-a]pyrazin-8(7H)-one. $^1$H NMR (CDCl$_3$ 500 MHz): δ 7.32 (m, 3H), 7.22 (m, 1H), 6.92 (d, J=6.0 Hz, 1H), 6.64 (d, J=6.0 Hz, 1H), 5.11 (s, 2H), 2.93 (t, J=7.6 Hz, 2H), 1.89 (m, 2H), 1.04 (t, J=7.4 Hz, 3H). LCMS (MH$^+$): m/z=303.2, t$_R$ (minutes, Method 1)=0.58

Example 28

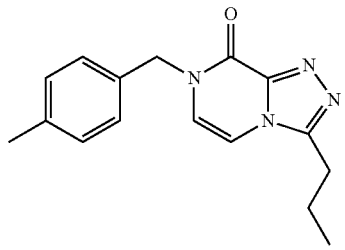 [SMILES: CCCc1nnc2c(=O)n(Cc3ccc(C)cc3)ccn12]

7-(4-Methylbenzyl)-3-propyl-[1,2,4]triazolo[4,3-a]pyrazin-8(7H)-one

A solution of 8-chloro-3-propyl-[1,2,4]triazolo[4,3-a]pyrazine (106 mg, 0.539 mmol) and 1-(bromomethyl)-4-methylbenzene (100 mg, 0.539 mmol) in DMF (2 ml) was heated at 200° C. for 20 min under microwave irradiation. The crude reaction was poured into sat. aq. NaHCO$_3$ and extracted with ethyl acetate (3×15 mL). The combined organic phases were washed with brine, dried over Na$_2$SO$_4$ and concentrated in vacuo. The crude product was purified by flash chromatography using a gradient of (petroleum ether:EtOAc:5% Et$_3$N/10% MeOH/85% EtOAc=1:0:0 to 0:0:1) to yield 24 mg (13%) 7-(4-methylbenzyl)-3-propyl-[1,2,4]triazolo[4,3-a]pyrazin-8(7H)-one. $^1$H NMR (CDCl$_3$ 500 MHz): δ 7.24 (m, 2H), 7.17 (m, 2H), 6.93 (d, J=6.0 Hz, 1H), 6.70 (d, J=6.0 Hz, 1H), 5.11 (s, 2H), 2.91 (t, J=7.6 Hz, 2H), 1.85 (m, 2H), 1.02 (t, J=7.4 Hz, 3H). LCMS (MH⁺): m/z=283.3, $t_R$ (minutes, Method 1)=0.58

Example 29

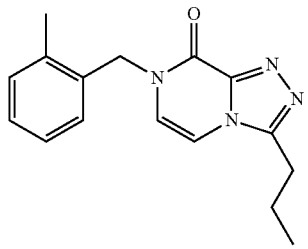 [SMILES: CCCc1nnc2c(=O)n(Cc3ccccc3C)ccn12]

7-(2-Methylbenzyl)-3-propyl-[1,2,4]triazolo[4,3-a]pyrazin-8(7H)-one

A solution of 8-chloro-3-propyl-[1,2,4]triazolo[4,3-a]pyrazine (105 mg, 0.534 mmol) and 1-(bromomethyl)-2-methylbenzene (104 mg, 0.562 mmol) in DMF (2 ml), was heated at 200° C. for 20 min under microwave irradiation. The crude reaction was poured into sat. aq. NaHCO₃ and extracted with ethyl acetate (3×10 mL). The combined organic phases were washed with brine, dried over Na₂SO₄ and concentrated in vacuo. The crude product was purified by column chromatography using a gradient of (heptane:ethyl acetate:5% Et₃N/10% MeOH/85% EtOAc=1:0:0 to 0:1:0 to 0:0:1) to yield 1.4 mg (1%) 7-(2-methylbenzyl)-3-propyl-[1,2,4]triazolo[4,3-a]pyrazin-8(7H)-one. ¹H NMR (CDCl₃ 600 MHz): δ 7.25 (m, 3H), 7.19 (m, 1H), 6.86 (d, J=6.0 Hz, 1H), 6.49 (d, J=6.0 Hz, 1H), 5.19 (s, 2H), 2.92 (t, J=7.6 Hz, 2H), 1.89 (m, 2H), 1.04 (t, J=7.4 Hz, 3H). LCMS (MH⁺): m/z=283.3, $t_R$ (minutes, Method 1)=0.56

Example 30

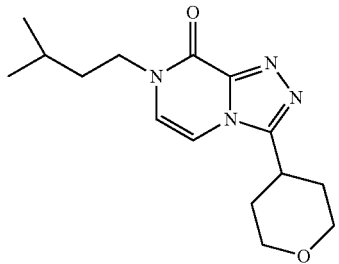 [SMILES: CC(C)CCn1ccn2c(C3CCOCC3)nnc2c1=O]

7-isopentyl-3-(tetrahydro-2H-pyran-4-yl)-[1,2,4]triazolo[4,3-a]pyrazin-8(7H)-one A solution of 3-(tetrahydro-2H-pyran-4-yl)-[1,2,4]triazolo[4,3-a]pyrazin-8(7H)-one hydrochloride (100 mg, 0.390 mmol), 1-bromo-3-methylbutane (136 mg, 112 μl, 0.898 mmol), K₂CO₃ (192 mg, 1.389 mmol) and NaI (5.84 mg, 0.039 mmol) in DMF (1.5 ml) was stirred at 80° C. overnight. The reaction mixture was poured into H₂O and extracted with ethyl acetate (3×20 ml). The combined organic phases were washed with brine, dried over MgSO₄ and concentrated in vacuo. The residue was purified by flash chromatography on silica using (Heptane/EtOAc/EtOAc+ 20% MeOH 1:0:0 to 0:1:0 to 0:0:1) to yield 31 mg (27%) 7-isopentyl-3-(tetrahydro-2H-pyran-4-yl)-[1,2,4]triazolo[4,3-a]pyrazin-8(7H)-one. ¹H NMR (CDCl₃ 500 MHz): δ 7.01 (d, J=6 Hz, 1H), 6.69 (d, J=6 Hz, 1H), 4.16 (d, J=7.6 Hz, 2H), 4.01 (m, 2H), 3.61 (m, 2H), 3.22 (m, 1H), 2.21 (m, 2H), 1.98 (m, 2H), 1.65 (m, 3H), 1.00 (m, 6H). LC-MS m/z=291.2 [M+H]⁺: $t_R$ (minutes, Method 5)=0.58.

Example 31

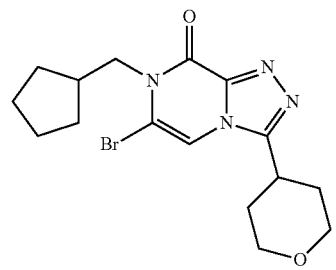 [SMILES: O=c1c2nnc(C3CCOCC3)n2cc(Br)n1CC1CCCC1]

6-bromo-7-(cyclopentylmethyl)-3-(tetrahydro-2H-pyran-4-yl)-[1,2,4]triazolo[4,3-a]pyrazin-8(7H)-one Step 1:

To a solution of 5-bromo-3-chloro-2-hydrazinylpyrazine (44.50 g, 199.14 mmol) in DCM (500 mL) was added tetrahydro-2H-pyran-4-carbaldehyde (23.87 g, 209.10 mmol). The mixture was stirred at 30° C. for 1.5 h. LCMS showed the reaction was completed. The mixture was directly used for the next step as a brown liquid. Then it was cooled to 0° C., PhI(OAc)₂ (73.76 g, 229.01 mmol) was added in portions. After addition, the mixture was stirred at 30° C. for 2 h. LCMS showed the reaction was completed. Sat. aq. K₂CO₃ (100 mL) was added to the mixture slowly and it was stirred for 10 min. The organic phase was separated and washed with brine, dried over Na₂SO₄, filtered and concentrated to give the crude product. The crude product was washed with MTBE (100 mL) and DCM (200 mL) to give 6-bromo-8-chloro-3-(tetrahydro-2H-pyran-4-yl)-[1,2,4]triazolo[4,3-a]pyrazine (48.00 g, 75.90% yield).

Step 2:

To a solution of 6-bromo-8-chloro-3-(tetrahydro-2H-pyran-4-yl)-[1,2,4]triazolo[4,3-a]pyrazine (20.0 g, 62.98 mmol) in THF (300 mL) and H₂O (60 mL) was added NaOH (5.04 g, 125.96 mmol). The mixture was heated at 70° C. for 2 h. LCMS showed the reaction was completed. The mixture was cooled to 28° C. and acidified to pH 5-6 by 1 N HCl. The mixture was filtered and the filter cake was washed with water (200 mL) and dried in vacuo to give 6-bromo-3-(tetrahydro-2H-pyran-4-yl)-[1,2,4]triazolo[4,3-a]pyrazin-8-ol (15.00 g, 79.62% yield).

Step 3:

To a suspension of 6-bromo-3-(tetrahydro-2H-pyran-4-yl)-[1,2,4]triazolo[4,3-a]pyrazin-8-ol (4.0 g, 13.37 mmol) in DMF (40 mL) was added (bromomethyl)cyclopentane (2.62 g, 16.04 mmol) and K₂CO₃ (2.77 g, 20.06 mmol). The mixture was heated at 80° C. for 24 h. The mixture was concentrated and the residue was dissolved in DCM (50 mL) and H₂O (50 mL). The organic layer was washed with H₂O (50 mL), dried over Na₂SO₄, filtered and concentrated to give the crude product. The residue was purified by re-crystallization from DCM (50 mL) and EA (30 mL) to give 6-bromo-7-(cyclopentylmethyl)-3-(tetrahydro-2H-pyran-4-yl)-[1,2,4]triazolo[4,3-a]pyrazin-8(7H)-one (1.20 g, 23.54% yield). ¹H NMR (CDCl3 400 MHz): δ7.20 (s, 1H), 4.24 (d, J=7.6 Hz, 2H), 4.16-4.12 (m, 2H), 3.63-3.57 (m, 2H), 3.19-3.10 (m, 1H), 2.45-2.35 (m, 1H), 2.21-2.18 (m, 2H), 1.98-1.95 (m, 2H), 1.73-1.70 (m, 4H), 1.62-1.55 (m, 2H), 1.44-1.31 (m, 2H). LC-MS: $t_R$=2.54 min (METHOD 3), m/z=381.0 [M+H]⁺.

Example 32

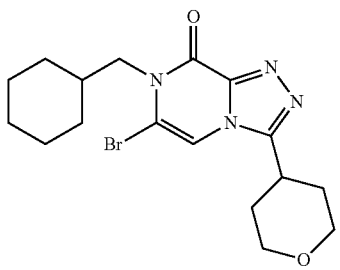 [SMILES: O=c1c2nnc(C3CCOCC3)n2cc(Br)n1CC1CCCCC1]

6-bromo-7-(cyclohexylmethyl)-3-(tetrahydro-2H-pyran-4-yl)-[1,2,4]triazolo[4,3-a]pyrazin-8(7H)-one To a suspension of 6-bromo-3-(tetrahydro-2H-pyran-4-yl)-[1,2,4]triazolo[4,3-a]pyrazin-8-ol (5.0 g, 16.72 mmol) in DMSO (50 mL) was added (bromomethyl)cyclohexane (3.55 g, 20.06 mmol) and $K_2CO_3$ (3.47 g, 25.07 mmol). The mixture was heated at 80° C. for 12 h. LCMS showed 40% of desired product. The mixture was cooled to 28° C. and water (50 mL) was added. The aqueous layer was extracted with DCM (100 mL, two times). The combined organics were washed with water (100 mL, two times, two times), dried over $Na_2SO_4$, filtered, concentrated and purified by flash chromatography on silica gel (DCM/MeOH=100/1-20/1) to give 6-bromo-7-(cyclohexylmethyl)-3-(tetrahydro-2H-pyran-4-yl)-[1,2,4]triazolo[4,3-a]pyrazin-8(7H)-one (1.90 g, 28.75% yield). ¹H NMR (CDCl₃ 400 MHz): δ 7.19 (s, 1H), 4.17-4.10 (m, 4H), 3.63-3.57 (m, 2H), 3.19-3.16 (m, 1H), 2.22-2.18 (m, 2H), 1.98-1.94 (m, 2H), 1.90-1.82 (m, 1H), 1.73-1.70 (m, 2H), 1.66-1.61 (m, 3H), 1.19-1.10 (m, 5H). LC-MS: $t_R$=2.66 min (METHOD 3), m/z=395.1 [M+H]⁺.

Example 33

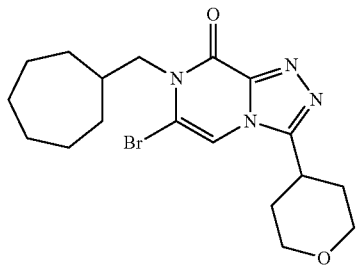 [SMILES: O=c1c2nnc(C3CCOCC3)n2cc(Br)n1CC1CCCCCC1]

6-bromo-7-(cycloheptylmethyl)-3-(tetrahydro-2H-pyran-4-yl)-[1,2,4]triazolo[4,3-a]pyrazin-8(7H)-one Step 1:
BH₃.THF (1 M, 98.45 mL, 98.45 mmol) was added dropwise to a solution of cycloheptanecarboxylic acid (7.0 g, 49.23 mmol) in THF (50 mL) at 0° C. Then the mixture was heated at 70° C. for 12 h. The reaction was checked by TLC. The mixture was cooled to 0° C. and MeOH (50 mL) was added dropwise to the mixture. The mixture was concentrated and the residue was purified by flash chromatography on silica gel (PE/EA=20/1-3/1) to give cycloheptylmethanol (6.0 g, 95.06% yield).

Step 2:
To a cooled (0° C.) solution of cycloheptylmethanol (4.00 g, 31.20 mmol) in DCM (40 mL) was added TEA (6.31 g, 62.40 mmol) and methane sulfonylchloride (9.28 g, 81.01 mmol) dropwise. The mixture was stirred at 0° C. for 1 h. TLC showed the reaction was completed. Water (20 mL) was added to the mixture. The organic layer was dried over Na₂SO4, filtered and concentrated to give cycloheptylmethyl methanesulfonate (6.00 g, 93.22% yield).

Step 3:
To a suspension of 6-bromo-3-(tetrahydro-2H-pyran-4-yl)-[1,2,4]triazolo[4,3-a]pyrazin-8-ol (5.0 g, 16.72 mmol) in anhydrous DMF (50 mL) was added cycloheptylmethyl methanesulfonate (4.48 g, 21.74 mmol) and CsF (5.08 g, 33.44 mmol). The mixture was heated at 80° C. for 12 h. LCMS showed 21% of desired product. The mixture was concentrated and the residue was dissolved in DCM (50 mL) and H₂O (30 mL). The aqueous layer was extracted with DCM (50 mL). The organic layer was washed with H₂O (30 mL), dried over Na₂SO₄, filtered, concentrated and purified by flash chromatography on silica gel (DCM/MeOH=100/1-20/1) and further purified by preparative HPLC (base) to give 6-bromo-7-(cycloheptylmethyl)-3-(tetrahydro-2H-pyran-4-yl)-[1,2,4]triazolo[4,3-a]pyrazin-8(7H)-one (465.00 mg, 6.79% yield). ¹H NMR (CDCl3 400 MHz): δ 7.20 (s, 1H), 4.15-4.09 (m, 4H), 3.63-3.57 (m, 2H), 3.19-3.17 (m, 1H), 2.21-2.02 (m, 3H), 1.97-1.94 (m, 2H), 1.75-1.65 (m, 4H), 1.60-1.45 (m, 4H), 1.44-1.27 (m, 4H). LC-MS: $t_R$=2.81 min (METHOD 3), m/z=409.1 [M+H]⁺.

Example 34

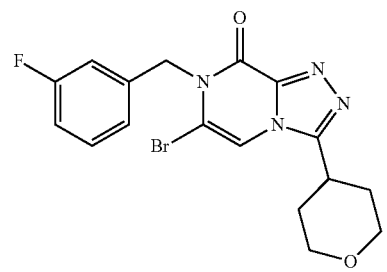 [SMILES: O=c1c2nnc(C3CCOCC3)n2cc(Br)n1Cc1cccc(F)c1]

6-bromo-7-(3-fluorobenzyl)-3-(tetrahydro-2H-pyran-4-yl)-[1,2,4]triazolo[4,3-a]pyrazin-8(7H)-one To a suspension of 6-bromo-3-(tetrahydro-2H-pyran-4-yl)-[1,2,4]triazolo[4,3-a]pyrazin-8-ol (5.00 g, 16.72 mmol) in DMF (2 mL) was added 1-(bromomethyl)-3-fluorobenzene (3.79 g, 20.06 mmol) and K₂CO₃ (3.47 g, 25.07 mmol).

The mixture was heated at 60° C. for 12 h. The mixture was concentrated and the residue was dissolved in DCM (50 mL) and H$_2$O (50 mL). The organic layer was washed with H$_2$O (50 mL), dried over Na$_2$SO$_4$, filtered and concentrated and purified by flash chromatography on silica gel (DCM/MeOH=100/1-20/1) to give 6-bromo-7-(3-fluorobenzyl)-3-(tetrahydro-2H-pyran-4-yl)-[1,2,4]triazolo[4,3-a]pyrazin-8(7H)-one (3.90 g, 57.28% yield). $^1$H NMR (CDCl3 varian 400): δ 7.30-7.26 (m, 1H), 7.22 (s, 1H), 7.13 (d, J=8.0 Hz, 1H), 7.04-6.99 (m, 2H), 5.45 (s, 2H), 4.14-4.11 (m, 2H), 3.61-3.55 (m, 2H), 3.21-3.16 (m, 1H), 2.22-2.13 (m, 2H), 1.96-1.93 (m, 2H). LC-MS: $t_R$=2.42 min (METHOD 3), m/z=407.0 [M+H]$^+$.

Example 35

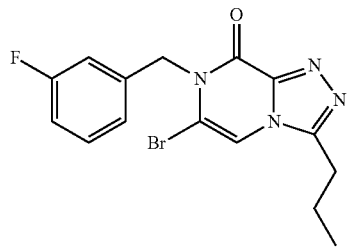 [SMILES: CCCc1nnc2c(=O)n(Cc3cccc(F)c3)c(Br)cn12]

6-bromo-7-(3-fluorobenzyl)-3-propyl-[1,2,4]triazolo[4,3-a]pyrazin-8(7H)-one

Step 1:
To a solution of 2,3-dichloropyrazine (150 g, 1.01 mol) in EtOH (700 mL) was added hydrazine monohydrate (124.53 g, 2.11 mmol, 85% in water). The reaction mixture was heated under reflux overnight. The reaction mixture was cooled and the precipitate was filtered. The resulting solid was washed with water (100 mL, two times), then cold EtOH (150 ml, two times) and dried under reduced pressure to give the 2-chloro-3-hydrazinylpyrazine (140 g, yield 96%).

Step 2:
To a suspension of 2-chloro-3-hydrazinylpyrazine (156.5 g, 1.05 mol) in THF (1.2 L) cooled at 0° C. was added dropwise a solution of TFAA (295.6 g, 1.41 mol) in THF (0.3 L). The reaction mixture was stirred at room temperature overnight and then poured into H$_2$O (500 mL). The organic phase was separated and the aqueous phase was extracted with EtOAc (500 mL*3). The combined organic phases were washed with brine, dried over MgSO$_4$ and concentrated under reduced pressure to give the N'-(3-chloropyrazin-2-yl)-2,2,2-trifluoroacetohydrazide (300 g, purity 85%, yield 98%).

Step 3:
To a suspension of N'-(3-chloropyrazin-2-yl)-2,2,2-trifluoroacetohydrazide (150 g, purity 85%, 0.53 mol) in DCM (1.5 L) was added NBS (141.5 g, 0.79 mol) in portions. After the addition, the mixture was stirred at room temperature for 2 hr. The reaction mixture was concentrated under vacuum. The residue was purified by flash chromatography on silica gel (PE/EtOAc=5/1-3/1) to give the N'-(5-bromo-3-chloropyrazin-2-yl)-2,2,2-trifluoroacetohydrazide (80 g, purity 75%, yield 94%) as a black solid.

Step 4:
To a solution of N'-(5-bromo-3-chloropyrazin-2-yl)-2,2,2-trifluoroacetohydrazide (150 g, purity 75%, 0.35 mol) in EtOH (1.2 L) was added 12N HCl (100 mL) dropwise. The solution was stirred under reflux for 6 h. The solution was cooled to room temperature and concentrated under reduced pressure. Water (300 mL) was added to the flask and it was treated with sat. NaHCO$_3$ until pH=8 (slow addition). The solution was extracted with EtOAc (500 mL*3). The combined organic phases were dried over Na$_2$SO$_4$, filtered, and concentrated under reduced pressure. The residue was purified by silica gel chromatography (PE/EA=2:1) to give 5-bromo-3-chloro-2-hydrazinylpyrazine (75 g, 95% yield) as a tan powder. $^1$H NMR (DMSO-d6 varian 400 MHz): δ 8.55 (s, 1H), 8.24 (s, 1H), 4.40 (s, 2H). LC-MS: $t_R$=1.74 min (METHOD 3), m/z=224.9 [M+H]$^+$ Step 5:
To a mixture of 5-bromo-3-chloro-2-hydrazinylpyrazine (25.0 g, 0.11 mol) in DCM (600 mL) was added butanal (8.47 g, 0.12 mol) in one portion at room temperature. The mixture was stirred at room temperature for 1.5 h. Then it was cooled to 0° C., PhI(OAc)$_2$ (37.9 g, 0.12 mol) was added in portions. After the addition, the reaction mixture was stirred at room temperature for another 1.5 h. Sat K$_2$CO$_3$(aq) (50 mL) was poured into the reaction mixture and stirred for 10 min. The organic phase was separated and washed with brine, dried over Na$_2$SO$_4$, filtered and evaporated. The residue was purified by silica gel chromatography (PE/EA=2:1) to afford 6-bromo-8-chloro-3-propyl-[1,2,4]triazolo[4,3-a]pyrazine (22.00 g, 71% yield).

Step 6:
To a mixture of 6-bromo-8-chloro-3-propyl-[1,2,4]triazolo[4,3-a]pyrazine (12.0 g, 43.6 mmol) in THF (150 mL) and H$_2$O (30 mL), was added NaOH (3.5 g, 87.1 mmol) in one portion at room temperature. The mixture was stirred at 70° C. for 2.5 h.

The mixture was adjusted to pH=5-6 by 1N HCl(aq), and concentrated under reduced pressure. The residue was dissolved in MeOH (20 mL) and filtered. The filtrate was concentrated in vacuo to afford 6-bromo-3-propyl-[1,2,4]triazolo[4,3-a]pyrazin-8-ol (11.0 g, 98% yield).

Step 7:
To a suspension of 6-bromo-3-propyl-[1,2,4]triazolo[4,3-a]pyrazin-8-ol (550 mg, 2.1 mmol) and 1-(bromomethyl)-3-fluoro-benzene (485 mg, 2.57 mmol) in DMF (8 mL), was added K$_2$CO$_3$ (443.6 mg, 3.2 mmol) in one portion at room temperature. The mixture was stirred at 60° C. for 3 h. And then the mixture was concentrated under reduced pressure. The residue diluted with water (30 mL) and extracted with DCM (70 mL, two times). The combined organic phase was washed with saturated brine, dried over anhydrous Na$_2$SO$_4$, filtered and concentrated in vacuo. The residue was purified by silica gel chromatography (PE/EA=1:1-1:3) to afford 6-bromo-7-(3-fluorobenzyl)-3-propyl-[1,2,4]triazolo[4,3-a]pyrazin-8(7H)-one (380.00 mg, 49% yield) as yellow solid. $^1$H NMR (DMSO-d6 varian 400 MHz): δ 8.09 (s, 1H), 7.42-7.37 (m, 1H), 7.19-7.10 (m, 3H), 5.38 (s, 2H), 2.97 (t, J=7.6 Hz, 2H), 1.79-1.73 (m, 2H), 0.98 (t, J=7.2 Hz, 3H). LC-MS: $t_R$=2.62 min (METHOD 3), m/z=365.0 [M+H]$^+$.

Example 36

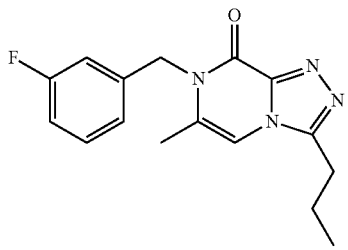 [SMILES: CCCc1nnc2c(=O)n(Cc3cccc(F)c3)c(C)cn12]

7-(3-fluorobenzyl)-6-methyl-3-propyl-[1,2,4]triazolo[4,3-a]pyrazin-8(7H)-one

To a mixture of 6-bromo-7-(3-fluorobenzyl)-3-propyl-[1,2,4]triazolo[4,3-a]pyrazin-8(7H)-one (300 mg, 0.82 mmol) and [trifluoro(methyl)-boranyl]potassium(1+) (501 mg, 4.1 mmol) in dioxane (5 mL), was added 1,1'-Bis(diphenylphosphino)ferrocene-palladium(II)dichloride (60 mg, 0.08 mmol) and $K_2CO_3$ (681 mg, 4.9 mmol) at room temperature under $N_2$. The mixture was stirred at 80° C. for 12 h. The mixture was concentrated and diluted with water, extracted EtOAc (30 mL, two times, two times). The combined organic layer was washed with brine, concentrated in vacuo and the residue was purified by preparative HPLC to give 7-(3-fluorobenzyl)-6-methyl-3-propyl-[1,2,4]triazolo[4,3-a]pyrazin-8(7H)-one (20 mg, 8% yield) as a gray solid. $^1$H NMR (CDCl$_3$ varian 400 MHz): δ7.26-7.19 (m, 1H), 6.94-6.83 (m, 3H), 6.70 (s, 1H), 5.24 (s, 2H), 2.88 (t, J=8.0 Hz, 2H), 2.18 (s, 3H), 1.89-1.80 (m, 2H), 0.99 (t, J=7.2 Hz, 3H). LC-MS: $t_R$=2.47 min (METHOD 3), m/z=301.1 [M+H]$^+$.

Example 37

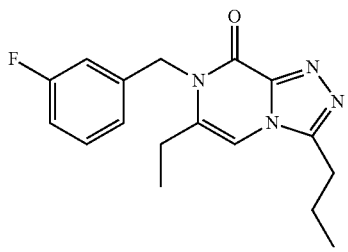 [SMILES: CCCc1nnc2c(=O)n(Cc3cccc(F)c3)c(CC)cn12]

6-ethyl-7-(3-fluorobenzyl)-3-propyl-[1,2,4]triazolo[4,3-a]pyrazin-8(7H)-one

Step 1:

To a mixture of 6-bromo-7-(3-fluorobenzyl)-3-propyl-[1,2,4]triazolo[4,3-a]pyrazin-8(7H)-one (300 mg, 0.82 mmol) and 4,4,5,5-tetramethyl-2-vinyl-1,3,2-dioxaborolane (190 mg, 1.2 mmol) in THF (5 mL) was added $K_2CO_3$ (227 mg, 1.64 mmol) and 1,1'-Bis(diphenylphosphino)ferrocene-palladium(II)dichloride (60 mg, 82.2 micromol) in at room temperature under $N_2$. The mixture was stirred at 70° C. for 12 h. Then the mixture was cooled and water (10 mL) was added. Then it was extracted with EtOAc (30 mL, two times). The combined organic layer was washed with brine (20 mL), dried over Na$_2$SO$_4$ and concentrated in vacuo. The residue was purified by silica gel chromatography (petroleums ether:ethylaacetate=1:1-1:2) to afford 7-(3-fluorobenzyl)-3-propyl-6-vinyl-[1,2,4]triazolo[4,3-a]pyrazin-8(7H)-one (150 mg, 57% yield).

Step 2:

To a solution of 7-(3-fluorobenzyl)-3-propyl-6-vinyl-[1,2,4]triazolo[4,3-a]pyrazin-8(7H)-one (150 mg, 0.48 mmol) in MeOH (4 mL) was added Pd/C (wet, 10% Pd with 50% water, 0.1 g). The suspension was degassed under vacuum and purged with H$_2$ several times. The mixture was stirred under H$_2$ (15 psi) at room temperature for 10 min. The reaction mixture was filtered and the filtrate was concentrated. The crude product was purified by silica gel chromatography (DCM/MeOH=50:1) to give 6-ethyl-7-(3-fluorobenzyl)-3-propyl-[1,2,4]triazolo[4,3-a]pyrazin-8(7H)-one (80 mg, 53% yield). $^1$H NMR (CDCl$_3$ varian 400 MHz): δ 7.29-7.26 (m, 1H), 6.97-6.86 (m, 3H), 6.72 (s, 1H), 5.32 (s, 2H), 2.96 (t, J=7.6 Hz, 2H), 2.60-2.54 (m, 2H), 1.95-1.88 (m, 2H), 1.26 (t, J=6.8 Hz, 3H), 1.07 (t, J=7.2 Hz, 3H). LC-MS: $t_R$=2.60 min (METHOD 3), m/z=315.1 [M+H]$^+$.

Example 38

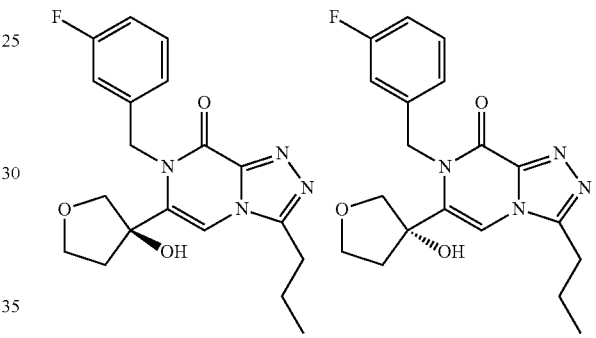

7-(3-fluorobenzyl)-6-(3-hydroxytetrahydrofuran-3-yl)-3-propyl-[1,2,4]triazolo[4,3-a]pyrazin-8(7H)-one, stereoisomer 1 and 2

Step 1:

To a suspension of 6-bromo-8-chloro-3-propyl-[1,2,4]triazolo[4,3-a]pyrazine (9.0 g, 32.7 mmol) in MeOH (100 mL) was added sodium methoxide (3.53 g, 65.3 mmol) in one portion at room temperature under $N_2$. The mixture was stirred at 60° C. for 4 hr. The mixture was concentrated under reduced pressure. The residue was suspended in DCM (100 mL), washed with water (20 mL), saturated brine (20 mL), dried with anhydrous Na$_2$SO$_4$ and concentrated in vacuo. The residue was purified by silica gel chromatography (eluent Petroleum ether/Ethyl acetate=3:1) to afford 6-bromo-8-methoxy-3-propyl-[1,2,4]triazolo[4,3-a]pyrazine (7.40 g, 84% yield).

Step 2:

To a light yellow solution of 6-bromo-8-methoxy-3-propyl-[1,2,4]triazolo[4,3-a]pyrazine (2.0 g, 7.4 mmol) in THF (20 mL), was added i-PrMgCl—LiCl (17.02 mL, 22.1 mmol, 1.3 M) dropwise at 0° C. under $N_2$. After the addition, the red solution was stirred at 0° C. for 30 min. Then dihydrofuran-3(2H)-one (1.91 g, 22.1 mmol) was added as a solution in THF (2 mL) and stirred for 1 hr at 0° C. The mixture was quenched with sat NH$_4$Cl(aq) and extracted with EtOAc twice. The combined organic layer was washed with brine and concentrated, the residue was purified by silica gel chromatography (PE:EA=1:1-1:5) to afford 3-(8-methoxy-3-propyl-[1,2,4]triazolo[4,3-a]pyrazin-6-yl)tetrahydrofuran-3-ol (250 mg, 12% yield).

Step 3:

To a solution of 3-(8-methoxy-3-propyl-[1,2,4]triazolo[4,3-a]pyrazin-6-yl)tetrahydrofuran-3-ol (440 mg, 1.6 mmol) in MeOH (8 mL), was added 2 M HCl(aq) (8 mL) in one portion at room temperature. The solution was stirred at 50° C. for 20 hr. The mixture was concentrated under reduced pressure at 50° C. The residue was purified by silica gel chromatography (DCM:MeOH=10:1) to give 6-(3-hydroxytetrahydrofuran-3-yl)-3-propyl-[1,2,4]triazolo[4,3-a]pyrazin-8-ol (270 mg, 65% yield) as yellow solid.

Step 4:

To a solution of 6-(3-hydroxytetrahydrofuran-3-yl)-3-propyl-[1,2,4]triazolo[4,3-a]pyrazin-8-ol (250 mg, 0.95 mmol) and 1-(bromomethyl)-3-fluoro-benzene (214.6 mg, 1.14 mmol) in DMF (2 mL), was added $K_2CO_3$ (261 mg, 1.89 mmol) in one portion. The suspension was stirred at 60° C. for 4 hr. The mixture was concentrated under reduced pressure. The residue was diluted with EtOAc (20 mL), washed with water (10 mL), saturated brine (5 mL), dried with anhydrous $Na_2SO_4$, filtered and concentrated in vacuum. The residue was purified by preparative HPLC to afford 7-(3-fluorobenzyl)-6-(3-hydroxytetrahydrofuran-3-yl)-3-propyl-[1,2,4]triazolo[4,3-a]pyrazin-8(7H)-one (40 mg, 11% yield).

Step 5:

7-(3-fluorobenzyl)-6-(3-hydroxytetrahydrofuran-3-yl)-3-propyl-[1,2,4]triazolo[4,3-a]pyrazin-8(7H)-one (50 mg, 134.3 micromol) was purified by SFC to afford 7-(3-fluorobenzyl)-6-(3-hydroxytetrahydrofuran-3-yl)-3-propyl-[1,2,4]triazolo[4,3-a]pyrazin-8(7H)-one, stereoisomer 1 (27 mg, 54% yield). $^1$H NMR (CDCl$_3$ varian 400): δ 7.75 (s, 1H), 7.28-7.15 (m, 3H), 6.97-6.95 (m, 1H), 5.53 (s, 2H), 4.17-4.13 (m, 1H), 4.07-4.04 (m, 1H), 3.93 (d, J=9.6 Hz, 1H), 3.76 (d, J=9.6 Hz, 1H), 2.98 (t, J=7.6 Hz, 2H), 2.68 (brs, 1H), 2.53-2.50 (m, 1H), 2.08-2.05 (m, 1H), 1.88-1.82 (m, 2H), 0.99 (t, J=7.2 Hz, 3H). LC-MS: $t_R$=2.48 min (METHOD 3), m/z=373.1 [M+H]$^+$. SFC-MS: $t_R$=8.05 min, ee %=100.00%, $[α]D^{20}$=−58.67° (c=0.10, MeOH).

And 7-(3-fluorobenzyl)-6-(3-hydroxytetrahydrofuran-3-yl)-3-propyl-[1,2,4]triazolo[4,3-a]pyrazin-8(7H)-one, stereoisomer 2 (17 mg, 34% yield) as white solid. $^1$H NMR (CDCl$_3$ varian 400): δ 7.82 (s, 1H), 7.33-7.23 (m, 3H), 7.21-7.00 (m, 1H), 5.58 (s, 2H), 4.22-4.19 (m, 1H), 4.12-4.09 (m, 1H), 3.99 (d, J=9.6 Hz, 1H), 3.82 (d, J=9.6 Hz, 1H), 3.04 (t, J=7.6 Hz, 2H), 2.83 (s, 1H), 2.58-2.55 (m, 1H), 2.08-2.05 (m, 1H), 1.93-1.88 (m, 2H), 1.04 (t, J=7.2 Hz, 3H). LC-MS: $t_R$=2.47 min (METHOD 3), m/z=373.1 [M+H]$^+$. SFC-MS: $t_R$=8.39 min, ee %=92.28%, $[α]D^{20}$=+52.67 (c=0.10, MeOH).

Example 39

7-(3-fluorobenzyl)-3-propyl-6-(tetrahydrofuran-3-yl)-[1,2,4]triazolo[4,3-a]pyrazin-8(7H)-one, stereoisomer 1 and 2

Step 1:

To a mixture of 6-bromo-7-(3-fluorobenzyl)-3-propyl-[1,2,4]triazolo[4,3-a]pyrazin-8(7H)-one (300 mg, 821.5 micromol) and 2-(2,5-dihydrofuran-3-yl)-4,4,5,5-tetramethyl-1,3,2-dioxaborolane (242 mg, 1.23 mmol) in dioxane (4 mL) and $H_2O$ (2 mL), was added $K_2CO_3$ (227 mg, 1.64 mmol) and 1,1'-Bis(diphenylphosphino)ferrocene-palladium(II)dichloride (60 mg, 82.2 micromol) in one portion. The mixture was stirred at 70-80° C. for 16 h. The mixture was concentrated under reduced pressure. The residue was diluted with EtOAc (20 mL), washed with water (10 mL), saturated brine (10 mL), dried over anhydrous $Na_2SO_4$, filtered and concentrated in vacuum. The residue was purified by silica gel chromatography (DCM/MeOH=20/1) to afford 6-(2,5-dihydrofuran-3-yl)-7-(3-fluorobenzyl)-3-propyl-[1,2,4]triazolo[4,3-a]pyrazin-8(7H)-one (260 mg, 76% yield, 85% purity) as yellow solid.

Step 2:

To a solution of 6-(2,5-dihydrofuran-3-yl)-7-(3-fluorobenzyl)-3-propyl-[1,2,4]triazolo[4,3-a]pyrazin-8(7H)-one (340 mg, 959.4 micromol) in MeOH (2 mL), was added Pd/C (50 mg, wet, 10% Pd with 50% of water) in one portion. The mixture was stirred at room temperature for 1 hr. The mixture was filtered and the filtrate was concentrated in vacuum. The residue was purified by preparative HPLC to afford 7-(3-fluorobenzyl)-3-propyl-6-(tetrahydrofuran-3-yl)-[1,2,4]triazolo[4,3-a]pyrazin-8(7H)-one (60 mg, 17% yield).

Step 3:

7-(3-fluorobenzyl)-3-propyl-6-(tetrahydrofuran-3-yl)-[1,2,4]triazolo[4,3-a]pyrazin-8(7H)-one (60 mg, 168.34 micromol) was purified by Chiral SFC to afford 7-(3-fluorobenzyl)-3-propyl-6-(tetrahydrofuran-3-yl)-[1,2,4]triazolo[4,3-a]pyrazin-8(7H)-one, stereoisomer 1 (10 mg, 17% yield). $^1$H NMR (CDCl$_3$ varian 400): δ 7.26-7.20 (m, 1H), 6.93-6.87 (m, 3H), 6.80 (d, J=9.6 Hz, 1H), 5.54 (d, J=13.6 Hz, 1H), 5.10 (d, J=14.4 Hz, 1H), 3.96-3.94 (m, 1H), 3.86-3.76 (m, 3H), 3.28-3.24 (m, 1H), 2.89 (t, J=7.6 Hz, 2H), 2.26-2.21 (m, 1H), 1.88-1.83 (m, 3H), 1.01 (t, J=7.6 Hz, 3H). LC-MS: $t_R$=2.44 min (METHOD 3), m/z=357.1 [M+H]$^+$. SFC-MS: $t_R$=7.91 min, ee %=100%.

And 7-(3-fluorobenzyl)-3-propyl-6-(tetrahydrofuran-3-yl)-[1,2,4]triazolo[4,3-a]pyrazin-8(7H)-one, stereoisomer 2 (9 mg, 14% yield) as white solid. $^1$H NMR (CDCl$_3$ varian 400): δ 7.33-7.30 (m, 1H), 7.01-6.87 (m, 4H), 5.70-5.55 (brs, 1H), 5.25-5.10 (brs, 1H), 4.03-4.02 (m, 1H), 3.93-3.84 (m, 3H), 3.33 (brs, 1H), 2.97 (t, J=7.6 Hz, 2H), 2.33-2.28 (m, 1H), 1.95-1.92 (m, 3H), 1.08 (t, J=7.6 Hz, 3H). LC-MS: $t_R$=2.43 min (METHOD 3), m/z=357.1 [M+H]$^+$. SFC-MS: $t_R$=8.46 min, ee %=97.35%.

Example 40

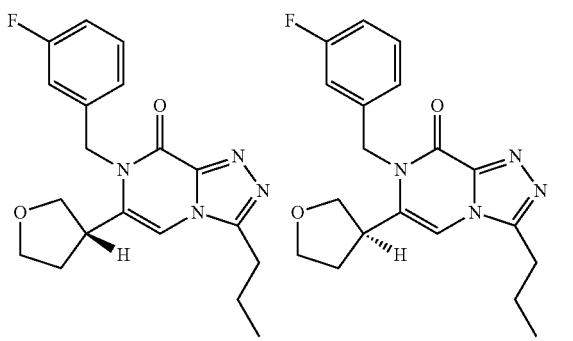

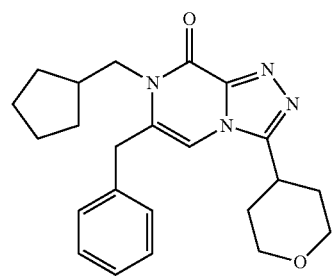 [SMILES: O=c1c2nnc(C3CCOCC3)n2cc(Cc2ccccc2)n1CC1CCCC1]

6-benzyl-7-(cyclopentylmethyl)-3-(tetrahydro-2H-pyran-4-yl)-[1,2,4]triazolo[4,3-a]pyrazin-8(7H)-one Step 1:

To a suspension of 6-bromo-3-(tetrahydro-2H-pyran-4-yl)-[1,2,4]triazolo[4,3-a]pyrazin-8(7H)-one (500 mg, 1.67 mmol) in dioxane (10 mL) and H$_2$O (5 mL) was added 2-benzyl-4,4,5,5-tetramethyl-1,3,2-dioxaborolane (547 mg, 2.51 mmol), Cs$_2$CO$_3$ (1.09 g, 3.34 mmol) and 1,1'-Bis(diphenylphosphino)ferrocene-palladium(II)dichloride (122 mg, 167.16 micromol,). The mixture was degassed with N$_2$ and heated at 100° C. for 12 h under N$_2$. LCMS showed the reaction was completed. The mixture was cooled to 25° C. and extracted with EA (20 mL, two times, two times). The organic layer was washed with water (20 mL), dried over Na$_2$SO$_4$, filtered, concentrated and purified by flash chromatography on silica gel (DCM/MeOH=100/1-20/1) to give 6-benzyl-3-(tetrahydro-2H-pyran-4-yl)-[1,2,4]triazolo[4,3-a]pyrazin-8(7H)-one (230 mg, 41.05% yield).

Step 2:

To a suspension of 6-benzyl-3-(tetrahydro-2H-pyran-4-yl)-[1,2,4]triazolo[4,3-a]pyrazin-8(7H)-one (50 mg, 161.11 micromol) in DMF (2 mL) was added (bromomethyl)cyclopentane (32 mg, 193.33 micromol) and K$_2$CO$_3$ (33 mg, 241.67 micromol). The mixture was heated at 60° C. for 12 h. LCMS showed the reaction was completed. The mixture was concentrated and the residue was dissolved in DCM (20 mL) and H$_2$O (20 mL). The organic layer was washed with H$_2$O (20 mL), dried over Na$_2$SO$_4$, filtered, concentrated and purified by preparative HPLC to give 6-benzyl-7-(cyclopentylmethyl)-3-(tetrahydro-2H-pyran-4-yl)-[1,2,4]triazolo[4,3-a]pyrazin-8(7H)-one (9.7 mg, 15% yield). $^1$H NMR (CDCl$_3$ 400 MHz): δ 7.41-7.34 (m, 3H), 7.18 (d, J=6.8 Hz, 2H), 6.64 (s, 1H), 4.13-4.10 (m, 2H), 3.97 (s, 2H), 3.90 (d, J=7.6 Hz, 2H), 3.58-3.52 (m, 2H), 3.12-3.10 (m, 1H), 2.30-2.18 (m, 1H), 2.16-2.15 (m, 2H), 1.94-1.91 (m, 2H), 1.71-1.68 (m, 4H), 1.56-1.55 (m, 2H), 1.32-1.31 (m, 2H). LC-MS: $t_R$=2.83 min (METHOD 3), m/z=393.2 [M+H]$^+$

Example 41

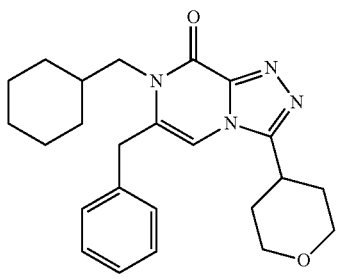 [SMILES: O=c1c2nnc(C3CCOCC3)n2cc(Cc2ccccc2)n1CC1CCCCC1]

6-benzyl-7-(cyclohexylmethyl)-3-(tetrahydro-2H-pyran-4-yl)-[1,2,4]triazolo[4,3-a]pyrazin-8(7H)-one To a suspension of 6-benzyl-3-(tetrahydro-2H-pyran-4-yl)-[1,2,4]triazolo[4,3-a]pyrazin-8(7H)-one (70 mg, 225.55 micromol) in DMF (2 mL) was added (bromomethyl)cyclohexane (48 mg, 270.66 micromol) and K$_2$CO$_3$ (47 mg, 338.33 micromol). The mixture was heated at 60° C. for 12 h. LCMS showed the reaction was completed. The mixture was concentrated and the residue was dissolved in DCM (20 mL) and H$_2$O (20 mL). The organic layer was washed with H$_2$O (20 mL), dried over Na$_2$SO$_4$, filtered, concentrated and purified by preparative HPLC (base) to give 6-benzyl-7-(cyclohexylmethyl)-3-(tetrahydro-2H-pyran-4-yl)-[1,2,4]triazolo[4,3-a]pyrazin-8(7H)-one (5.50 mg, 5.83% yield). $^1$H NMR (CDCl$_3$ 400 MHz): δ 7.41-7.34 (m, 3H), 7.17 (d, J=6.8 Hz, 2H), 6.65 (s, 1H), 4.13-4.10 (m, 2H), 3.95 (s, 2H), 3.78 (d, J=6.8 Hz, 2H), 3.58-3.53 (m, 2H), 3.12-3.10 (m, 1H), 2.20-2.15 (m, 2H), 1.94-1.91 (m, 2H), 1.75-1.66 (m, 3H), 1.63-1.58 (m, 4H), 1.17-1.03 (m, 4H). LC-MS: $t_R$=2.46 min (METHOD 6), m/z=407.2 [M+H]$^+$

Example 42

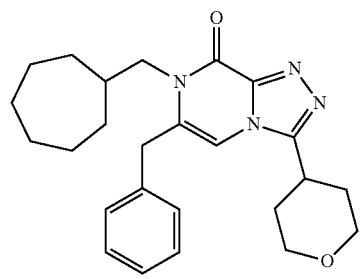 [SMILES: O=c1c2nnc(C3CCOCC3)n2cc(Cc2ccccc2)n1CC1CCCCCC1]

6-benzyl-7-(cycloheptylmethyl)-3-(tetrahydro-2H-pyran-4-yl)-[1,2,4]triazolo[4,3-a]pyrazin-8(7H)-one To a suspension of 6-benzyl-3-(tetrahydro-2H-pyran-4-yl)-[1,2,4]triazolo[4,3-a]pyrazin-8(7H)-one (200 mg, 644.43 micromol) in anhydrous DMF (5 mL) was added cycloheptylmethyl methanesulfonate (173 mg, 837.76 micromol) and K$_2$CO$_3$ (134 mg, 966.65 micromol). The mixture was heated at 60° C. for 24 h. LCMS showed 26% of desired product. The mixture was concentrated and the residue was dissolved in DCM (30 mL) and H$_2$O (30 mL). The organic layer was washed with H$_2$O (30 mL), dried over Na$_2$SO$_4$, filtered, concentrated and purified by preparative HPLC (base) to give 6-benzyl-7-(cycloheptylmethyl)-3-(tetrahydro-2H-pyran-4-yl)-[1,2,4]triazolo[4,3-a]pyrazin-8(7H)-one (22.60 mg, 8.27% yield). $^1$H NMR (CDCl$_3$ 400 MHz): δ7.40-7.34 (m, 3H), 7.17-7.15 (m, 2H), 6.65 (s, 1H), 4.13-4.10 (m, 2H), 3.94 (s, 2H), 3.77 (d, J=7.6 Hz, 2H), 3.58-3.53 (m, 2H), 3.12-3.10 (m, 1H), 2.19-2.12 (m, 2H), 2.05-1.94 (m, 1H), 1.92-1.85 (m, 2H), 1.67-1.64 (m, 4H), 1.57-1.54 (m, 4H), 1.45-1.30 (m, 2H), 1.23-1.20 (m, 2H). LC-MS: $t_R$=2.66 min (METHOD 4), m/z=421.3 [M+H]$^+$

Example 43

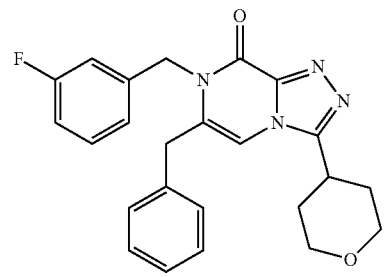 [SMILES: O=c1c2nnc(C3CCOCC3)n2cc(Cc2ccccc2)n1Cc1cccc(F)c1]

6-benzyl-7-(3-fluorobenzyl)-3-(tetrahydro-2H-pyran-4-yl)-[1,2,4]triazolo[4,3-a]pyrazin-8(7H)-one To a suspension of 6-bromo-7-(3-fluorobenzyl)-3-(tetrahydro-2H-pyran-4-yl)-[1,2,4]triazolo[4,3-a]pyrazin-8(7H)-one (100 mg, 245.56 micromol) in H$_2$O (0.5 mL) and THF (1 mL) was added 2-benzyl-4,4,5,5-tetramethyl-1,3,2-dioxaborolane (80 mg, 368.33 micromol), K$_2$CO$_3$ (68 mg, 491.11 micromol) and 1,1'-Bis(diphenylphosphino)ferrocene-palladium(II)dichloride (18 mg, 24.56 micromol). The mixture was degassed with N$_2$ and heated at 80° C. for 12 h under N$_2$. LCMS showed the reaction was completed. The mixture was cooled to 25° C. and extracted with ethyl acetate (10 mL, two times). The combined organic layer was washed with water (10 mL), dried over Na$_2$SO$_4$, filtered, concentrated and purified by preparative TLC (DCM/MeOH=10/1) to give the crude product which was purified by preparative HPLC to give 6-benzyl-7-(3-fluorobenzyl)-3-(tetrahydro-2H-pyran-4-yl)-[1,2,4]triazolo[4,3-a]pyrazin-8(7H)-one (5.90 mg, 5.74% yield). $^1$H NMR (CDCl$_3$ varian 400): δ7.39-7.36 (m, 3H), 7.31-7.30 (m, 1H), 7.13 (d, J=7.2 Hz, 2H), 6.99-6.95 (m, 1H), 6.94 (d, J=8.0 Hz, 1H), 6.85-6.80 (m, 1H), 6.74 (s, 1H), 5.15 (s, 2H), 4.13 (d, J=12.0 Hz, 2H), 3.79 (s, 2H), 3.58 (t, J=10.0 Hz, 2H), 3.19-3.13 (m, 1H), 2.24-2.15 (m, 2H), 1.96-1.93 (m, 2H). LC-MS: t$_R$=2.70 min (METHOD 3), m/z=419.2 [M+H]$^+$ Example 44

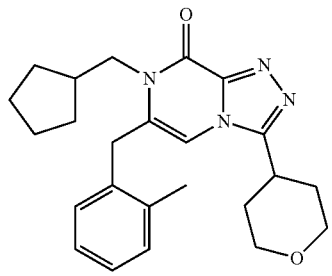

7-(cyclopentylmethyl)-6-(2-methylbenzyl)-3-(tetrahydro-2H-pyran-4-yl)-[1,2,4]triazolo[4,3-a]pyrazin-8(7H)-one Step 1:

To a suspension of 6-bromo-3-(tetrahydro-2H-pyran-4-yl)-[1,2,4]triazolo[4,3-a]pyrazin-8(7H)-one (1.20 g, 4.01 mmol) in H$_2$O (10 mL) and dioxane (20 mL) was added 4,4,5,5-tetramethyl-2-(2-methylbenzyl)-1,3,2-dioxaborolane (1.40 g, 6.02 mmol), 1,1'-Bis(diphenylphosphino)ferrocene-palladium(II)dichloride (294 mg, 401.00 micromol) and Cs$_2$CO$_3$ (2.61 g, 8.02 mmol). The mixture was degassed with N$_2$ and heated at 100° C. for 12 h under N$_2$. TLC showed the reaction was completed. The mixture was concentrated and the residue was dissolved in DCM (20 mL) and H$_2$O (10 mL). The aqueous layer was extracted with DCM (20 mL). The organics were washed with water (20 mL), dried over Na$_2$SO$_4$, filtered, concentrated and purified by flash chromatography on silica gel (DCM/MeOH=100/1-20/1) to give 6-(2-methylbenzyl)-3-(tetrahydro-2H-pyran-4-yl)-[1,2,4]triazolo[4,3-a]pyrazin-8(7H)-one (500 mg, 20.% yield).

Step 2:

To a suspension of 6-(2-methylbenzyl)-3-(tetrahydro-2H-pyran-4-yl)-[1,2,4]triazolo[4,3-a]pyrazin-8(7H)-one (150 mg, 462.42 micromol) in anhydrous DMF (5 mL) was added (bromomethyl)cyclopentane (91 mg, 554.90 micromol) and K$_2$CO$_3$ (96 mg, 693.63 micromol). The mixture was heated at 60° C. for 12 h. LCMS showed 45% of desired product. The mixture was concentrated and the residue was dissolved in DCM (20 mL) and H$_2$O (20 mL). The aqueous layer was extracted with DCM (20 mL). The combined organics were washed with H$_2$O (20 mL), dried over Na$_2$SO$_4$, filtered, concentrated and purified by preparative HPLC (base) to give 7-(cyclopentylmethyl)-6-(2-methylbenzyl)-3-(tetrahydro-2H-pyran-4-yl)-[1,2,4]triazolo[4,3-a]pyrazin-8(7H)-one (26.94 mg, 13% yield). $^1$H NMR (CDCl$_3$ 400 MHz): δ7.29-7.28 (m, 2H), 7.23-7.19 (m, 1H), 6.99 (d, J=7.6 Hz, 1H), 6.37 (s, 1H), 4.08-4.06 (m, 2H), 3.95 (d, J=7.2 Hz, 2H), 3.91 (s, 2H), 3.52-3.46 (m, 2H), 3.05-2.95 (m, 1H), 2.36-2.33 (m, 4H), 2.11-2.08 (m, 2H), 1.85-1.82 (m, 2H), 1.73-1.71 (m, 4H), 1.57-1.56 (m, 2H), 1.40-1.31 (m, 2H). LC-MS: t$_R$=2.92 min (METHOD 3), m/z=407.2 [M+H]$^+$ Example 45

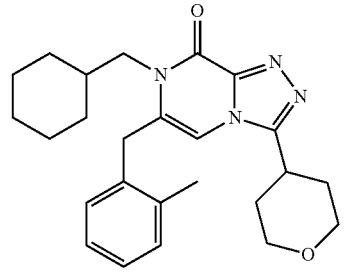 [SMILES: Cc1ccccc1Cc1cn2c(C3CCOCC3)nnc2c(=O)n1CC1CCCCC1]

7-(cyclohexylmethyl)-6-(2-methylbenzyl)-3-(tetrahydro-2H-pyran-4-yl)-[1,2,4]triazolo[4,3-a]pyrazin-8(7H)-one To a suspension of 6-(2-methylbenzyl)-3-(tetrahydro-2H-pyran-4-yl)-[1,2,4]triazolo[4,3-a]pyrazin-8(7H)-one (150 mg, 462.42 micromol) in anhydrous DMF (5 mL) was added (bromomethyl)cyclohexane (98 mg, 554.90 micromol and K$_2$CO$_3$ (96 mg, 693.63 micromol). The mixture was heated at 60° C. for 12 hr. LCMS showed 26% of desired product. The mixture was concentrated and the residue was dissolved in DCM (20 mL) and H$_2$O (20 mL). The organic layer was washed with H$_2$O (20 mL), dried over Na$_2$SO$_4$, filtered, concentrated and purified by preparative HPLC to give 7-(cyclohexylmethyl)-6-(2-methyl benzyl)-3-(tetrahydro-2H-pyran-4-yl)-[1,2,4]triazolo[4,3-a]pyrazin-8(7H)-one (21.94 mg, 11% yield). $^1$H NMR (CDCl$_3$ 400 MHz): δ7.29-7.27 (m, 2H), 7.23-7.19 (m, 1H), 6.99 (d, J=7.2 Hz, 1H), 6.36 (s, 1H), 4.08-4.04 (m, 2H), 3.88 (s, 2H), 3.79-3.75 (m, 2H), 3.52-3.46 (m, 2H), 3.00-2.99 (m, 1H), 2.33 (s, 3H), 2.12-2.08 (m, 2H), 1.86-1.82 (m, 2H), 1.73-1.67 (m, 6H), 1.19-1.17 (m, 3H), 1.09-1.06 (m, 2H). LC-MS: t$_R$=3.02 min (METHOD 3), m/z=421.2 [M+H]$^+$

Example 46

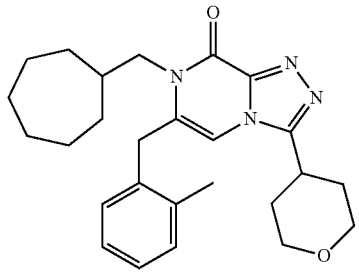 [SMILES: Cc1ccccc1Cc1cn2c(C3CCOCC3)nnc2c(=O)n1CC1CCCCCC1]

7-(cycloheptylmethyl)-6-(2-methylbenzyl)-3-(tetrahydro-2H-pyran-4-yl)-[1,2,4]triazolo[4,3-a]pyrazin-8(7H)-one To a suspension of 6-(2-methylbenzyl)-3-(tetrahydro-2H-pyran-4-yl)-[1,2,4]triazolo[4,3-a]pyrazin-8(7H)-one (150 mg, 462.42 micromol) in anhydrous DMF (5 mL) was added cycloheptylmethyl methanesulfonate (124 mg, 601.15 micromol) and $K_2CO_3$ (96 mg, 693.63 micromol). The mixture was heated at 60° C. for 12 h. LCMS showed 22% of desired product. The mixture was concentrated and the residue was dissolved in DCM (20 mL) and $H_2O$ (20 mL). The organic layer was washed with $H_2O$ (20 mL), dried over $Na_2SO_4$, filtered, concentrated and purified by preparative HPLC (base) to give 7-(cycloheptylmethyl)-6-(2-methylbenzyl)-3-(tetrahydro-2H-pyran-4-yl)-[1,2,4]triazolo[4,3-a]pyrazin-8(7H)-one (10.5 mg, 5.22% yield). $^1$H NMR ($CDCl_3$, 400 MHz): δ 7.29-7.27 (m, 2H), 7.23-7.19 (m, 1H), 6.99 (d, J=7.2 Hz, 1H), 6.35 (s, 1H), 4.08-4.06 (m, 2H), 3.88 (s, 2H), 3.80-3.79 (m, 2H), 3.52-3.46 (m, 2H), 3.00-2.99 (m, 1H), 2.33 (s, 3H), 2.11-2.08 (m, 3H), 1.85-1.83 (m, 2H), 1.69-1.67 (m, 4H), 1.57-1.52 (m, 4H), 1.45-1.30 (m, 2H), 1.27-1.24 (m, 2H). LC-MS: $t_R$=3.11 min (METHOD 3), m/z=435.2 [M+H]+

Example 47

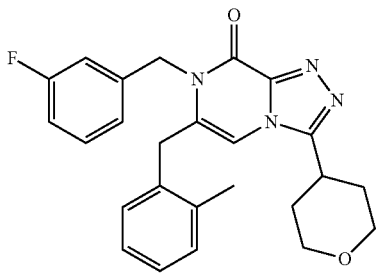 [SMILES: Cc1ccccc1Cc1cn2c(C3CCOCC3)nnc2c(=O)n1Cc1cccc(F)c1]

7-(3-fluorobenzyl)-6-(2-methylbenzyl)-3-(tetrahydro-2H-pyran-4-yl)-[1,2,4]triazolo[4,3-a]pyrazin-8(7H)-one To a suspension of 6-bromo-7-(3-fluorobenzyl)-3-(tetrahydro-2H-pyran-4-yl)-[1,2,4]triazolo[4,3-a]pyrazin-8(7H)-one (200 mg, 491.11 micromol) in dioxane (4 mL) and $H_2O$ (2.00 mL) was added 4,4,5,5-tetramethyl-2-(2-methylbenzyl)-1,3,2-dioxaborolane (171 mg, 736.67 micromol), $K_2CO_3$ (136 mg, 982.22 micromol) and 1,1'-Bis(diphenylphosphino)ferrocene-palladium(II)dichloride (36 mg, 49.11 micromol). The mixture was degassed with $N_2$ and heated at 80° C. for 12 h under $N_2$. LCMS showed the reaction was completed. The mixture was cooled to 25° C. and extracted with EA (20 mL, two times). The organic layer was washed with water (10 mL), dried over $Na_2SO_4$, filtered, concentrated and purified by prep-TLC (DCM/MeOH=20/1) to give the crude product which was purified by preparative HPLC (base) to give 7-(3-fluorobenzyl)-6-(2-methylbenzyl)-3-(tetrahydro-2H-pyran-4-yl)-[1,2,4]triazolo[4,3-a]pyrazin-8(7H)-one (13.75 mg, 6.47% yield). $^1$H NMR (CDCl3 400 MHz): δ 7.33-7.30 (m, 1H), 7.26-7.25 (m, 3H), 7.01-6.99 (m, 3H), 6.97-6.90 (m, 1H), 6.41 (s, 1H), 5.27 (s, 2H), 4.10-4.06 (m, 2H), 3.76 (s, 2H), 3.52-3.46 (m, 2H), 3.02-2.99 (m, 1H), 2.15-2.09 (m, 5H), 1.87-1.84 (m, 2H). LC-MS: $t_R$=2.84 min (METHOD 3), m/z=433.2 [M+H]+

Example 48

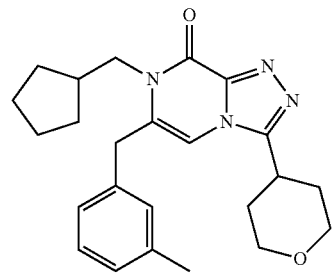

7-(cyclopentylmethyl)-6-(3-methylbenzyl)-3-(tetrahydro-2H-pyran-4-yl)-[1,2,4]triazolo[4,3-a]pyrazin-8(7H)-one Step 1:
To a solution of 1-(chloromethyl)-3-methylbenzene (2.00 g, 14.22 mmol) in anhydrous dioxane (20 mL) was added 4,4,4',4',5,5,5',5'-octamethyl-2,2'-bi(1,3,2-dioxaborolane) (5.42 g, 21.34 mmol), KOAc (4.19 g, 42.67 mmol) and 1,1'-Bis(diphenylphosphino)ferrocene-palladium(II)dichloride (1.04 g, 1.42 mmol). The mixture was degassed with $N_2$ and heated at 80° C. for 1 h under $N_2$. The mixture was concentrated and the residue was diluted with MTBE (100 mL) and filtered through a pad of silica gel. The filtrate was concentrated to give 4,4,5,5-tetramethyl-2-(3-methylbenzyl)-1,3,2-dioxaborolane (4.00 g, crude). The crude was used for the next step without further purification.
Step 2:
To a suspension of 6-bromo-3-(tetrahydro-2H-pyran-4-yl)-[1,2,4]triazolo[4,3-a]pyrazin-8(7H)-one (1.50 g, 5.01 mmol) in $H_2O$ (10 mL) and dioxane (20 mL) was added 4,4,5,5-tetramethyl-2-(3-methylbenzyl)-1,3,2-dioxaborolane (3.00 g, crude), 1,1'-Bis(diphenylphosphino)ferrocene-palladium(II)dichloride (367 mg, 501.00 micromol) and $K_2CO_3$ (1.38 g, 10.02 mmol). The mixture was degassed with $N_2$ and heated at 100° C. for 12 h under $N_2$. The mixture was concentrated and the residue was dissolved in DCM (30 mL) and $H_2O$ (30 mL). The aqueous layer was extracted with DCM (30 mL). The organics were washed with water (30 mL), dried over $Na_2SO_4$, filtered, concentrated and purified by flash chromatography on silica gel (DCM/

MeOH=100/1-20/1) to give 6-(3-methylbenzyl)-3-(tetrahydro-2H-pyran-4-yl)-[1,2,4]triazolo[4,3-a]pyrazin-8(7H)-one (800 mg, 31.50% yield).

Step 3:

To a suspension of 6-(3-methylbenzyl)-3-(tetrahydro-2H-pyran-4-yl)-[1,2,4]triazolo[4,3-a]pyrazin-8(7H)-one (150 mg, 462.42 micromol) in anhydrous DMF (5 mL) was added (bromomethyl)cyclopentane (90 mg, 554.90 micromol) and K$_2$CO$_3$ (96 mg, 693.63 micromol). The mixture was heated at 60° C. for 12 h. LCMS showed 35% of desired product. The mixture was concentrated and the residue was dissolved in DCM (20 mL) and H$_2$O (20 mL). The aqueous layer was extracted with DCM (20 mL). The combined organics were washed with H$_2$O (20 mL), dried over Na$_2$SO$_4$, filtered, concentrated and purified by preparative HPLC to give 7-(cyclopentylmethyl)-6-(3-methylbenzyl)-3-(tetrahydro-2H-pyran-4-yl)-[1,2,4]triazolo[4,3-a]pyrazin-8(7H)-one (25.60 mg, 13.62% yield). $^1$H NMR (CDCl3 400 MHz): δ7.28-7.24 (m, 1H), 7.15 (d, J=7.6 Hz, 1H), 6.96-6.94 (m, 2H), 6.68 (s, 1H), 4.13-4.09 (m, 2H), 3.92-3.88 (m, 4H), 3.59-3.53 (m, 2H), 3.14-3.13 (m, 1H), 2.35 (s, 3H), 2.17-2.10 (m, 3H), 1.95-1.90 (m, 2H), 1.71-1.67 (m, 4H), 1.55-1.54 (m, 2H), 1.31-1.30 (m, 2H). LC-MS: t$_R$=3.10 min (METHOD 3), m/z=407.2 [M+H]$^+$ Example 49

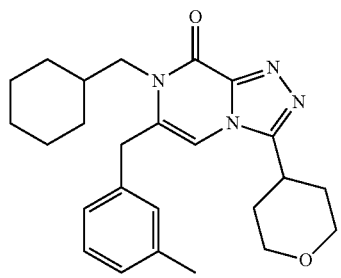 [SMILES: Cc1cccc(Cc2cn3c(C4CCOCC4)nnc3c(=O)n2CC2CCCCC2)c1]

7-(cyclohexylmethyl)-6-(3-methylbenzyl)-3-(tetrahydro-2H-pyran-4-yl)-[1,2,4]triazolo[4,3-a]pyrazin-8(7H)-one To a suspension of 6-(3-methyl benzyl)-3-(tetrahydro-2H-pyran-4-yl)-[1,2,4]triazolo[4,3-a]pyrazin-8(7H)-one (150 mg, 462.42 micromol) in anhydrous DMF (5 mL) was added (bromomethyl)cyclohexane (98 mg, 554.90 micromol) and K$_2$CO$_3$ (96 mg, 693.63 micromol). The mixture was heated at 60° C. for 12 h. LCMS showed 32% of desired product. The mixture was concentrated and the residue was dissolved in DCM (20 mL) and H$_2$O (20 mL). The aqueous layer was extracted with DCM (20 mL). The combined organics were washed with H$_2$O (20 mL), dried over Na$_2$SO$_4$, filtered, concentrated and purified by preparative HPLC (base) to give 7-(cyclohexylmethyl)-6-(3-methylbenzyl)-3-(tetrahydro-2H-pyran-4-yl)-[1,2,4]triazolo[4,3-a]pyrazin-8(7H)-one (12.60 mg, 6.48% yield). $^1$H NMR (CDCl$_3$ 400 MHz): δ 7.28-7.24 (m, 1H), 7.14 (d, J=7.6 Hz, 1H), 6.96-6.94 (m, 2H), 6.68 (s, 1H), 4.13-4.10 (m, 2H), 3.91 (s, 2H), 3.77-3.75 (m, 2H), 3.59-3.53 (m, 2H), 3.14-3.12 (m, 1H), 2.35 (s, 3H), 2.20-2.14 (m, 2H), 1.95-1.92 (m, 2H), 1.73-1.72 (m, 2H), 1.65-1.60 (m, 5H), 1.17-1.15 (m, 1H), 1.08-1.02 (m, 2H). LC-MS: t$_R$=3.21 min (METHOD 3), m/z=421.2 [M+H]$^+$ Example 50

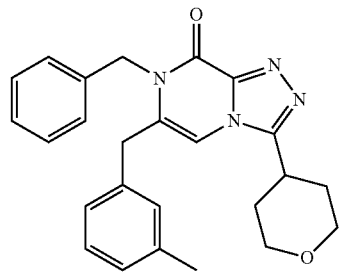 [SMILES: Cc1cccc(Cc2cn3c(C4CCOCC4)nnc3c(=O)n2Cc2ccccc2)c1]

7-benzyl-6-(3-methylbenzyl)-3-(tetrahydro-2H-pyran-4-yl)-[1,2,4]triazolo[4,3-a]pyrazin-8(7H)-one To a suspension of 6-(3-methylbenzyl)-3-(tetrahydro-2H-pyran-4-yl)-[1,2,4]triazolo[4,3-a]pyrazin-8(7H)-one (150 mg, 462.42 micromol) in anhydrous DMF (5 mL) was added 1-(bromomethyl)-3-fluorobenzene (105 mg, 554.90 micromol) and K$_2$CO$_3$ (96 mg, 693.63 micromol). The mixture was heated at 60° C. for 12 h. The mixture was concentrated and the residue was dissolved in DCM (20 mL) and H$_2$O (20 mL). The aqueous layer was extracted with DCM (20 mL). The combined organics were washed with H$_2$O (20 mL), dried over Na$_2$SO$_4$, filtered, concentrated and purified by preparative HPLC (base) to give 7-benzyl-6-(3-methylbenzyl)-3-(tetrahydro-2H-pyran-4-yl)-[1,2,4]triazolo[4,3-a]pyrazin-8(7H)-one (46.0 mg, 23.00% yield). $^1$H NMR (CDCl$_3$ 400 MHz): δ 7.33-7.29 (m, 1H), 7.26-7.25 (m, 1H), 7.15 (d, J=7.6 Hz, 1H), 6.99-6.95 (m, 1H), 6.94-6.87 (m, 3H), 6.85-6.81 (m, 1H), 6.80 (s, 1H), 5.15 (s, 2H), 4.15-4.12 (m, 2H), 3.76 (s, 2H), 3.60-3.54 (m, 2H), 3.22-3.18 (m, 1H), 2.34 (s, 3H), 2.23-2.17 (m, 2H), 1.98-1.95 (m, 2H). LC-MS: t$_R$=3.01 min (METHOD 3), m/z=433.1 [M+H]$^+$ Example 51

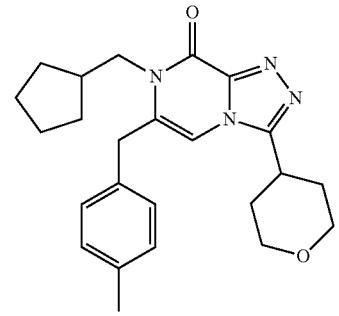 [SMILES: Cc1ccc(Cc2cn3c(C4CCOCC4)nnc3c(=O)n2CC2CCCC2)cc1]

7-(cyclopentylmethyl)-6-(4-methylbenzyl)-3-(tetrahydro-2H-pyran-4-yl)-[1,2,4]triazolo[4,3-a]pyrazin-8(7H)-one Step 1:

To a suspension of 6-bromo-3-(tetrahydro-2H-pyran-4-yl)-[1,2,4]triazolo[4,3-a]pyrazin-8(7H)-one (1.00 g, 3.34 mmol) in H$_2$O (10 mL) and dioxane (20 mL) was added 4,4,5,5-tetramethyl-2-(4-methylbenzyl)-1,3,2-dioxaborolane (1.16 g, 5.01 mmol), 1,1'-Bis(diphenylphosphino)ferrocene-palladium(II)dichloride (245 mg, 334.31 micromol) and $Cs_2CO_3$ (2.18 g, 6.69 mmol). The mixture was degassed with $N_2$ and heated at 100° C. for 12 h under $N_2$. LCMS showed the reaction was completed. The mixture was cooled to 25° C. and extracted with EA (20 mL, two times). The organic layer was washed with water (20 mL), dried over $Na_2SO_4$, filtered, concentrated and purified by flash chromatography on silica gel (DCM/MeOH=100/1-20/1) to give 6-(4-methyl benzyl)-3-(tetrahydro-2H-pyran-4-yl)-[1,2,4]triazolo[4,3-a]pyrazin-8(7H)-one (500 mg, 38.62% yield).
Step 2:

To a suspension of 6-(4-methylbenzyl)-3-(tetrahydro-2H-pyran-4-yl)-[1,2,4]triazolo[4,3-a]pyrazin-8(7H)-one (150 mg, 462.42 micromol) in anhydrous DMF (5 mL) was added (bromomethyl)cyclopentane (91 mg, 554.90 micromol) and $K_2CO_3$ (96 mg, 693.63 micromol). The mixture was heated at 60° C. for 12 h. LCMS showed 44% of desired product. The mixture was concentrated and the residue was dissolved in DCM (20 mL) and $H_2O$ (20 mL). The aqueous layer was extracted with DCM (20 mL). The combined organics were washed with $H_2O$ (20 mL), dried over $Na_2SO_4$, filtered, concentrated and purified by preparative HPLC (base) to give 7-(cyclopentylmethyl)-6-(4-methylbenzyl)-3-(tetrahydro-2H-pyran-4-yl)-[1,2,4]triazolo[4,3-a]pyrazin-8(7H)-one (47.00 mg, 24.74% yield). $^1$H NMR ($CDCl_3$ varian 400): δ7.17 (d, J=7.6 Hz, 2H), 7.03 (d, J=8.0 Hz, 2H), 6.65 (s, 1H), 4.11-4.08 (m, 2H), 3.90-3.86 (m, 4H), 3.56-3.51 (m, 2H), 3.12-3.09 (m, 1H), 2.34 (s, 3H), 2.35-2.25 (m, 1H), 2.16-2.13 (m, 2H), 1.92-1.89 (m, 2H), 1.67-1.63 (m, 4H), 1.53-1.51 (m, 2H), 1.31-1.26 (m, 2H). LC-MS: $t_R$=2.95 min (METHOD 3), m/z=407.2 [M+H]$^+$ Example 52

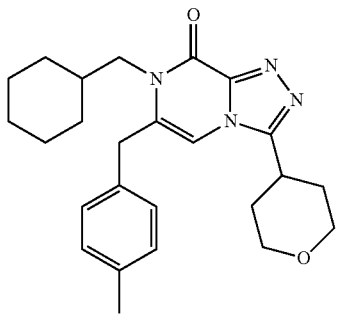 [SMILES: Cc1ccc(Cc2cn3c(C4CCOCC4)nnc3c(=O)n2CC2CCCCC2)cc1]

7-(cyclohexylmethyl)-6-(4-methylbenzyl)-3-(tetrahydro-2H-pyran-4-yl)-[1,2,4]triazolo[4,3-a]pyrazin-8(7H)-one To a suspension of 6-(4-methylbenzyl)-3-(tetrahydro-2H-pyran-4-yl)-[1,2,4]triazolo[4,3-a]pyrazin-8(7H)-one (150 mg, 462.42 micromol) in anhydrous DMF (5 mL) was added (bromomethyl)cyclohexane (98 mg, 554.90 micromol) and $K_2CO_3$ (96 mg, 693.63 micromol). The mixture was heated at 60° C. for 12 h. LCMS showed 32% of desired product. The mixture was concentrated and the residue was dissolved in DCM (20 mL) and $H_2O$ (20 mL). The aqueous layer was extracted with DCM (20 mL). The combined organics were washed with $H_2O$ (20 mL), dried over $Na_2SO_4$, filtered, and purified by preparative HPLC (base) to give 7-(cyclohexylmethyl)-6-(4-methylbenzyl)-3-(tetrahydro-2H-pyran-4-yl)-[1,2,4]triazolo[4,3-a]pyrazin-8(7H)-one (23.90 mg, 12.29% yield). $^1$H NMR (CDCl3 400 MHz): δ7.19 (d, J=8.0 Hz, 2H), 7.05 (d, J=8.0 Hz, 2H), 6.67 (s, 1H), 4.13-4.10 (m, 2H), 3.90 (s, 2H), 3.77-3.75 (m, 2H), 3.59-3.53 (m, 2H), 3.14-3.11 (m, 1H), 2.36 (s, 3H), 2.20-2.15 (m, 2H), 1.94-1.92 (m, 2H), 1.74-1.72 (m, 2H), 1.65-1.62 (m, 5H), 1.17-1.15 (m, 2H), 1.06-1.02 (m, 2H). LC-MS: $t_R$=3.04 min (METHOD 3), m/z=421.3 [M+H]$^+$ Example 53

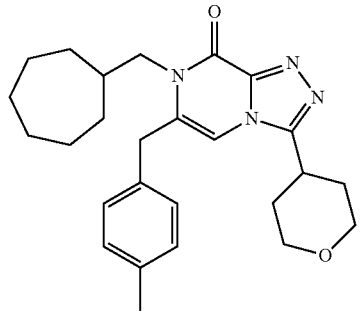 [SMILES: Cc1ccc(Cc2cn3c(C4CCOCC4)nnc3c(=O)n2CC2CCCCCC2)cc1]

7-(cycloheptylmethyl)-6-(4-methylbenzyl)-3-(tetrahydro-2H-pyran-4-yl)-[1,2,4]triazolo[4,3-a]pyrazin-8(7H)-one To a suspension of 6-(4-methylbenzyl)-3-(tetrahydro-2H-pyran-4-yl)-[1,2,4]triazolo[4,3-a]pyrazin-8(7H)-one (200 mg, 616.56 micromol) in anhydrous DMF (10 mL) was added cycloheptylmethyl methanesulfonate (165 mg, 801.53 micromol) and $K_2CO_3$ (128 mg, 924.84 micromol). The mixture was heated at 60° C. for 12 h. LCMS showed 26% of desired product. The mixture was concentrated and the residue was dissolved in DCM (20 mL) and $H_2O$ (20 mL). The aqueous layer was extracted with DCM (20 mL). The combined organics were washed with $H_2O$ (20 mL), dried over $Na_2SO_4$, filtered, concentrated and purified by preparative HPLC (base) to give 7-(cycloheptylmethyl)-6-(4-methyl benzyl)-3-(tetrahydro-2H-pyran-4-yl)-[1,2,4]triazolo[4,3-a]pyrazin-8(7H)-one (26.50 mg, 9.89% yield). $^1$H NMR ($CDCl_3$ varian 400): δ7.17 (d, J=8.0 Hz, 2H), 7.02 (d, J=8.0 Hz, 2H), 6.65 (s, 1H), 4.11-4.09 (m, 2H), 3.87 (s, 2H), 3.74-3.72 (m, 2H), 3.57-3.52 (m, 2H), 3.15-3.11 (m, 1H), 2.34 (s, 3H), 2.18-2.14 (m, 2H), 2.05-1.90 (m, 3H), 1.63-1.60 (m, 4H), 1.53-1.47 (m, 4H), 1.37-1.34 (m, 2H), 1.21-1.18 (m, 2H). LC-MS: $t_R$=2.82 min (METHOD 4), m/z=435.3 [M+H]$^+$ Example 54

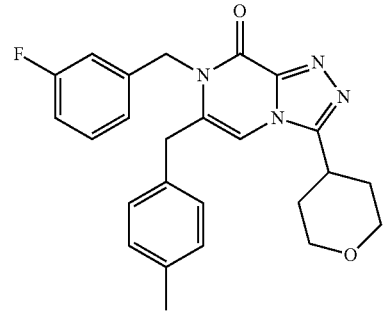 [SMILES: Cc1ccc(Cc2cn3c(C4CCOCC4)nnc3c(=O)n2Cc2cccc(F)c2)cc1]

7-(3-fluorobenzyl)-6-(4-methylbenzyl)-3-(tetrahydro-2H-pyran-4-yl)-[1,2,4]triazolo[4,3-a]pyrazin-8(7H)-one To a suspension of 6-bromo-7-(3-fluorobenzyl)-3-(tetrahydro-2H-pyran-4-yl)-[1,2,4]triazolo[4,3-a]pyrazin-8(7H)-one (100 mg, 245.56 micromol) in dioxane (2 mL) and H$_2$O (1 mL) was added 4,4,5,5-tetramethyl-2-(4-methylbenzyl)-1,3,2-dioxaborolane (86 mg, 368.33 micromol), K$_2$CO$_3$ (68 mg, 491.11 micromol) and 1,1'-Bis(diphenylphosphino)ferrocene-palladium(II)dichloride (18 mg, 24.56 micromol). The mixture was degassed with N$_2$ and heated at 80° C. for 12 h under N$_2$. LCMS showed the reaction was completed. The mixture was cooled to 25° C. and extracted with EA (10 mL, two times). The organic layer was washed with water (10 mL), dried over Na$_2$SO$_4$, filtered, concentrated and purified by prep-TLC (DCM/MeOH=20/1) to give the crude product which was purified by preparative HPLC (base) to give 7-(3-fluorobenzyl)-6-(4-methylbenzyl)-3-(tetrahydro-2H-pyran-4-yl)-[1,2,4]triazolo[4,3-a]pyrazin-8(7H)-one (8.89 mg, 8.04% yield). $^1$H NMR (CDCl$_3$ 400 MHz): δ 7.32-7.30 (m, 1H), 7.20 (d, J=7.6 Hz, 2H), 7.02-6.99 (m, 3H), 6.94-6.92 (m, 1H), 6.85-6.80 (m, 1H), 6.77 (s, 1H), 5.15 (s, 2H), 4.16-4.12 (m, 2H), 3.75 (s, 2H), 3.61-3.54 (m, 2H), 3.18-3.17 (m, 1H), 2.37 (s, 3H), 2.23-2.19 (m, 2H), 1.98-1.94 (m, 2H). LC-MS: t$_R$=2.43 min (METHOD 6), m/z=433.2 [M+H]$^+$

Example 55

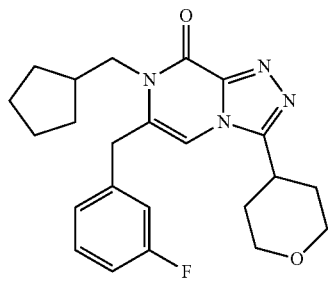 [SMILES: O=c1c2nnc(C3CCOCC3)n2cc(Cc2cccc(F)c2)n1CC1CCCC1]

7-(cyclopentylmethyl)-6-(3-fluorobenzyl)-3-(tetrahydro-2H-pyran-4-yl)-[1,2,4]triazolo[4,3-a]pyrazin-8(7H)-one Step 1:

To a suspension of 6-bromo-3-(tetrahydro-2H-pyran-4-yl)-[1,2,4]triazolo[4,3-a]pyrazin-8(7H)-one (1.50 g, 5.01 mmol) in H$_2$O (4 mL) and dioxane (10 mL) was added 2-(3-fluorobenzyl)-4,4,5,5-tetramethyl-1,3,2-dioxaborolane (1.78 g, 7.52 mmol), 1,1'-Bis(diphenylphosphino)ferrocene-palladium(II)dichloride (734 mg, 1.0 mmol) and Cs$_2$CO$_3$ (3.27 g, 10.03 mmol). The mixture was degassed with N$_2$ and heated at 100° C. for 16 h under N$_2$. The mixture was concentrated and the residue was dissolved in DCM (20 mL) and H$_2$O (10 mL). The aqueous layer was extracted with DCM (20 mL). The organics were washed with water (20 mL), dried over Na$_2$SO$_4$, filtered, concentrated and purified by flash chromatography on silica gel (DCM/MeOH=100/1-20/1) to give 6-(3-fluorobenzyl)-3-(tetrahydro-2H-pyran-4-yl)-[1,2,4]triazolo[4,3-a]pyrazin-8(7H)-one (190 mg, 11.6% yield) as a black solid.

Step 2:

To a suspension of 6-(3-fluorobenzyl)-3-(tetrahydro-2H-pyran-4-yl)-[1,2,4]triazolo[4,3-a]pyrazin-8(7H)-one (70 mg, 213.2 micromol) in anhydrous DMF (3 mL) was added (bromomethyl)cyclopentane (42 mg, 255.8 micromol) and K$_2$CO$_3$ (44 mg, 320 micromol). The mixture was heated at 60° C. for 36 h. The mixture was cooled and filtered. The filtrate was purified by preparative HPLC to give 7-(cyclopentylmethyl)-6-(3-fluorobenzyl)-3-(tetrahydro-2H-pyran-4-yl)-[1,2,4]triazolo[4,3-a]pyrazin-8(7H)-one (15 mg, 17% yield). $^1$H NMR (CDCl$_3$ 400 MHz): δ 7.37-7.34 (m, 1H), 7.06-7.03 (m, 1H), 6.96 (d, J=8.0 Hz, 1H), 6.88 (d, J=9.2 Hz, 1H), 6.71 (s, 1H), 4.14-4.11 (m, 1H), 3.97 (s, 2H), 3.88 (d, J=7.2 Hz, 2H), 3.59-3.53 (m, 2H), 3.16-3.12 (m, 1H), 2.28-2.16 (m, 3H), 1.95-1.92 (m, 2H), 1.70-1.54 (m, 6H), 1.31-1.30 (m, 2H). LC-MS: t$_R$=2.82 min (METHOD 3), m/z=411.2 [M+H]$^+$.

Example 56

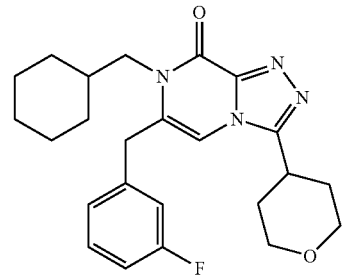 [SMILES: O=c1c2nnc(C3CCOCC3)n2cc(Cc2cccc(F)c2)n1CC1CCCCC1]

7-(cyclohexylmethyl)-6-(3-fluorobenzyl)-3-(tetrahydro-2H-pyran-4-yl)-[1,2,4]triazolo[4,3-a]pyrazin-8(7H)-one To a suspension of 6-(3-fluorobenzyl)-3-(tetrahydro-2H-pyran-4-yl)-[1,2,4]triazolo[4,3-a]pyrazin-8(7H)-one (70 mg, 213.2 micromol) in anhydrous DMF (3 mL) was added (bromomethyl)cyclohexane (45 mg, 255.8 micromol) and K$_2$CO$_3$ (44 mg, 320 micromol). The mixture was heated at 60° C. for 36 h. The mixture was cooled and filtered. The filtrate was purified by preparative HPLC to give 7-(cyclohexylmethyl)-6-(3-fluorobenzyl)-3-(tetrahydro-2H-pyran-4-yl)-[1,2,4]triazolo[4,3-a]pyrazin-8(7H)-one (18 mg, 19% yield). $^1$H NMR (CDCl$_3$ 400 MHz): δ 7.37-7.34 (m, 1H), 7.06-7.03 (m, 1H), 6.95 (d, J=7.6 Hz, 1H), 6.88 (d, J=9.6 Hz, 1H), 6.71 (s, 1H), 4.14-4.11 (m, 1H), 3.95 (s, 2H), 3.74 (d, J=7.2 Hz, 2H), 3.59-3.54 (m, 2H), 3.18-3.13 (m, 1H), 2.23-2.14 (m, 2H), 1.96-1.93 (m, 2H), 1.74-1.60 (m, 7H), 1.75-1.03 (m, 4H).

LC-MS: t$_R$=2.92 min (METHOD 3), m/z=425.2 [M+H]$^+$.

Example 57

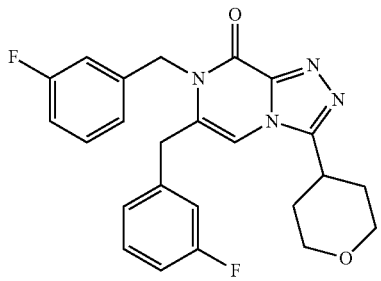 [SMILES: O=c1c2nnc(C3CCOCC3)n2cc(Cc2cccc(F)c2)n1Cc1cccc(F)c1]

6,7-bis(3-fluorobenzyl)-3-(tetrahydro-2H-pyran-4-yl)-[1,2,4]triazolo[4,3-a]pyrazin-8(7H)-one To a suspension of 6-(3-fluorobenzyl)-3-(tetrahydro-2H-pyran-4-yl)-[1,2,4]triazolo[4,3-a]pyrazin-8(7H)-one (70 mg, 213.2 micromol) in anhydrous DMF (3 mL) was added 1-(bromomethyl)-3-fluorobenzene (48 mg, 255.8 micromol) and $K_2CO_3$ (44 mg, 320 micromol). The mixture was heated at 60° C. for 16 h. The mixture was cooled and diluted with water (5 mL), extracted with DCM (5 mL, two times). The organic layer was washed with brine, dried and concentrated in vacuo. The residue was purified by prep-TLC (DCM/MeOH=10/1) to give 6,7-bis(3-fluorobenzyl)-3-(tetrahydro-2H-pyran-4-yl)-[1,2,4]triazolo[4,3-a]pyrazin-8(7H)-one (5 mg, 5% yield). $^1$H NMR (CDCl$_3$ 400 MHz): δ 7.38-7.32 (m, 2H), 7.05-7.00 (m, 2H), 6.94-6.92 (m, 2H), 6.86-6.84 (m, 2H), 6.85-6.80 (m, 1H), 6.79 (s, 2H), 5.15 (s, 2H), 4.16-4.13 (m, 2H), 3.80 (s, 2H), 3.61-3.55 (m, 2H), 3.22-3.16 (m, 1H), 2.28-2.17 (m, 2H), 1.98-1.95 (m, 2H). LC-MS: $t_R$=2.46 min (METHOD 3), m/z=437.2 [M+H].

Example 58

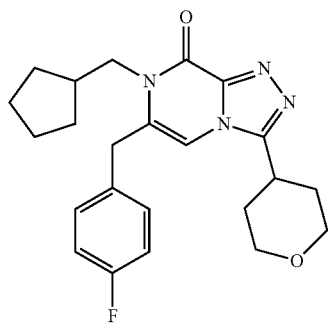 [SMILES: O=c1c2nnc(C3CCOCC3)n2cc(Cc2ccc(F)cc2)n1CC1CCCC1]

7-(cyclopentylmethyl)-6-(4-fluorobenzyl)-3-(tetrahydro-2H-pyran-4-yl)-[1,2,4]triazolo[4,3-a]pyrazin-8(7H)-one Step 1:

To a suspension of 6-bromo-3-(tetrahydro-2H-pyran-4-yl)-[1,2,4]triazolo[4,3-a]pyrazin-8(7H)-one (1.50 g, 5.01 mmol) in H$_2$O (10 mL) and dioxane (20 mL) was added 2-(4-fluorobenzyl)-4,4,5,5-tetramethyl-1,3,2-dioxaborolane (1.78 g, 7.52 mmol), 1,1'-Bis(diphenylphosphino)ferrocene-palladium(II)dichloride (367 mg, 501.47 micromol) and Cs$_2$CO$_3$ (3.27 g, 10.03 mmol). The mixture was degassed with N$_2$ and heated at 100° C. for 12 h under N$_2$. LCMS showed the reaction was completed. The mixture was concentrated and the residue was dissolved in DCM (20 mL) and H$_2$O (10 mL). The aqueous layer was extracted with DCM (20 mL). The organics were washed with water (20 mL), dried over Na$_2$SO$_4$, filtered, concentrated and purified by flash chromatography on silica gel (DCM/MeOH=100/1-20/1) to give 6-(4-fluorobenzyl)-3-(tetrahydro-2H-pyran-4-yl)-[1,2,4]triazolo[4,3-a]pyrazin-8(7H)-one (600 mg, 24.80% yield).

Step 2:

To a suspension of 6-(4-fluorobenzyl)-3-(tetrahydro-2H-pyran-4-yl)-[1,2,4]triazolo[4,3-a]pyrazin-8(7H)-one (150 mg, 456.84 micromol) in anhydrous DMF (5 mL) was added (bromomethyl)cyclopentane (89. mg, 548.21 micromol) and K$_2$CO$_3$ (95 mg, 685.27 micromol). The mixture was heated at 60° C. for 12 h. LCMS showed 23% TM. The mixture was concentrated and the residue was dissolved in DCM (20 mL) and H$_2$O (20 mL). The aqueous layer was extracted with DCM (20 mL). The combined organics were washed with H$_2$O (20 mL), dried over Na$_2$SO$_4$, filtered, concentrated and purified by prep-TLC (DCM/MeOH=50/1) to give 7-(cyclopentylmethyl)-6-(4-fluorobenzyl)-3-(tetrahydro-2H-pyran-4-yl)-[1,2,4]triazolo[4,3-a]pyrazin-8(7H)-one (25.90 mg, 13.67% yield). $^1$H NMR (CDCl3 400 MHz): δ7.17-7.13 (m, 2H), 7.11-7.06 (m, 2H), 6.64 (s, 1H), 4.13-4.10 (m, 2H), 3.94 (s, 2H), 3.90 (d, J=7.2 Hz, 2H), 3.59-3.53 (m, 2H), 3.13-3.12 (m, 1H), 2.28-2.10 (m, 1H), 2.19-2.16 (m, 2H), 1.94-1.91 (m, 2H), 1.71-1.68 (m, 4H), 1.54-1.45 (m, 2H), 1.33-1.28 (m, 2H). LC-MS: $t_R$=2.84 min (METHOD 3), m/z=411.2 [M+H]$^+$

Example 59

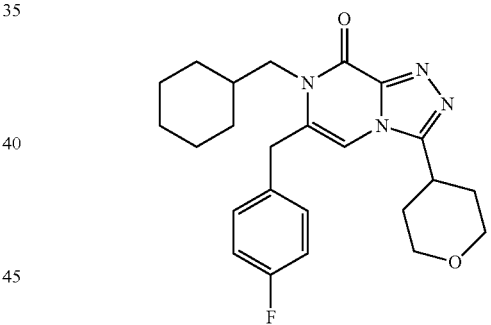

7-(cyclohexylmethyl)-6-(4-fluorobenzyl)-3-(tetrahydro-2H-pyran-4-yl)-[1,2,4]triazolo[4,3-a]pyrazin-8(7H)-one To a suspension of 6-(4-fluorobenzyl)-3-(tetrahydro-2H-pyran-4-yl)-[1,2,4]triazolo[4,3-a]pyrazin-8(7H)-one (150 mg, 456.84 micromol) in anhydrous DMF (5 mL) was added (bromomethyl)cyclohexane (97 mg, 548.21 micromol) and K$_2$CO$_3$ (95 mg, 685.27 micromol). The mixture was heated at 60° C. for 12 h. LCMS showed 36% of desired product. The mixture was concentrated and the residue was dissolved in DCM (20 mL) and H$_2$O (20 mL). The aqueous layer was extracted with DCM (20 mL). The combined organics were washed with H$_2$O (20 mL), dried over Na$_2$SO$_4$, filtered, concentrated and purified by prep-TLC (DCM/MeOH=50/1) to give 7-(cyclohexylmethyl)-6-(4-fluorobenzyl)-3-(tetrahydro-2H-pyran-4-yl)-[1,2,4]triazolo[4,3-a]pyrazin-8(7H)-one (23.50 mg, 12.00% yield). $^1$H NMR (CDCl3 400 MHz): δ7.17-7.06 (m, 4H), 6.65 (s, 1H), 4.13-4.10 (m, 2H), 3.92 (s, 2H), 3.76-3.74 (m, 2H), 3.59-3.54 (m, 2H), 3.13-3.12 (m, 1H), 2.20-2.16 (m, 2H), 1.94-1.91 (m, 2H), 1.77-1.72 (m, 3H), 1.65-1.60 (m, 4H), 1.18-1.15 (m, 2H), 1.06-1.03 (m, 2H). LC-MS: $t_R$=2.92 min (METHOD 3), m/z=425.2 [M+H]$^+$ Example 60

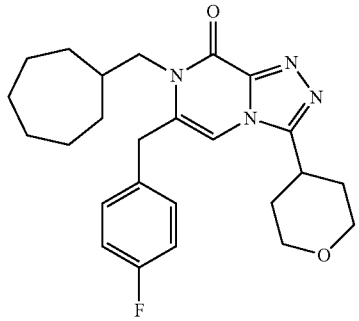 [SMILES: O=c1c2nnc(C3CCOCC3)n2cc(Cc2ccc(F)cc2)n1CC1CCCCCC1]

7-(cycloheptylmethyl)-6-(4-fluorobenzyl)-3-(tetrahydro-2H-pyran-4-yl)-[1,2,4]triazolo[4,3-a]pyrazin-8(7H)-one To a suspension of 6-(4-fluorobenzyl)-3-(tetrahydro-2H-pyran-4-yl)-[1,2,4]triazolo[4,3-a]pyrazin-8(7H)-one (150 mg, 456.84 micromol) in anhydrous DMF (5 mL) was added cycloheptylmethyl methanesulfonate (122 mg, 593.90 micromol) and K$_2$CO$_3$ (95 mg, 685.27 micromol). The mixture was heated at 60° C. for 12 h. LCMS showed 21% of desired product. The mixture was concentrated and the residue was dissolved in DCM (20 mL) and H$_2$O (20 mL). The aqueous layer was extracted with DCM (20 mL). The combined organics were washed with H$_2$O (20 mL), dried over Na$_2$SO$_4$, filtered, concentrated and purified by preparative HPLC (base) to give 7-(cycloheptylmethyl)-6-(4-fluorobenzyl)-3-(tetrahydro-2H-pyran-4-yl)-[1,2,4]triazolo[4,3-a]pyrazin-8(7H)-one (6.00 mg, 2.96% yield). $^1$H NMR (CDCl3 400 MHz): δ7.16-7.06 (m, 4H), 6.65 (s, 1H), 4.13-4.10 (m, 2H), 3.92 (s, 2H), 3.74-3.72 (m, 2H), 3.59-3.54 (m, 2H), 3.13-3.10 (m, 1H), 2.19-2.16 (m, 2H), 2.05-1.95 (m, 1H), 1.94-1.91 (m, 2H), 1.67-1.65 (m, 4H), 1.56-1.51 (m, 4H), 1.40-1.30 (m, 2H), 1.23-1.20 (m, 2H). LC-MS: $t_R$=2.67 min (METHOD 4), m/z=439.2 [M+H]$^+$ Example 61

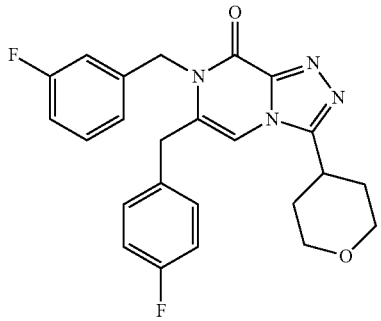 [SMILES: O=c1c2nnc(C3CCOCC3)n2cc(Cc2ccc(F)cc2)n1Cc1cccc(F)c1]

7-(3-fluorobenzyl)-6-(4-fluorobenzyl)-3-(tetrahydro-2H-pyran-4-yl)-[1,2,4]triazolo[4,3-a]pyrazin-8(7H)-one To a suspension of 6-(4-fluorobenzyl)-3-(tetrahydro-2H-pyran-4-yl)-[1,2,4]triazolo[4,3-a]pyrazin-8(7H)-one (150 mg, 456.84 micromol) in anhydrous DMF (5 mL) was added 1-(bromomethyl)-3-fluorobenzene (104 mg, 548.21 micromol) and K$_2$CO$_3$ (95 mg, 685.27 micromol). The mixture was heated at 60° C. for 12 h. LCMS showed 35% of desired product. The mixture was concentrated and the residue was dissolved in DCM (20 mL) and H$_2$O (20 mL). The aqueous layer was extracted with DCM (20 mL). The combined organics were washed with H$_2$O (20 mL), dried over Na$_2$SO$_4$, filtered, concentrated and purified by preparative HPLC (base) to give 7-(3-fluorobenzyl)-6-(4-fluorobenzyl)-3-(tetrahydro-2H-pyran-4-yl)-[1,2,4]triazolo[4,3-a]pyrazin-8(7H)-one (37.90 mg, 19.01% yield). $^1$H NMR (CDCl$_3$ 400 MHz): δ 7.33-7.30 (m, 1H), 7.11-7.08 (m, 4H), 7.00-6.95 (m, 1H), 6.93-6.92 (m, 1H), 6.85-6.80 (m, 1H), 6.74 (s, 1H), 5.16 (s, 2H), 4.16-4.11 (m, 2H), 3.78 (s, 2H), 3.60-3.54 (m, 2H), 3.17-3.14 (m, 1H), 2.25-2.16 (m, 2H), 1.97-1.93 (m, 2H). LC-MS: $t_R$=2.75 min (METHOD 3), m/z=437.2 [M+H]$^+$ Example 62

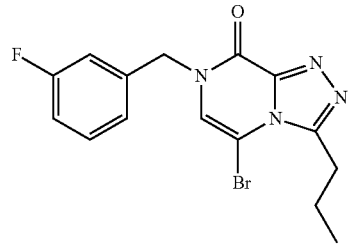 [SMILES: CCCc1nnc2c(=O)n(Cc3cccc(F)c3)cc(Br)n12]

5-bromo-7-(3-fluorobenzyl)-3-propyl-[1,2,4]triazolo[4,3-a]pyrazin-8(7H)-one

Step 1:
A solution of 3,5-dibromopyrazin-2-amine (40 g, 158.17 mmol), isopentyl nitrite (56 g, 474.51 mmol) and HCl/MeOH (8 mL, 1M) in MeOH (400 mL) was stirred at 60° C. for 3 h. The solution was concentrated under vacuum. The residue was diluted with DCM (150 mL), washed with NaHCO$_3$(aq.) until pH=7, dried over Na$_2$SO$_4$ and concentrated under vacuum. The residue was purified by flash chromatography on silica gel (ethyl acetate/petroleums ether=0/1~1/20) to give 3,5-dibromo-2-methoxypyrazine (46 g, Yield: 96.4%) as a yellow liquid.
Step 2:
A solution of 3,5-dibromo-2-methoxypyrazine (45 g, 0.167 mol) and NH$_2$NH$_2$.H$_2$O (15.7 g, 0.252 mol, 80%) in EtOH (250 mL) was stirred at 70° C. for 5 hours. The mixture was concentrated under vacuum, the residue was washed with water, filtered and dried to give 5-bromo-3-hydrazinyl-2-methoxypyrazine (32 g, Yield: 86.9%).
Step 3:
A solution of 5-bromo-3-hydrazinyl-2-methoxypyrazine (5 g, 22.83 mmol) and butyraldehyde (1.73 g, 23.97 mmol) in DCM (60 mL) was stirred at 50° C. for 2 hours. The solution was cooled to 0° C. and iodobenzene diacetate (8.45 g, 26.23 mmol) was portionwise added and the reaction mixture was stirred at 30° C. for 2 hours. Then Na₂CO₃ (20 mL, sat. aq.) was slowly poured into the reaction mixture and stirred for 30 min. The organic phase was separated and washed with brine, dried over Na₂SO₄ and evaporated under reduced pressure. The crude was purified by flash chromatography on silica gel (EA/PE=1/10~1/1) to give 5-bromo-8-methoxy-3-propyl-[1,2,4]triazolo[4,3-a]pyrazine (2 g, Yield: 32.4%).

Step 4:

A solution of 5-bromo-8-methoxy-3-propyl-[1,2,4]triazolo[4,3-a]pyrazine (3.7 g, 13.6 mmol) in DCM (260 mL) was added BBr₃ (17.1 g, 68.2 mmol, 80%) at 0° C. and stirred at 20° C. for 12 hours. The solution was quenched with water (100 mL) and stirred at 20° C. for 0.5 hour. NaHCO₃ (sat. aq.) was added until pH=8. It was filtered and the filtrate was concentrated under vacuum. The residue was diluted with DCM (200 mL), filtered and concentrated under vacuum to give 5-bromo-3-propyl-[1,2,4]triazolo[4,3-a]pyrazin-8(7H)-one (2.6 g, Yield: 74%).

Step 5:

A mixture of 5-bromo-3-propyl-[1,2,4]triazolo[4,3-a]pyrazin-8(7H)-one (2.0 g, 7.78 mmol), 1-(bromomethyl)-3-fluorobenzene (1.47 g, 7.78 mmol) and K₂CO₃ (2.15 g, 15.56 mmol) in DMF (60 mL) was stirred at 60° C. for 5 hours. The mixture was diluted with water (80 mL) and extracted with EA (50 mL*3). The combined organic layers were dried over Na₂SO₄ and evaporated. The residue was washed with MTBE (2, two times 0 mL) to give 5-bromo-7-(3-fluorobenzyl)-3-propyl-[1,2,4]triazolo[4,3-a]pyrazin-8(7H)-one (2 g, yield: 71.4%). ¹H NMR (CDCl3, 400 MHz TMS): δ 7.39-7.34 (m, 1H), 7.15-7.13 (m, 1H), 7.09-7.05 (m, 2H), 6.67 (s, 1H), 5.11 (s, 2H), 3.30 (t, J=7.6 Hz, 2H), 1.99-1.89 (m, 2H), 1.08 (t, J=7.6 Hz, 3H). LC-MS: $t_R$=2.069 min (METHOD 3), m/z=365.0 [M+H]⁺

Example 63

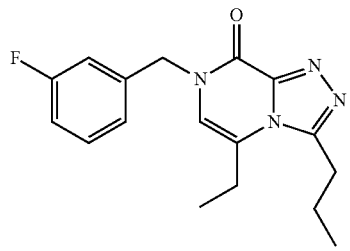 [SMILES: CCCc1nnc2c(=O)n(Cc3cccc(F)c3)cc(CC)n12]

5-ethyl-7-(3-fluorobenzyl)-3-propyl-[1,2,4]triazolo[4,3-a]pyrazin-8(7H)-one

Step 1:

A mixture of 5-bromo-7-(3-fluorobenzyl)-3-propyl-[1,2,4]triazolo[4,3-a]pyrazin-8(7H)-one (150 mg, 410.73 micromol), 4,4,5,5-tetramethyl-2-vinyl-1,3,2-dioxaborolane (127 mg, 821.47 micromol) and K₂CO₃ (170 mg, 1.23 mmol) in THF/H₂O (2 mL/1 mL) was stirred at 80° C. for 12 hours. The mixture was cooled to 20° C., and concentrated in reduced pressure at 30° C. The residue was poured into water (10 mL) and stirred for 20 min. The aqueous phase was extracted with EA (10 mL*3). The combined organic phase was washed with saturated brine (5 mL), dried with anhydrous Na₂SO₄, filtered and concentrated in vacuum to afford 7-(3-fluorobenzyl)-3-propyl-5-vinyl-[1,2,4]triazolo[4,3-a]pyrazin-8(7H)-one (110 mg, 85.74% yield). LC-MS: $t_R$=0.693 min (Method 7), m/z=312.9 [M+H]⁺.

Step 2:

To a solution of 7-(3-fluorobenzyl)-3-propyl-5-vinyl-[1,2,4]triazolo[4,3-a]pyrazin-8(7H)-one (100 mg, 320.16 micromol) in MeOH (5 mL) was added Pd/C (10 mg, 10% Pd, 50% water) under N₂. The suspension was degassed under vacuum and purged with H₂ several times. The mixture was stirred under H₂ (balloon) at 20° C. for 10 min. The mixture filtered and concentrated in reduced pressure at 30° C. The residue was purified by prep-TLC (DCM/MeOH=12/1) to afford 5-ethyl-7-(3-fluorobenzyl)-3-propyl-[1,2,4]triazolo[4,3-a]pyrazin-8(7H)-one (24.3 mg, 23% yield). ¹H NMR (CDCl₃, 400 MHz TMS): δ7.37-7.31 (m, 1H), 7.14-7.11 (m, 1H), 7.05-7.01 (m, 2H), 6.20 (s, 1H), 5.11 (s, 2H), 3.12 (t, J=7.6 Hz, 2H), 2.89-2.83 (m, 2H), 2.01-1.92 (m, 2H), 1.27 (t, J=7.2 Hz, 3H), 1.08 (t, J=7.2 Hz, 3H). LC-MS: $t_R$=2.595 min (METHOD 3), m/z=315.1 [M+H]⁺

Example 64

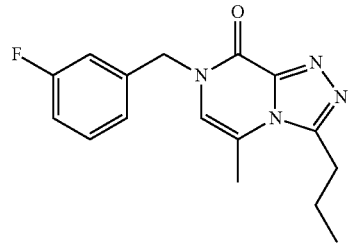 [SMILES: CCCc1nnc2c(=O)n(Cc3cccc(F)c3)cc(C)n12]

7-(3-fluorobenzyl)-5-methyl-3-propyl-[1,2,4]triazolo[4,3-a]pyrazin-8(7H)-one

A mixture of 5-bromo-7-(3-fluorobenzyl)-3-propyl-[1,2,4]triazolo[4,3-a]pyrazin-8(7H)-one (200 mg, 547.65 micromol) and trifluoro(methyl)-borane, potassium salt (200 mg, 1.64 mmol) in Dioxane/H₂O (10 mL/3 mL), was added 1,1'-Bis(diphenylphosphino)ferrocene-palladium(II)dichloride (40 mg, 54.76 micromol). The brownness solution was stirred at 90° C. for 12 hours. The mixture was concentrated under vacuum, the residue was purified by column chromatography (column height: 250 mm, diameter: 100 mm, 100-200 mesh silica gel, Petroleum ether/Ethyl acetate=10/1, 3/1) and followed by prep-HPLC to afford 7-(3-fluorobenzyl)-5-methyl-3-propyl-[1,2,4]triazolo[4,3-a]pyrazin-8(7H)-one (25.5 mg, 15% yield). ¹H NMR (CDCl₃, 400 MHz TMS): δ. 7.35-7.31 (m, 1H), 7.13-7.12 (m, 1H), 7.05-7.02 (m, 2H), 6.23 (s, 1H), 5.09 (s, 2H), 3.14 (t, J=7.6 Hz, 2H), 2.49 (s, 3H), 1.99-1.90 (m, 2H), 1.08 (t, J=7.2 Hz, 3H). LC-MS: $t_R$=2.448 min (METHOD 3), m/z=301.1 [M+H]⁺

Example 65

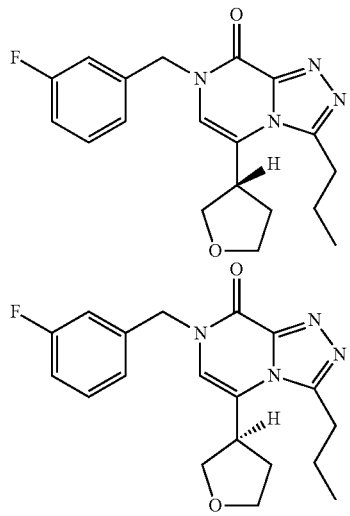

7-(3-fluorobenzyl)-3-propyl-5-(tetrahydrofuran-3-yl)-[1,2,4]triazolo[4,3-a]pyrazin-8(7H)-one, stereoisomer 1 and 2

Step 1:

A mixture of 5-bromo-7-(3-fluorobenzyl)-3-propyl-[1,2,4]triazolo[4,3-a]pyrazin-8(7H)-one (400 mg, 1.10 mmol) and 2-(2,5-dihydrofuran-3-yl)-4,4,5,5-tetramethyl-1,3,2-dioxaborolane (237 mg, 1.21 mmol) in Dioxane/H$_2$O (5 mL/1 mL), was added 1,1'-Bis(diphenylphosphino)ferrocene-palladium(II)dichloride (80 mg, 109.53 micromol) and stirred at 70° C. for 5 hours. The mixture was concentrated under vacuum. The residue was purified by silica gel chromatography (column height: 250 mm, diameter: 100 mm, 100-200 mesh silica gel, Petroleum ether/Ethyl acetate=10/1, 1/1) and followed by preparative HPLC to afford 5-(2,5-dihydrofuran-3-yl)-7-(3-fluorobenzyl)-3-propyl-[1,2,4]triazolo[4,3-a]pyrazin-8(7H)-one (100 mg, 25.65% yield) as white solid.

Step 2:

To a solution of 5-(2,5-dihydrofuran-3-yl)-7-(3-fluorobenzyl)-3-propyl-[1,2,4]triazolo[4,3-a]pyrazin-8(7H)-one (90 mg, 253.96 micromol) in MeOH (6 mL) was added Pd/C (10 mg, 10% Pd, 50% water) under N$_2$. The suspension was degassed under vacuum and purged with H$_2$ several times. The mixture was stirred under H$_2$ (balloon) at 20° C. for 1 hour. The mixture was filtered and concentrated in reduced pressure at 30° C. The residue was purified by prep-TLC (EA/PE=1/0) to afford 7-(3-fluorobenzyl)-3-propyl-5-(tetrahydrofuran-3-yl)-[1,2,4]triazolo[4,3-a]pyrazin-8(7H)-one (60 mg, 65% yield) as white solid. LC-MS: $t_R$=0.659 min (Method 7), m/z=356.9 [M+H]$^+$.

Step 3:

7-(3-fluorobenzyl)-3-propyl-5-(tetrahydrofuran-3-yl)-[1,2,4]triazolo[4,3-a]pyrazin-8(7H)-one (60 mg, 168.35 micromol) was purified by SFC to give 7-(3-fluorobenzyl)-3-propyl-5-(tetrahydrofuran-3-yl)-[1,2,4]triazolo[4,3-a]pyrazin-8(7H)-one, stereoisomer 1 (15.10 mg, 25% yield)$^1$H NMR (CDCl$_3$ varian 400): δ 7.37-7.31 (m, 1H), 7.13-7.11 (m, 1H), 7.05-7.01 (m, 2H), 6.47 (s, 1H), 5.16-5.06 (m, 2H), 3.93-3.89 (m, 4H), 3.68-3.71 (m, 1H), 3.18-3.06 (m, 2H), 2.44-2.39 (m, 1H), 2.03-1.96 (m, 3H), 1.10 (t, J=7.6 Hz, 3H). LC-MS: $t_R$=2.423 min (METHOD 3), m/z=357.2 [M+H]$^+$. SFC: $t_R$=10.2 min, ee %=100%. $[\alpha]_D^{20}$=+81.67° (c=0.10, CHCl$_3$).

And 7-(3-fluorobenzyl)-3-propyl-5-(tetrahydrofuran-3-yl)-[1,2,4]triazolo[4,3-a]pyrazin-8(7H)-one, stereoisomer 2_10 (18.70 mg, 30% yield)$^1$H NMR (CDCl$_3$ varian 400): δ 7.37-7.31 (m, 1H), 7.13-7.11 (m, 1H), 7.05-7.01 (m, 2H), 6.47 (s, 1H), 5.16-5.06 (m, 2H), 4.00-3.95 (m, 4H), 3.81-3.69 (m, 1H), 3.18-3.08 (m, 2H), 2.44-2.39 (m, 1H), 2.03-1.96 (m, 3H), 1.10 (t, J=7.6 Hz, 3H). LC-MS: $t_R$=2.424 min (METHOD 3), m/z=357.1 [M+H]$^+$. SFC: $t_R$=10.76 min, ee %=97.89%. $[\alpha]_D^{20}$=−81.67 (c=0.10, CHCl$_3$).

Example 66

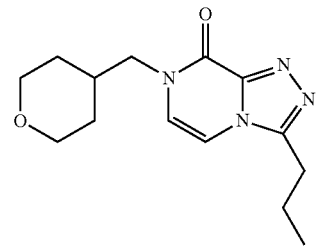 [SMILES: CCCc1nnc2c(=O)n(CC3CCOCC3)ccn12]

3-propyl-7-((tetrahydro-2H-pyran-4-yl)methyl)-[1,2,4]triazolo[4,3-a]pyrazin-8(7H)-one To a solution of 3-propyl-[1,2,4]triazolo[4,3-a]pyrazin-8(7H)-one (200 mg, 1.1 mmol) and 4-(bromomethyl)tetrahydro-2H-pyran (241 mg, 1.35 mmol) in DMF (2 mL) was added K$_2$CO$_3$ (310 mg, 2.2 mmol). The mixture was stirred at 60° C. for 4 hours. The mixture was diluted with DCM (20 mL) and washed with water (5 mL, two times). The organic layer was dried over Na$_2$SO$_4$ and evaporated. The residue was washed with MeOH (2 mL) to give 3-propyl-7-((tetrahydro-2H-pyran-4-yl)methyl)-[1,2,4]triazolo[4,3-a]pyrazin-8(7H)-one (120 mg, yield: 54%). $^1$H NMR (CDCl$_3$, 400 MHz TMS): δ 6.91 (d, J=6.0 Hz, 1H), 6.62 (d, J=6.0 Hz, 1H), 3.96 (dd, J=11.6, 3.2 Hz, 2H), 3.82 (d, J=7.6 Hz, 2H), 3.34 (td, J=11.6, 1.6 Hz, 2H), 2.94 (t, J=7.6 Hz, 2H), 2.20-2.10 (m, 1H), 1.91-1.86 (m, 2H), 1.61-1.58 (m, 2H), 1.40 (dq, J=4.0, 12.0 Hz, 2H), 1.04 (t, J=7.6 Hz, 3H). LC-MS: $t_R$=1.93 min (METHOD 3), m/z=277.1 [M+H]$^+$.

Example 67

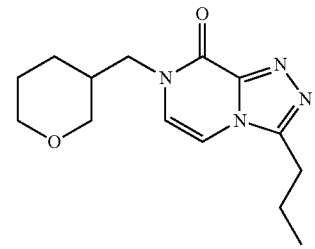 [SMILES: CCCc1nnc2c(=O)n(CC3CCCOC3)ccn12]

3-propyl-7-((tetrahydro-2H-pyran-3-yl)methyl)-[1,2,4]triazolo[4,3-a]pyrazin-8(7H)-one, stereoisomer 1 and 2

Step 1:

To a solution of (tetrahydro-2H-pyran-3-yl)methanol (300 mg, 2.58 mmol) and TEA (522 mg, 5.17 mmol) in DCM (10 mL) was added MsCl (355 mg, 3.10 mmol) at 0° C. and it was stirred at 20° C. for 1 hours. The solution was washed with NaHCO$_3$ (aq. 2 mL), water (three times 2 mL), brine (1 time 1 mL) dried and concentrated to give (tetrahydro-2H-pyran-3-yl)methyl methanesulfonate (500 mg), which was used in the next step directly.

Step 2:

To a solution of (tetrahydro-2H-pyran-3-yl)methyl methanesulfonate (500 mg, 2.58 mmol) and 3-propyl-[1,2,4]triazolo[4,3-a]pyrazin-8(7H)-one (413 mg, 2.32 mmol) in DMF (30 mL) was added K$_2$CO$_3$ (534 mg, 3.87 mmol). The mixture was stirred at 60° C. for 4 hours. The mixture was diluted with DCM (100 mL) and washed with water (2 times 10 mL). The organic layer was dried over Na$_2$SO$_4$ and evaporated. The residue was washed with MeOH (2 mL) to give 3-propyl-7-((tetrahydro-2H-pyran-3-yl)methyl)-[1,2,4]triazolo[4,3-a]pyrazin-8(7H)-one (400 mg, yield: 56%).

Step 3:

3-propyl-7-((tetrahydro-2H-pyran-3-yl)methyl)-[1,2,4]triazolo[4,3-a]pyrazin-8(7H)-one (400 mg, 1.45 mmol) was purified by SFC to afford 3-propyl-7-((tetrahydro-2H-pyran-3-yl)methyl)-[1,2,4]triazolo[4,3-a]pyrazin-8(7H)-one, stereoisomer 1(160 mg, yield: 40.0%), $^1$H NMR (CDCl$_3$ varian 400): δ 6.93 (d, J=6.0 Hz, 1H), 6.66 (d, J=6.0 Hz, 1H), 4.03-3.94 (m, 1H), 3.89-3.74 (m, 3H), 3.60-3.50 (m, 1H), 3.37 (dd, J=11.6, 7.6 Hz, 1H), 2.97 (t, J=7.6 Hz, 2H), 2.23-2.12 (m, 1H), 1.97-1.80 (m, 3H), 1.78-1.68 (m, 1H), 1.62-1.53 (m, 1H), 1.50-1.40 (m, 1H), 1.06 (t, J=7.4 Hz, 3H). LC-MS: $t_R$=1.99 min (METHOD 3), m/z=277.2 [M+H]$^+$. SFC-MS: $t_R$=9.60 min, ee %=99.68%. [α]D$^{20}$=−11.33 (c=0.10, MeOH).

And 3-propyl-7-((tetrahydro-2H-pyran-3-yl)methyl)-[1,2,4]triazolo[4,3-a]pyrazin-8(7H)-one, stereoisomer 2 (170 mg, yield: 42.5%). $^1$H NMR (CDCl$_3$ varian 400): δ6.94 (d, J=6.0 Hz, 1H), 6.66 (d, J=6.4 Hz, 1H), 4.01-3.94 (m, 1H), 3.89-3.74 (m, 3H), 3.60-3.51 (m, 1H), 3.37 (dd, J=11.6, 7.6 Hz, 1H), 2.97 (t, J=7.6 Hz, 2H), 2.23-2.12 (m, 1H), 1.78-1.68 (m, 1H), 1.62-1.53 (m, 1H), 1.50-1.40 (m, 1H), 1.06 (t, J=7.4 Hz, 3H). LC-MS: $t_R$=1.99 min (METHOD 3), m/z=277.2 [M+H]+. SFC-MS: $t_R$=10.81 min, ee %=99.50%. [α]D$^{20}$=+12.33° (c=0.10, MeOH).

Example 68

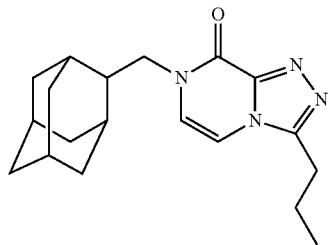 [SMILES: CCCc1nnc2c(=O)n(CC3C4CC5CC(C4)CC3C5)ccn12]

7-(((1r,3r,5r,7r)-adamantan-2-yl)methyl)-3-propyl-[1,2,4]triazolo[4,3-a]pyrazin-8(7H)-one Step 1:

Borane-tetrahydrofurane complex (1 M, 4.44 mL, 2.00 Eq) was added dropwise to a solution of (1 r,3r,5r,7r)-adamantane-2-carboxylic acid (400 mg, 2.22 mmol, 1.00 Eq) in THF (15 mL) at 0° C. Then the mixture was heated at 60° C. for 12 h. The mixture was cooled to 0° C. and MeOH (3 mL) was added dropwise to the mixture. The mixture was concentrated and the residue was purified by flash chromatography on silica gel (DCM/MeOH=100/1-20/1) to give ((1 r,3r,5r,7r)-adamantan-2-yl)methanol (250.00 mg, 1.35 mmol, 60.96% yield, 90% purity).

Step 2:

To a cooled (0° C.) solution of ((1 r,3r,5r,7r)-adamantan-2-yl)methanol (250 mg, 1.50 mmol, 1.00 Eq) in DCM (10 mL) was added Et$_3$N (304 mg, 3.01 mmol, 2.00 Eq) and MsCl (207 mg, 1.80 mmol, 1.20 Eq). The mixture was stirred at 0° C. for 1 h. The reaction was checked by TLC. Water (5 mL) was added to the mixture. The organic layer was dried over Na$_2$SO$_4$, filtered and concentrated to give ((1 r,3r,5r,7r)-adamantan-2-yl)methyl methanesulfonate (350 mg, 95.49% yield) as a light yellow oil.

Step 3:

To a suspension of 3-propyl-[1,2,4]triazolo[4,3-a]pyrazin-8(7H)-one (200 mg, 1.12 mmol, 1.00 Eq) in DMF (10 mL) was added ((1 r,3r,5r,7r)-adamantan-2-yl)methyl methanesulfonate (328 mg, 1.34 mmol, 1.20 Eq) and K$_2$CO$_3$ (310 mg, 2.24 mmol, 2.00 Eq). The mixture was heated at 70° C. for 48 h. The reaction was checked by LCMS. The mixture was concentrated and the residue was dissolved in DCM (10 mL) and H$_2$O (10 mL). The organic layer was dried over Na$_2$SO$_4$, filtered and concentrated and purified by prep. TLC (DCM/MeOH=50/1) to give 7-(((1 r,3r,5r,7r)-adamantan-2-yl)methyl)-3-propyl-[1,2,4]triazolo[4,3-a]pyrazin-8(7H)-one (9.00 mg, 2.46% yield). $^1$H NMR (CDCl3 400 MHz): δ 6.90 (d, J=6.0 Hz, 1H), 6.64 (d, J=6.0 Hz, 1H), 4.10 (d, J=8.0 Hz, 2H), 2.95 (t, J=7.2 Hz, 2H), 2.17-2.10 (m, 1H), 2.05-2.00 (m, 2H), 1.93-1.84 (m, 6H), 1.75-1.64 (m, 6H), 1.61-1.59 (m, 2H), 1.06 (t, J=7.2 Hz, 3H). LC-MS: $t_R$=2.26 min (METHOD 4), m/z=327.2 [M+H]$^+$.

Example 69

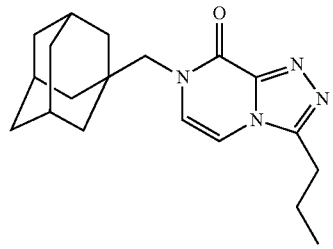 [SMILES: CCCc1nnc2c(=O)n(CC34CC5CC(CC(C5)C3)C4)ccn12]

7-(((3r,5r,7r)-adamantan-1-yl)methyl)-3-propyl-[1,2,4]triazolo[4,3-a]pyrazin-8(7H)-one Step 1:

To a cooled (0° C.) solution of ((3r,5r,7r)-adamantan-1-yl)methanol (250 mg, 1.50 mmol) in DCM (10 mL) was added Et$_3$N (304 mg, 3.01 mmol) and MsCl (207 mg, 1.80 mmol). The mixture was stirred at 0° C. for 1 h. The reaction was checked by TLC. Water (5 mL) was added to the mixture. The organic layer was dried over Na$_2$SO$_4$, filtered and concentrated to give ((3r,5r,7r)-adamantan-1-yl)methyl methanesulfonate (350 mg, 95.49% yield).

Step 2:

To a suspension of 3-propyl-[1,2,4]triazolo[4,3-a]pyrazin-8(7H)-one (160 mg, 897.92 micromol) in DMF (5 mL) was added ((3r,5r,7r)-adamantan-1-yl)methyl methanesulfonate (263 mg, 1.08 mmol) and K$_2$CO$_3$ (248 mg, 1.80 mmol). The mixture was heated at 100° C. for 20 h. The mixture was concentrated and the residue was dissolved in DCM (10 mL) and H$_2$O (10 mL). The organic layer was dried over Na$_2$SO$_4$, filtered and concentrated to give the crude product. The crude product was washed with MeOH (10 mL) to give 7-(((3r,5r,7r)-adamantan-1-yl)methyl)-3-propyl-[1,2,4]triazolo[4,3-a]pyrazin-8(7H)-one (51 mg, 17.43% yield). $^1$H NMR (CDCl$_3$ 400 MHz): δ 6.85 (d, J=5.6 Hz, 1H), 6.59 (d, J=6.0 Hz, 1H), 3.68 (s, 2H), 2.96 (t, J=7.2 Hz, 2H), 2.00 (s, 3H), 1.94-1.89 (m, 2H), 1.72-1.63 (m, 12H), 1.07 (t, J=7.2 Hz, 3H). LC-MS: t$_R$=3.07 min (method 9), m/z=327.1 [M+H]$^+$.

Example 70

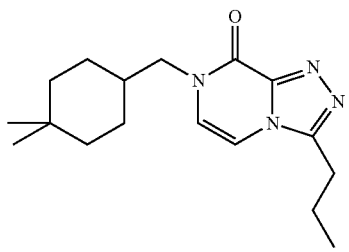 [SMILES: CCCc1nnc2c(=O)n(CC3CCC(C)(C)CC3)ccn12]

7-((4,4-dimethylcyclohexyl)methyl)-3-propyl-[1,2,4]triazolo[4,3-a]pyrazin-8(7H)-one To a suspension of 3-propyl-[1,2,4]triazolo[4,3-a]pyrazin-8(7H)-one (200 mg, 1.12 mmol) in DMF (5 mL) was added 4-(bromomethyl)-1,1-dimethylcyclohexane (276 mg, 1.35 mmol, 1.20 Eq) and K$_2$CO$_3$ (310 mg, 2.24 mmol, 2.00 Eq). The mixture was heated at 60° C. for 12 h. The mixture was concentrated and the residue was dissolved in DCM (10 mL) and H$_2$O (10 mL). The organic layer was dried over Na$_2$SO$_4$, filtered and concentrated to give the crude product. The crude product was washed with MeOH (10 mL) to give 7-((4,4-dimethylcyclohexyl)methyl)-3-propyl-[1,2,4]triazolo[4,3-a]pyrazin-8(7H)-one (102 mg, 30% yield). $^1$H NMR (CDCl$_3$ 400 MHz): δ 6.90 (d, J=6.0 Hz, 1H), 6.62 (d, J=6.0 Hz, 1H), 3.83 (d, J=7.2 Hz, 2H), 2.95 (t, J=7.6 Hz, 2H), 1.93-1.88 (m, 2H), 1.80-1.70 (m, 1H), 1.50-1.42 (m, 2H), 1.33-1.39 (m, 2H), 1.25-1.14 (m, 4H), 1.06 (t, J=7.6 Hz, 3H), 0.89 (s, 6H). LC-MS: t$_R$=2.84 min (METHOD 3), m/z=303.2 [M+H]$^+$.

Example 71

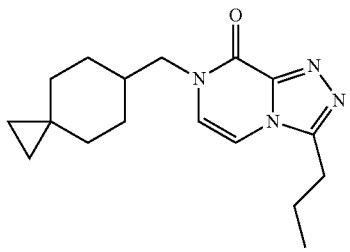 [SMILES: CCCc1nnc2c(=O)n(CC3CCC4(CC3)CC4)ccn12]

3-propyl-7-(spiro[2.5]octan-6-ylmethyl)-[1,2,4]triazolo[4,3-a]pyrazin-8(7H)-one

Step 1:

To a cooled (0° C.) solution of spiro[2.5]octan-6-ylmethanol (200 mg, 1.43 mmol) in DCM (10 mL) was added Et$_3$N (289 mg, 2.86 mmol) and MsCl (197 mg, 1.72 mmol). The mixture was stirred at 0° C. for 1 hr. The reaction was checked by TLC. Water (5 mL) was added to the mixture. The organic layer was dried over Na$_2$SO$_4$, filtered and concentrated to give spiro[2.5]octan-6-ylmethyl methanesulfonate (310 mg, 99.3% yield) as a light yellow oil.

Step 2:

To a suspension of 3-propyl-[1,2,4]triazolo[4,3-a]pyrazin-8(7H)-one (200 mg, 1.12 mmol) in DMF (5 mL) was added spiro[2.5]octan-6-ylmethyl methanesulfonate (293 mg, 1.34 mmol) and K$_2$CO$_3$ (310 mg, 2.24 mmol). The mixture was heated at 60° C. for 12 h. The mixture was concentrated and the residue was dissolved in DCM (10 mL) and H$_2$O (10 mL). The organic layer was dried over Na$_2$SO$_4$, filtered and concentrated to give the crude product. The crude product was washed with MeOH (10 mL) to give 3-propyl-7-(spiro[2.5]octan-6-ylmethyl)-[1,2,4]triazolo[4,3-a]pyrazin-8(7H)-one (90 mg, 27% yield). $^1$H NMR (CDCl3 400 MHz): δ 6.91 (d, J=6.0 Hz, 1H), 6.63 (d, J=6.0 Hz, 1H), 3.84 (d, J=7.6 Hz, 2H), 2.95 (t, J=7.6 Hz, 2H), 1.93-1.88 (m, 3H), 1.69-1.65 (m, 4H), 1.25-1.43 (m, 2H), 1.06 (t, J=7.6 Hz, 3H), 0.92-0.88 (m, 2H), 0.29-0.26 (m, 2H), 0.20-0.18 (m, 2H). LC-MS: t$_R$=2.71 min (METHOD 3), m/z=301.2 [M+H]$^+$.

Example 72

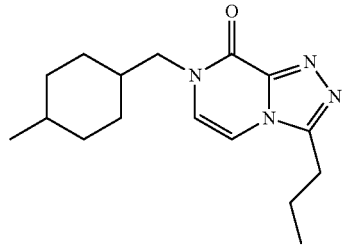 [SMILES: CCCc1nnc2c(=O)n(CC3CCC(C)CC3)ccn12]

7-((4-methylcyclohexyl)methyl)-3-propyl-[1,2,4]triazolo[4,3-a]pyrazin-8(7H)-one

Step 1:

To a cooled (0° C.) solution of (4-methylcyclohexyl)methanol (250 mg, 1.95 mmol) in DCM (10 mL) was added TEA (395 mg, 3.90 mmol) and MsCl (268.05 mg, 2.34 mmol). The mixture was stirred at 0° C. for 1 hr. Water (5 mL) was added to the mixture. The organic layer was dried over Na$_2$SO$_4$, filtered and concentrated to give (4-methylcyclohexyl)methyl methanesulfonate (400 mg, 99% yield) as a light yellow oil.

Step 2:

To a suspension of 3-propyl-[1,2,4]triazolo[4,3-a]pyrazin-8(7H)-one (250 mg, 1.40 mmol) in DMF (5 mL) was added (4-methylcyclohexyl)methyl methanesulfonate (376 mg, 1.82 mmol) and K$_2$CO$_3$ (388 mg, 2.81 mmol). The mixture was heated at 60° C. for 12 h. The mixture was concentrated and the residue was dissolved in DCM (10 mL) and H$_2$O (10 mL). The organic layer was dried over Na$_2$SO$_4$, filtered and concentrated to give the crude product. The crude product was washed with MeOH (10 mL) to give 7-((4-methylcyclohexyl)methyl)-3-propyl-[1,2,4]triazolo[4,3-a]pyrazin-8(7H)-one (69 mg, 17.09% yield). $^1$H NMR (CDCl3 400 MHz): δ 6.90 (dd, J=6.0, 2.0 Hz, 1H), 6.62 (t, J=6.0 Hz, 1H), 3.90 (d, J=7.6 Hz, 1H), 3.80 (d, J=7.2 Hz, 1H), 2.95 (t, J=7.6 Hz, 2H), 1.93-1.88 (m, 2H), 1.72-1.69 (m, 2H), 1.49-1.47 (m, 2H), 1.45-1.30 (m, 2H), 1.08-1.04 (m, 5H), 0.96-0.86 (m, 5H). LC-MS: $t_R$=2.70 min (METHOD 3), m/z=289.2 [M+H]$^+$.

The two diastereoisomers, cis and trans, was separated by SFC, to yield 7-(((1s,4s)-4-methylcyclohexyl)methyl)-3-propyl-[1,2,4]triazolo[4,3-a]pyrazin-8(7H)-one and 7-(((1r,4r)-4-methylcyclohexyl)methyl)-3-propyl-[1,2,4]triazolo[4,3-a]pyrazin-8(7H)-one.

Example 73

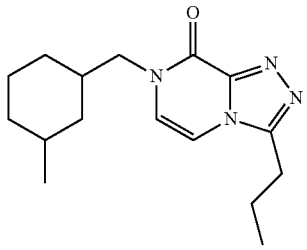 [SMILES: CCCc1nnc2c(=O)n(CC3CCCC(C)C3)ccn12]

7-((3-methylcyclohexyl)methyl)-3-propyl-[1,2,4]triazolo[4,3-a]pyrazin-8(7H)-one

Step 1:

Borane-tetrahydrofuran complex (1 M, 7.03 mL, 2.00 Eq) was added dropwise to a solution of 3-methylcyclohexane-1-carboxylic acid (500 mg, 3.52 mmol) in THF (15 mL) at 0° C. Then the mixture was heated at 60° C. for 12 h. The mixture was cooled to 0° C. and MeOH (3 mL) was added dropwise to the mixture. The mixture was concentrated and the residue was purified by flash chromatography on silica gel (petroleumsether/ethyl acetate=50/1-10/1) to give (3-methylcyclohexyl)methanol (440 mg, 97.50% yield) as a colorless oil.

Step 2:

To a cooled (0° C.) solution of (3-methylcyclohexyl)methanol (200 mg, 1.56 mmol) in DCM (10 mL) was added Et$_3$N (316 mg, 3.12 mmol) and MsCl (790 mg, 6.90 mmol). The mixture was stirred at 0° C. for 1 h. The reaction was checked by TLC. Water (5 mL) was added to the mixture. The organic layer was dried over Na$_2$SO$_4$, filtered and concentrated to give (3-methylcyclohexyl)methyl methanesulfonate (320 mg, 99.43% yield) as a yellow oil.

Step 3:

To a suspension of 3-propyl-[1,2,4]triazolo[4,3-a]pyrazin-8(7H)-one (200 mg, 1.12 mmol) in DMF (5 mL) was added (3-methylcyclohexyl)methyl methanesulfonate (278 mg, 1.35 mmol) and K$_2$CO$_3$ (310 mg, 2.24 mmol). The mixture was heated at 60° C. for 12 h. The mixture was concentrated and the residue was dissolved in DCM (10 mL) and H$_2$O (10 mL). The organic layer was dried over Na$_2$SO$_4$, filtered, concentrated and purified by prep. TLC (DCM/MeOH=50/1) to give 7-((3-methylcyclohexyl)methyl)-3-propyl-[1,2,4]triazolo[4,3-a]pyrazin-8(7H)-one as a mixture of cis/trans isomers (119.20 mg, 413 micromol, 36% yield). $^1$H NMR (CDCl3 varian 400): δ 6.90 (d, J=5.6 Hz, 1H), 6.61 (d, J=6.0 Hz, 1H), 3.91-3.84 (m, 0.48 H), 3.76 (d, J=7.6 Hz, 1.52H), 2.95 (t, J=7.6 Hz, 2H), 2.21-2.05 (m, 0.2H), 1.92-1.84 (m, 3H), 1.77-1.70 (m, 1.3H), 1.62-1.45 (m, 1.7H), 1.41-1.15 (m, 3H), 1.04 (t, J=7.6 Hz, 3H), 0.95-0.85 (m, 5H), 0.68-0.65 (m, 0.8H). LC-MS: $t_R$=2.70 min (METHOD 3), m/z=289.2 [M+H]$^+$.

Example 74

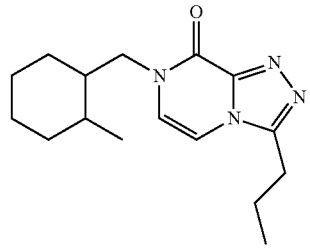 [SMILES: CCCc1nnc2c(=O)n(CC3CCCCC3C)ccn12]

7-((2-methylcyclohexyl)methyl)-3-propyl-[1,2,4]triazolo[4,3-a]pyrazin-8(7H)-one

Step 1:

Borane-tetrahydrofuran complex (1 M, 7.03 mL, 2.00 Eq) was added dropwise to a solution of 3-methylcyclohexane-1-carboxylic acid (500.00 mg, 3.52 mmol, 1.00 Eq) in THF (15 mL) at 0° C. Then the mixture was heated at 60° C. for 12 h. The mixture was cooled to 0° C. and MeOH (3 mL) was added dropwise to the mixture. The mixture was concentrated and the residue was purified by flash chromatography on silica gel (PE/EA=50/1-10/1) to give (3-methylcyclohexyl)methanol (440 mg, 97% yield).

Step 2:

To a cooled (0° C.) solution of (3-methylcyclohexyl)methanol (200 mg, 1.56 mmol) in DCM (5 mL) was added Et$_3$N (316 mg, 3.12 mmol) and methanesulfonyl chloride (214 mg, 1.87 mmol). The mixture was stirred at 0° C. for 1 h. The reaction was checked by TLC. Water (5 mL) was added to the mixture. The organic layer was dried over Na$_2$SO$_4$, filtered and concentrated to give (2-methylcyclohexyl)methyl methanesulfonate (320 mg, 99% yield).

Step 3:

To a suspension of 3-propyl-[1,2,4]triazolo[4,3-a]pyrazin-8(7H)-one (200 mg, 1.12 mmol) in DMF (5 mL) was added (2-methylcyclohexyl)methyl methanesulfonate (277 mg, 1.34 mmol) and K$_2$CO$_3$ (310 mg, 2.24 mmol). The mixture was heated at 60° C. for 12 h. The mixture was concentrated and the residue was dissolved in DCM (10 mL) and H$_2$O (10 mL). The organic layer was dried over Na$_2$SO$_4$, filtered, concentrated and purified by prep-TLC (DCM/MeOH=50/1) to give 7-((2-methylcyclohexyl)methyl)-3-propyl-[1,2,4]triazolo[4,3-a]pyrazin-8(7H)-one as a mixture of cis/trans isomers (89 mg, 27.68% yield). $^1$H NMR (CDCl3 varian 400): δ6.87-6.83 (m, 1H), 6.60-6.53 (m, 1H), 4.12-4.07 (m, 0.3H), 3.92-3.85 (m, 0.1H), 3.81-3.77 (m, 1.3H), 3.68-3.64 (m, 0.3H), 2.89 (t, J=7.2 Hz, 2H), 1.96-0.91 (m, 18H). LC-MS: $t_R$=2.66 min (METHOD 3), m/z=289.2 [M+H]$^+$.

Example 75

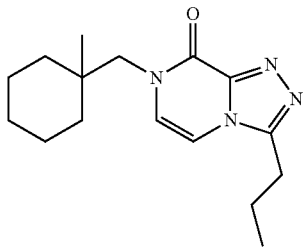 [SMILES: CCCc1nnc2c(=O)n(CC3(C)CCCCC3)ccn12]

7-((1-methylcyclohexyl)methyl)-3-propyl-[1,2,4]
triazolo[4,3-a]pyrazin-8(7H)-one To a suspension of 3-propyl-[1,2,4]triazolo[4,3-a]
pyrazin-8(7H)-one (200 mg, 1.12 mmol) in DMF (5 mL)
was added 1-(bromomethyl)-1-methylcyclohexane (257 mg,
1.34 mmol) and K$_2$CO$_3$ (310 mg, 2.24 mmol). The mixture
was heated at 100° C. for 20 h. The mixture was concentrated and the residue was dissolved in DCM (10 mL) and
H$_2$O (10 mL). The organic layer was dried over Na$_2$SO$_4$,
filtered and concentrated to give the crude product. The
crude product was washed with MeOH (10 mL) to give
7-((1-methylcyclohexyl)methyl)-3-propyl-[1,2,4]triazolo[4,
3-a]pyrazin-8(7H)-one (36 mg, 10.99% yield). $^1$H NMR
(CDCl3 400 MHz): δ 6.86 (d, J=6.4 Hz, 1H), 6.63 (d, J=6.0
Hz, 1H), 3.84 (s, 2H), 2.95 (t, J=7.6 Hz, 2H), 1.94-1.88 (m,
2H), 1.60-1.56 (m, 5H), 1.46-1.38 (m, 5H), 1.06 (t, J=7.6
Hz, 3H), 0.99 (s, 3H). LC-MS: t$_R$=2.66 min (METHOD 3),
m/z=289.2 [M+H]$^+$.

Example 76

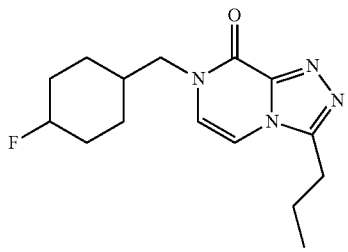 [SMILES: CCCc1nnc2c(=O)n(CC3CCC(F)CC3)ccn12]

7-((4-fluorocyclohexyl)methyl)-3-propyl-[1,2,4]
triazolo[4,3-a]pyrazin-8(7H)-one Step 1:
Borane-tetrahydrofuran complex (1 M, 4.11 mL, 2.00 Eq)
was added dropwise to a solution of 4-fluorocyclohexane-
1-carboxylic acid (300 mg, 2.05 mmol) in THF (15 mL) at
0° C. Then the mixture was heated at 60° C. for 12 h. The
mixture was cooled to 0° C. and MeOH (3 mL) was added
dropwise to the mixture. The mixture was concentrated and
the residue was purified by flash chromatography on silica
gel (PE/EA=50/1-5/1) to give (4-fluorocyclohexyl)methanol
(200 mg, 73.81% yield) as a colorless oil.
Step 2:
To a cooled (0° C.) solution of (4-fluorocyclohexyl)
methanol 2 (200 mg, 1.51 mmol) in DCM (10 mL) was
added TEA (306 mg, 3.03 mmol) and MsCl (208 mg, 1.82
mmol). The mixture was stirred at 0° C. for 1 h. The reaction
was checked by TLC. Water (5 mL) was added to the
mixture. The organic layer was dried over Na$_2$SO$_4$, filtered
and concentrated to give (4-fluorocyclohexyl)methyl methanesulfonate (310 mg, 97.64% yield) as a yellow oil.
Step 3:
To a suspension of 3-propyl-[1,2,4]triazolo[4,3-a]
pyrazin-8(7H)-one (190 mg, 1.07 mmol) in DMF (10 mL)
was added (4-fluorocyclohexyl)methyl methanesulfonate
(269 mg, 1.28 mmol) and K$_2$CO$_3$ (295 mg, 2.13 mmol). The
mixture was heated at 60° C. for 12 h. The mixture was
concentrated and the residue was dissolved in DCM (10 mL)
and H$_2$O (10 mL). The organic layer was dried over Na$_2$SO$_4$,
filtered and concentrated to give the crude product. The
crude product was washed with MeOH (10 mL) to give
7-((4-fluorocyclohexyl)methyl)-3-propyl-[1,2,4]triazolo[4,
3-a]pyrazin-8(7H)-one as a mixture of cis/trans isomers (62
mg, 19.88% yield). $^1$H NMR (CDCl3 400 MHz): δ 6.92
(app. dd, J=6.0, 8.8 Hz, 1H), 6.61 (app. dd, J=4.0, 6.0 Hz,
1H), 4.90-4.78 (m, 0.5H), 4.58-4.40 (m, 0.5H), 3.81 (t, J=7.2
Hz, 2H), 2.96 (t, J=7.6 Hz, 2H), 2.18-1.75 (m, 4H), 1.63-
1.41 (m, 6H), 1.20-1.09 (m, 1H), 1.06 (t, J=7.2 Hz, 3H).
LC-MS: t$_R$=2.26 min (METHOD 3), m/z=293.2 [M+H]$^+$.

Example 77

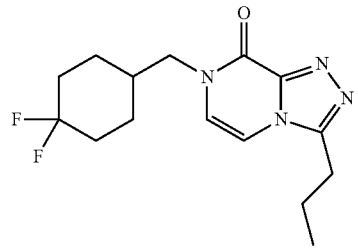

7-((4,4-difluorocyclohexyl)methyl)-3-propyl-[1,2,4]
triazolo[4,3-a]pyrazin-8(7H)-one Step 1:
To a cooled (0° C.) solution of (4,4-difluorocyclohexyl)
methanol (200 mg, 1.33 mmol) in DCM (10 mL) was added
TEA (270 mg, 2.66 mmol) and MsCl (183 mg, 1.60 mmol).
The mixture was stirred at 0° C. for 1 h. The reaction was
checked by TLC. Water (5 mL) was added to the mixture.
The organic layer was dried over Na$_2$SO$_4$, filtered and
concentrated to give (4,4-difluorocyclohexyl)methyl methanesulfonate (300 mg, 98.82% yield).
Step 2:
To a suspension of 3-propyl-[1,2,4]triazolo[4,3-a]
pyrazin-8(7H)-one (200 mg, 1.12 mmol) in DMF (5 mL)
was added (4,4-difluorocyclohexyl)methyl methanesulfonate (307 mg, 1.35 mmol) and K$_2$CO$_3$ (310 mg, 2.24
mmol). The mixture was heated at 60° C. for 12 h. The
mixture was concentrated and the residue was dissolved in
DCM (10 mL) and H$_2$O (10 mL). The organic layer was
dried over Na$_2$SO$_4$, filtered and concentrated to give the
crude product. The crude product was washed with MeOH
(10 mL) to give 7-((4,4-difluorocyclohexyl)methyl)-3-pro-
pyl-[1,2,4]triazolo[4,3-a]pyrazin-8(7H)-one (28 mg, 7.94%
yield). $^1$H NMR (CDCl3 400 MHz): δ 6.93 (d, J=6.0 Hz,
1H), 6.62 (d, J=6.0 Hz, 1H), 3.85 (d, J=7.6 Hz, 2H), 2.96 (t, J=7.6 Hz, 2H), 2.16-2.11 (m, 3H), 1.93-1.88 (m, 2H), 1.79-1.62 (m, 4H), 1.42-1.38 (m, 2H), 1.06 (t, J=7.6 Hz, 3H). LC-MS: $t_R$=2.83 min (method 8), m/z=311.0 [M+H]$^+$.

Example 78

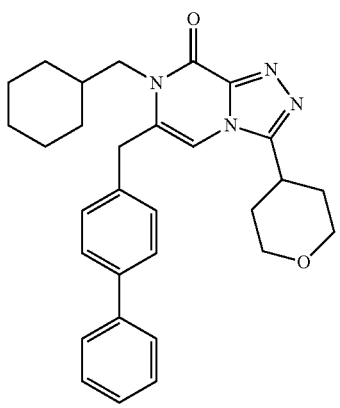 [SMILES: O=c1c2nnc(C3CCOCC3)n2cc(Cc2ccc(-c3ccccc3)cc2)n1CC1CCCCC1]

6-([1,1'-biphenyl]-4-ylmethyl)-7-(cyclohexylmethyl)-3-(tetrahydro-2H-pyran-4-yl)-[1,2,4]triazolo[4,3-a]pyrazin-8(7H)-one Step 1:
6-bromo-8-methoxy-3-(tetrahydro-2H-pyran-4-yl)-[1,2,4]triazolo[4,3-a]pyrazine (225 mg, 0.719 mmol) and Bis(di-tert-butyl(4-dimethylaminophenyl)phosphine)dichloropalladium(II) (A-taPhos)$_2$PdCl$_2$ (90 mg, 0.127 mmol) was dissolved in anhydrous THF (8800 mg, 10 ml, 122 mmol) under argon and degassed for 20 min. ([1,1'-biphenyl]-4-ylmethyl)zinc(II) chloride (4.31 ml, 2.156 mmol, 0.5 molar, THF) was added dropwise and the reaction was stirred overnight. The reaction mixture was poured into aq. sat. NH$_4$Cl (10 mL) and extracted with ethyl acetate (20 mL). The water phase was re-extracted with ethyl acetate (10 mL), and the combined organic phases were washed with brine and evaporated to dryness. The crude product was purified with column chromatography (heptane to ethyl acetate) to yield 6-([1,1'-biphenyl]-4-ylmethyl)-8-methoxy-3-(tetrahydro-2H-pyran-4-yl)-[1,2,4]triazolo[4,3-a]pyrazine (232 mg, 0.579 mmol, 81%) as a solid. LC-MS: $t_R$=0.79 min (method 5), m/z=401.1 [M+H]$^+$.

Step 2:
6-([1,1'-biphenyl]-4-ylmethyl)-8-methoxy-3-(tetrahydro-2H-pyran-4-yl)-[1,2,4]triazolo[4,3-a]pyrazine (248 mg, 0.619 mmol) was mixed with HCl (2.333 ml, 4.67 mmol, 2 molar, H$_2$O) and MeOH (5544 mg, 7 ml, 173 mmol). The reaction was heated in microwave-oven at 100° C. for 20 min. The reaction was concentrated in vacuo. To give crude 6-([1,1'-biphenyl]-4-ylmethyl)-3-(tetrahydro-2H-pyran-4-yl)-[1,2,4]triazolo[4,3-a]pyrazin-8(7H)-one hydrochloride (233 mg, 0.540 mmol, 87% yield) which was used for next step without further purification.

Step 3:
6-([1,1'-biphenyl]-4-ylmethyl)-3-(tetrahydro-2H-pyran-4-yl)-[1,2,4]triazolo[4,3-a]pyrazin-8(7H)-one hydrochloride (233 mg, 0.540 mmol, 98%), (bromomethyl)cyclohexane (220 mg, 0.174 ml, 1.244 mmol), Sodium iodide (8.09 mg, 0.054 mmol) and K$_2$CO$_3$ (336 mg, 2.428 mmol) was dissolved in DMF (6608 mg, 7 ml, 90 mmol) and stirred at 60° C. overnight. The reaction was poured into water, and extracted with ethyl acetate (2 two times 10 ml), and concentrated. The crude product was purified by column chromatography (heptane to ethyl acetate) to give 6-([1,1'-biphenyl]-4-yl methyl)-7-(cyclohexylmethyl)-3-(tetrahydro-2H-pyran-4-yl)-[1,2,4]triazolo[4,3-a]pyrazin-8(7H)-one (80 mg, 0.164 mmol, 30%). $^1$H NMR (600 MHz, CDCl$_3$) δ 7.61-7.55 (m, 4H), 7.46 (t, J=7.7 Hz, 2H), 7.37 (s, 1H), 7.23 (d, J=8.3 Hz, 2H), 6.85 (s, 1H), 4.13-4.07 (m, 2H), 4.00 (s, 2H), 3.78 (bs, 2H), 3.55 (td, J=11.6, 2.2 Hz, 2H), 3.19 (m, 1H), 2.23-2.14 (m, 2H), 1.95 (m, 3H), 1.81-1.75 (m, 2H), 1.75-1.70 (m, 3H), 1.65 (d, J=12.0 Hz, 2H), 1.16 (d, J=8.3 Hz, 2H), 1.06 (s, 1H). LC-MS: $t_R$=0.89 min (method 5), m/z=483.3 [M+H]$^+$.

Example 79

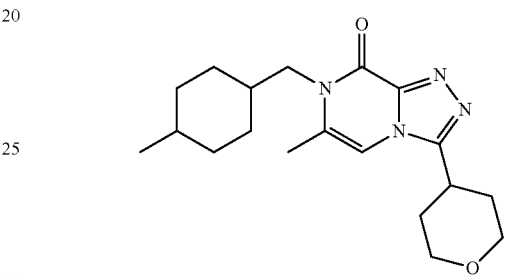

6-methyl-7-((4-methylcyclohexyl)methyl)-3-(tetrahydro-2H-pyran-4-yl)-[1,2,4]triazolo[4,3-a]pyrazin-8(7H)-one, stereoisomer 1 and 2

To a suspension of 3-(tetrahydro-2H-pyran-4-yl)-[1,2,4]triazolo[4,3-a]pyrazin-8(7H)-one (250 mg, 1.40 mmol) in DMF (5 mL) will be added (4-methylcyclohexyl)methyl methanesulfonate (376 mg, 1.82 mmol) and K$_2$CO$_3$ (388 mg, 2.81 mmol). The mixture will be heated at 60° C. for 12 h. The mixture will be concentrated and the residue will be dissolved in DCM (10 mL) and H$_2$O (10 mL). The organic layer will be dried over Na$_2$SO$_4$, filtered and concentrated to give the crude product. The crude product will be washed with MeOH (10 mL) to give 6-methyl-7-((4-methylcyclohexyl)methyl)-3-(tetrahydro-2H-pyran-4-yl)-[1,2,4]triazolo[4,3-a]pyrazin-8(7H)-one. The two stereoisomers will be separated by SFC.

Example 80

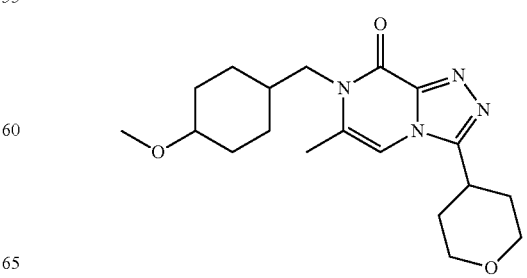

7-((4-methoxycyclohexyl)methyl)-6-methyl-3-(tetrahydro-2H-pyran-4-yl)-[1,2,4]triazolo[4,3-a]pyrazin-8(7H)-one, stereoisomer 1 and 2

To a suspension of 3-(tetrahydro-2H-pyran-4-yl)-[1,2,4]triazolo[4,3-a]pyrazin-8(7H)-one (250 mg, 1.40 mmol) in DMF (5 mL) will be added (4-methoxycyclohexyl)methyl methanesulfonate (376 mg, 1.82 mmol) and K₂CO₃ (388 mg, 2.81 mmol). The mixture will be heated at 60° C. for 12 h. The mixture will be concentrated and the residue will be dissolved in DCM (10 mL) and H₂O (10 mL). The organic layer will be dried over Na₂SO₄, filtered and concentrated to give the crude product. The crude product will be washed with MeOH (10 mL) to give 6-methyl-7-((4-methylcyclohexyl)methyl)-3-(tetrahydro-2H-pyran-4-yl)-[1,2,4]triazolo[4,3-a]pyrazin-8(7H)-one. The two stereoisomers will be separated by SFC.

Example 81

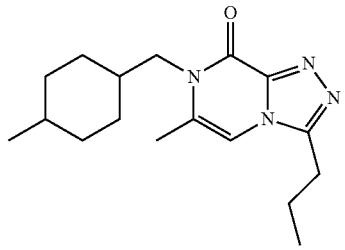 [SMILES: CCCc1nnc2c(=O)n(CC3CCC(C)CC3)c(C)cn12]

6-methyl-7-((4-methylcyclohexyl)methyl)-3-propyl-[1,2,4]triazolo[4,3-a]pyrazin-8(7H)-one, stereoisomer 1 and 2

To a suspension of 3-propyl-[1,2,4]triazolo[4,3-a]pyrazin-8(7H)-one (250 mg, 1.40 mmol) in DMF (5 mL) will be added (4-methylcyclohexyl)methyl methanesulfonate (376 mg, 1.82 mmol) and K₂CO₃ (388 mg, 2.81 mmol). The mixture will be heated at 60° C. for 12 h. The mixture will be concentrated and the residue will be dissolved in DCM (10 mL) and H₂O (10 mL). The organic layer will be dried over Na₂SO₄, filtered and concentrated to give the crude product. The crude product will be washed with MeOH (10 mL) to give 6-methyl-7-((4-methylcyclohexyl)methyl)-3-(tetrahydro-2H-pyran-4-yl)-[1,2,4]triazolo[4,3-a]pyrazin-8(7H)-one. The two stereoisomers will be separated by SFC.

Example 82

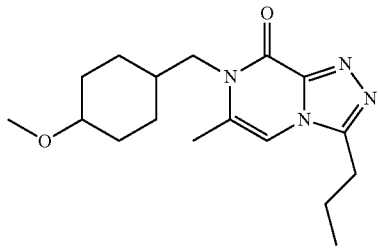 [SMILES: CCCc1nnc2c(=O)n(CC3CCC(OC)CC3)c(C)cn12]

7-((4-methoxycyclohexyl)methyl)-6-methyl-3-propyl-[1,2,4]triazolo[4,3-a]pyrazin-8(7H)-one, stereoisomer 1 and 2

To a suspension of 3-propyl-[1,2,4]triazolo[4,3-a]pyrazin-8(7H)-one (250 mg, 1.40 mmol) in DMF (5 mL) will be added (4-methoxycyclohexyl)methyl methanesulfonate (376 mg, 1.82 mmol) and K₂CO₃ (388 mg, 2.81 mmol). The mixture will be heated at 60° C. for 12 h. The mixture will be concentrated and the residue will be dissolved in DCM (10 mL) and H₂O (10 mL). The organic layer will be dried over Na₂SO₄, filtered and concentrated to give the crude product. The crude product will be washed with MeOH (10 mL) to give 6-methyl-7-((4-methylcyclohexyl)methyl)-3-(tetrahydro-2H-pyran-4-yl)-[1,2,4]triazolo[4,3-a]pyrazin-8(7H)-one. The two stereoisomers will be separated by SFC.

Example 83

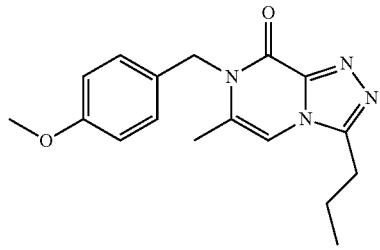 [SMILES: CCCc1nnc2c(=O)n(Cc3ccc(OC)cc3)c(C)cn12]

7-(4-methoxybenzyl)-6-methyl-3-propyl-[1,2,4]triazolo[4,3-a]pyrazin-8(7H)-one

Step 1:
To a solution of (4-methoxyphenyl)methanamine (30.00 g, 218.69 mmol) and Et₃N (26.56 g, 262.43 mmol) in dry DCM (500 mL) was added ethyl 2-chloro-2-oxoacetate (32.84 g, 240.56 mmol) dropwise at 0° C. The mixture was stirred at 0° C. for 40 min. The mixture was quenched with H₂O (15 mL), extracted with DCM (10 mL, three times). The combined organics were dried over Na₂SO₄ and concentrated. ethyl 2-((4-methoxybenzyl)amino)-2-oxoacetate (50.00 g, 96% yield) was obtained.

Step 2:
To a solution of ethyl 2-((4-methoxybenzyl)amino)-2-oxoacetate (10.00 g, 42.15 mmol) in EtOH (200 mL) was added 1-aminopropan-2-ol (3.80 g, 50.58 mmol). The mixture was heated at 75° C. for 2 hours. The mixture was concentrated under vacuum, washed with n-hexane (150 mL, two times), filtered and dried under vacuum. N1-(2-hydroxypropyl)-N2-(4-methoxybenzyl)oxalamide (8.70 g, 77% yield) was obtained.

Step 3:
To a solution of N1-(2-hydroxypropyl)-N2-(4-methoxybenzyl)oxalamide (5.00 g, 18.78 mmol) in CH₃CN (100 mL) was added trichlororuthenium hydrate (42.33 mg, 187.80 micromol) in H₂O (7.5 mL) and NaBrO₃ (3.12 g, 20.66 mmol) in water (15 mL). The mixture was stirred at 25° C. for 16 hours. Water (250 mL) was added to the mixture and stirred at 25° C. for 2 hours. The mixture was filtered, washed with H₂O (200 mL, three times) and dried under vacuum. N1-(4-methoxybenzyl)-N2-(2-oxopropyl) oxalamide (3.16 g, 43% yield, 67.67% purity) was obtained.

Step 4:

To a solution of N1-(4-methoxybenzyl)-N2-(2-oxopropyl)oxalamide (3.00 g, 11.35 mmol) in CH₃COOH (10 mL) was added TFA (1.29 g, 11.35 mmol). The mixture was stirred at 140° C. for 4 hours. The mixture was concentrated under vacuum. Brown solid was obtained. H₂O (2 mL) was added to the solid. The mixture was adjusted to pH=7 by saturated aq. NaHCO₃. The mixture was filtered. The filter cake was washed with water (30 mL, three times) and dried under vacuum. 1-(4-methoxybenzyl)-6-methyl-1,4-dihydropyrazine-2,3-dione (2.10 g, 75% yield) was obtained.

Step 5:

1-(4-methoxybenzyl)-6-methyl-1,4-dihydropyrazine-2,3-dione (4.50 g, 18.27 mmol) was added to POCl₃ (49.50 g, 322.83 mmol). The mixture was stirred at 26° C. for 16 hr. The mixture was concentrated and the residue was poured into water (50 mL). The mixture was adjusted to pH=7 by sat. aq. NaHCO₃ and extracted with DCM (200 mL, two times). The combined organic layer was washed with H₂O (200 mL), dried over Na₂SO₄, filtered and concentrated. The crude product was purified by flash chromatography on silica gel (5%-50% ethyl acetate in petroleumsether). 3-chloro-1-(4-methoxybenzyl)-6-methylpyrazin-2(1H)-one (3.78 g, 78% yield) was obtained.

Step 6:

To a solution of 3-chloro-1-(4-methoxybenzyl)-6-methylpyrazin-2(1H)-one (970.00 mg, 3.66 mmol) in EtOH (15 mL) was added NH₂NH₂.H₂O (1.83 g, 36.60 mmol). The mixture was stirred at 40° C. for 16 hours. The mixture was filtered. The filter cake was washed with cold EtOH (10 mL, three times) and dried under vacuum. 3-hydrazinyl-1-(4-methoxybenzyl)-6-methylpyrazin-2(1H)-one (760 mg, 79% yield) was obtained.

Step 7:

To a solution of 3-hydrazinyl-1-(4-methoxybenzyl)-6-methylpyrazin-2(1H)-one (100 mg, 384.19 micromol) in dry DCM (5 mL) was added butanal (29 mg, 403.40 micromol). The mixture was stirred at 40° C. for 2 hours. The reaction mixture was cooled to 25° C. and directly used for the next step.

Step 8:

To the solution of crude (E)-3-(2-butylidenehydrazinyl)-1-(4-methoxybenzyl)-6-methylpyrazin-2(1H)-one obtained above was added PhI(OAc)₂ (142 mg, 441.81 micromol). The mixture was stirred at 25° C. for 2 hours. Sat. aq. NaHCO₃ (2 mL) and H₂O (5 mL) was added to the mixture. The mixture was extracted with DCM (10 mL, three times). The combined organic was concentrated under vacuum. The residue was purified by CombiFlash (silica gel, 100% ethyl acetate). 7-(4-methoxybenzyl)-6-methyl-3-propyl-[1,2,4]triazolo[4,3-a]pyrazin-8(7H)-one (47 mg, 38% yield, 97% purity) was obtained. ¹H NMR (CDCl₃ 400 MHz): δ 7.18 (d, J=8.4 Hz, 2H), 6.85 (d, J=8.0 Hz, 2H), 6.72 (s, 1H), 5.25 (s, 2H), 3.78 (s, 3H), 2.93 (t, J=7.6 Hz, 2H), 2.27 (s, 3H), 1.92-1.87 (m, 2H), 1.05 (t, J=7.6 Hz, 3H). LC-MS: $t_R$=1.844 min (method 6), m/z=313.1 [M+H]⁺.

Example 84

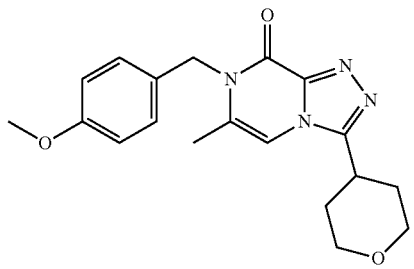 [SMILES: COc1ccc(Cn2c(C)cn3c(C4CCOCC4)nnc3c2=O)cc1]

7-(4-methoxybenzyl)-6-methyl-3-(tetrahydro-2H-pyran-4-yl)-[1,2,4]triazolo[4,3-a]pyrazin-8(7H)-one Step 1:

To a solution of 3-hydrazinyl-1-(4-methoxybenzyl)-6-methylpyrazin-2(1H)-one (600 mg, 2.31 mmol) in DCM (20 mL) was added tetrahydro-2H-pyran-4-carbaldehyde (276 mg, 2.43 mmol). The mixture was stirred at 40° C. for 1.5 hours. The mixture was directly used to the next step.

Step 2:

To the reaction mixture obtained above was added PhI(OAc)₂ (71 mg, 220 micromol). The mixture was stirred at 25° C. for 2 hours. H₂O (5 mL) was added to the mixture. The mixture was extracted with DCM (10 mL, three times). The combined organic phases were concentrated under vacuum. The residue was purified by CombiFlash (silica gel, 10% MeOH in DCM). 7-(4-methoxybenzyl)-6-methyl-3-(tetrahydro-2H-pyran-4-yl)-[1,2,4]triazolo[4,3-a]pyrazin-8(7H)-one (17.00 mg, 24.69% yield, 98.87% purity) was obtained. ¹H NMR (CDCl₃ 400 MHz): δ7.17 (d, J=8.4 Hz, 2H), 6.84 (d, J=8.8 Hz, 2H), 6.77 (s, 1H), 5.24 (s, 2H), 4.13 (d, J=11.6 Hz, 2H), 3.78 (s, 3H), 3.61-3.55 (m, 2H), 2.21-3.16 (m, 1H), 2.27 (s, 3H), 2.20-2.14 (m, 2H), 1.96-1.93 (m, 2H). LC-MS: $t_R$=1.984 min (method 3), m/z=355.1 [M+H]⁺.

PDE1 Inhibition Assay

PDE1A, PDE1B and PDE1C assays were performed as follows: the assays were performed in 60 μL samples containing a fixed amount of the PDE1 enzym1 (sufficient to convert 20-25% of the cyclic nucleotide substrate), a buffer (50 mM HEPES pH 7.6; 10 mM MgCl₂; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 h at room temperature before being terminated through mixing with 20 μL (0.2 mg) yttrium silicate SPA beads (PerkinElmer). The beads were allowed to settle for 1 h in the dark before the plates were counted in a Wallac 1450 Microbeta counter. The measured signals were converted to activity relative to an uninhibited control (100%) and IC₅₀ values were calculated using XlFit (model 205, IDBS).

The invention claimed is:

1. A compound:
   (A) selected from the group consisting of:
   3-Propyl-7-((tetrahydro-2H-pyran-3-yl)methyl)-[1,2,4]triazolo[4,3-a]pyrazin-8(7H)-one, stereoisomer 1;
   3-Propyl-7-((tetrahydro-2H-pyran-3-yl)methyl)-[1,2,4]triazolo[4,3-a]pyrazin-8(7H)-one, stereoisomer 2;
   7-(Cyclohexylmethyl)-3-propyl-[1,2,4]triazolo[4,3-a]pyrazin-8(7H)-one;

7-(Cyclopentylmethyl)-3-propyl-[1,2,4]triazolo[4,3-a]pyrazin-8(7H)-one;
3-Propyl-7-((tetrahydro-2H-pyran-4-yl)methyl)-[1,2,4]triazolo[4,3-a]pyrazin-8(7H)-one;
7-Isobutyl-3-propyl-[1,2,4]triazolo[4,3-a]pyrazin-8(7H)-one;
7-(Cyclopropylmethyl)-3-propyl-[1,2,4]triazolo[4,3-a]pyrazin-8(7H)-one;
7-Ethyl-3-propyl-[1,2,4]triazolo[4,3-a]pyrazin-8(7H)-one;
7-(Oxetan-3-ylmethyl)-3-propyl-[1,2,4]triazolo[4,3-a]pyrazin-8(7H)-one;
7-(Cycloheptylmethyl)-3-propyl-[1,2,4]triazolo[4,3-a]pyrazin-8(7H)-one;
3-Propyl-7-((tetrahydrofuran-3-yl)methyl)-[1,2,4]triazolo[4,3-a]pyrazin-8(7H)-one, stereoisomer 1;
3-Propyl-7-((tetrahydrofuran-3-yl)methyl)-[1,2,4]triazolo[4,3-a]pyrazin-8(7H)-one, stereoisomer 2;
7-Benzyl-3-propyl-[1,2,4]triazolo[4,3-a]pyrazin-8(7H)-one;
7-(2-Fluorobenzyl)-3-propyl-[1,2,4]triazolo[4,3-a]pyrazin-8(7H)-one;
7-(3-Fluorobenzyl)-3-(tetrahydro-2H-pyran-4-yl)-[1,2,4]triazolo[4,3-a]pyrazin-8(7H)-one;
7-(3-Fluorobenzyl)-3-propyl-[1,2,4]triazolo[4,3-a]pyrazin-8(7H)-one;
7-(3-Methylbenzyl)-3-propyl-[1,2,4]triazolo[4,3-a]pyrazin-8(7H)-one;
3-Propyl-7-(4-(trifluoromethyl)benzyl)-[1,2,4]triazolo[4,3-a]pyrazin-8(7H)-one;
7-(3-Fluorobenzyl)-3-((tetrahydrofuran-3-yl)methyl)-[1,2,4]triazolo[4,3-a]pyrazin-8(7H)-one;
3-Propyl-7-(2-(trifluoromethyl)benzyl)-[1,2,4]triazolo[4,3-a]pyrazin-8(7H)-one;
7-(2-Chlorobenzyl)-3-propyl-[1,2,4]triazolo[4,3-a]pyrazin-8(7H)-one;
7-(4-Chlorobenzyl)-3-propyl-[1,2,4]triazolo[4,3-a]pyrazin-8(7H)-one;
7-(4-Chlorobenzyl)-3-(tetrahydrofuran-3-yl)-[1,2,4]triazolo[4,3-a]pyrazin-8(7H)-one;
7-Hexyl-3-(tetrahydro-2H-pyran-4-yl)-[1,2,4]triazolo[4,3-a]pyrazin-8(7H)-one;
7-(4-Fluorobenzyl)-3-propyl-[1,2,4]triazolo[4,3-a]pyrazin-8(7H)-one;
7-(4-Chlorobenzyl)-3-ethyl-[1,2,4]triazolo[4,3-a]pyrazin-8(7H)-one;
7-(3-Chlorobenzyl)-3-propyl-[1,2,4]triazolo[4,3-a]pyrazin-8(7H)-one;
7-(4-Methylbenzyl)-3-propyl-[1,2,4]triazolo[4,3-a]pyrazin-8(7H)-one;
7-(2-Methylbenzyl)-3-propyl-[1,2,4]triazolo[4,3-a]pyrazin-8(7H)-one;
3-Cyclopentyl-7-(3-fluorobenzyl)-[1,2,4]triazolo[4,3-a]pyrazin-8(7H)-one;
7-Isopentyl-3-(tetrahydro-2H-pyran-4-yl)-[1,2,4]triazolo[4,3-a]pyrazin-8(7H)-one;
3-Cyclopropyl-7-(3-fluorobenzyl)-[1,2,4]triazolo[4,3-a]pyrazin-8(7H)-one;
3-Cyclohexyl-7-(3-fluorobenzyl)-[1,2,4]triazolo[4,3-a]pyrazin-8(7H)-one;
7-(3-Fluorobenzyl)-3-(tetrahydro-2H-pyran-2-yl)-[1,2,4]triazolo[4,3-a]pyrazin-8(7H)-one, stereoisomer 1;
7-(3-Fluorobenzyl)-3-(tetrahydro-2H-pyran-2-yl)-[1,2,4]triazolo[4,3-a]pyrazin-8(7H)-one, stereoisomer 2;
7-(3-Fluorobenzyl)-3-(tetrahydrofuran-3-yl)-[1,2,4]triazolo[4,3-a]pyrazin-8(7H)-one, stereoisomer 1;
7-(3-Fluorobenzyl)-3-(tetrahydrofuran-3-yl)-[1,2,4]triazolo[4,3-a]pyrazin-8(7H)-one, stereoisomer 2;
7-(3-Fluorobenzyl)-3-(2-fluoroethyl)-[1,2,4]triazolo[4,3-a]pyrazin-8(7H)-one;
3-(1,1-Difluoroethyl)-7-(3-fluorobenzyl)-[1,2,4]triazolo[4,3-a]pyrazin-8(7H)-one;
7-(3-Fluorobenzyl)-3-(tetrahydro-2H-pyran-3-yl)-[1,2,4]triazolo[4,3-a]pyrazin-8(7H)-one, stereoisomer 1;
7-(3-Fluorobenzyl)-3-(tetrahydro-2H-pyran-3-yl)-[1,2,4]triazolo[4,3-a]pyrazin-8(7H)-one, stereoisomer 2;
7-(3-Fluorobenzyl)-3-(tetrahydrofuran-2-yl)-[1,2,4]triazolo[4,3-a]pyrazin-8(7H)-one, Stereoisomer 1;
7-(3-Fluorobenzyl)-3-(tetrahydrofuran-2-yl)-[1,2,4]triazolo[4,3-a]pyrazin-8(7H)-one, Stereoisomer 2;
7-(3-Fluorobenzyl)-3-((tetrahydrofuran-2-yl)methyl)-[1,2,4]triazolo[4,3-a]pyrazin-8(7H)-one, stereoisomer 1;
7-(3-Fluorobenzyl)-3-((tetrahydrofuran-2-yl)methyl)-[1,2,4]triazolo[4,3-a]pyrazin-8(7H)-one, stereoisomer 2;
7-(3-Fluorobenzyl)-3-(2,2,2-trifluoroethyl)-[1,2,4]triazolo[4,3-a]pyrazin-8(7H)-one;
7-(3-Fluorobenzyl)-3-(oxetan-3-yl)-[1,2,4]triazolo[4,3-a]pyrazin-8(7H)-one;
7-(3-Fluorobenzyl)-3-(1-fluoroethyl)-[1,2,4]triazolo[4,3-a]pyrazin-8(7H)-one, stereoisomer 2;
7-(3-Fluorobenzyl)-3-(1-fluoroethyl)-[1,2,4]triazolo[4,3-a]pyrazin-8(7H)-one, stereoisomer 1;
7-(3-Fluorobenzyl)-3-(heptan-3-yl)-[1,2,4]triazolo[4,3-a]pyrazin-8(7H)-one;
7-(3-Fluorobenzyl)-3-((tetrahydrofuran-3-yl)methyl)-[1,2,4]triazolo[4,3-a]pyrazin-8(7H)-one, stereoisomer 1;
7-(3-Fluorobenzyl)-3-((tetrahydrofuran-3-yl)methyl)-[1,2,4]triazolo[4,3-a]pyrazin-8(7H)-one, stereoisomer 2;
7-((4,4-Dimethylcyclohexyl)methyl)-3-propyl-[1,2,4]triazolo[4,3-a]pyrazin-8(7H)-one;
7-(Cycloheptylmethyl)-3-(tetrahydro-2H-pyran-4-yl)-[1,2,4]triazolo[4,3-a]pyrazin-8(7H)-one;
7-(((3r,5r,7r)-Adamantan-1-yl)methyl)-3-propyl-[1,2,4]triazolo[4,3-a]pyrazin-8(7H)-one;
7-((4-Methylcyclohexyl)methyl)-3-propyl-[1,2,4]triazolo[4,3-a]pyrazin-8(7H)-one;
7-((1-Methylcyclohexyl)methyl)-3-propyl-[1,2,4]triazolo[4,3-a]pyrazin-8(7H)-one;
7-((4,4-Difluorocyclohexyl)methyl)-3-propyl-[1,2,4]triazolo[4,3-a]pyrazin-8(7H)-one;
7-(Cyclopentylmethyl)-3-(tetrahydro-2H-pyran-4-yl)-[1,2,4]triazolo[4,3-a]pyrazin-8(7H)-one;
7-(Cyclohexylmethyl)-3-(tetrahydro-2H-pyran-4-yl)-[1,2,4]triazolo[4,3-a]pyrazin-8(7H)-one;
3-Propyl-7-(spiro[2.5]octan-6-ylmethyl)-[1,2,4]triazolo[4,3-a]pyrazin-8(7H)-one;
7-((3-Methylcyclohexyl)methyl)-3-propyl-[1,2,4]triazolo[4,3-a]pyrazin-8(7H)-one;
7-((2-Methylcyclohexyl)methyl)-3-propyl-[1,2,4]triazolo[4,3-a]pyrazin-8(7H)-one;
7-(((1r,3r,5r,7r)-Adamantan-2-yl)methyl)-3-propyl-[1,2,4]triazolo[4,3-a]pyrazin-8(7H)-one;
7-((4-Fluorocyclohexyl)methyl)-3-propyl-[1,2,4]triazolo[4,3-a]pyrazin-8(7H)-one;
7-(3-Fluorobenzyl)-3-((1s,4s)-4-hydroxycyclohexyl)-[1,2,4]triazolo[4,3-a]pyrazin-8(7H)-one;
7-(3-Fluorobenzyl)-3-((1r,4s)-4-hydroxycyclohexyl)-[1,2,4]triazolo[4,3-a]pyrazin-8(7H)-one;

7-(((1s,4s)-4-methylcyclohexyl)methyl)-3-propyl-[1,2,4]triazolo[4,3-a]pyrazin-8(7H)-one;

7-(((1r,4r)-4-methylcyclohexyl)methyl)-3-propyl-[1,2,4]triazolo[4,3-a]pyrazin-8(7H)-one;

6-bromo-7-(3-fluorobenzyl)-3-propyl-[1,2,4]triazolo[4,3-a]pyrazin-8(7H)-one;

6-bromo-7-(3-fluorobenzyl)-3-(tetrahydro-2H-pyran-4-yl)-[1,2,4]triazolo[4,3-a]pyrazin-8(7H)-one;

6-bromo-7-(cyclopentylmethyl)-3-(tetrahydro-2H-pyran-4-yl)-[1,2,4]triazolo[4,3-a]pyrazin-8(7H)-one;

6-bromo-7-(cyclohexylmethyl)-3-(tetrahydro-2H-pyran-4-yl)-[1,2,4]triazolo[4,3-a]pyrazin-8(7H)-one;

6-bromo-7-(cycloheptylmethyl)-3-(tetrahydro-2H-pyran-4-yl)-[1,2,4]triazolo[4,3-a]pyrazin-8(7H)-one;

6-benzyl-7-methyl-3-(tetrahydro-2H-pyran-4-yl)-[1,2,4]triazolo[4,3-a]pyrazin-8(7H)-one;

7-(4-methoxybenzyl)-6-methyl-3-(tetrahydro-2H-pyran-4-yl)-[1,2,4]triazolo[4,3-a]pyrazin-8(7H)-one;

7-(4-methoxybenzyl)-6-methyl-3-propyl-[1,2,4]triazolo[4,3-a]pyrazin-8(7H)-one;

7-((4-methoxycyclohexyl)methyl)-6-methyl-3-propyl-[1,2,4]triazolo[4,3-a]pyrazin-8(7H)-one (cis);

7-((4-methoxycyclohexyl)methyl)-6-methyl-3-propyl-[1,2,4]triazolo[4,3-a]pyrazin-8(7H)-one (trans);

Cis 6-methyl-7-((4-methylcyclohexyl)methyl)-3-propyl-[1,2,4]triazolo[4,3-a]pyrazin-8(7H)-one;

Trans 6-methyl-7-((4-methylcyclohexyl)methyl)-3-propyl-[1,2,4]triazolo[4,3-a]pyrazin-8(7H)-one;

Cis-7-((4-methoxycyclohexyl)methyl)-6-methyl-3-(tetrahydro-2H-pyran-4-yl)-[1,2,4]triazolo[4,3-a]pyrazin-8(7H)-one;

Trans-7-((4-methoxycyclohexyl)methyl)-6-methyl-3-(tetrahydro-2H-pyran-4-yl)-[1,2,4]triazolo[4,3-a]pyrazin-8(7H)-one;

Cis-6-methyl-7-((4-methylcyclohexyl)methyl)-3-(tetrahydro-2H-pyran-4-yl)-[1,2,4]triazolo[4,3-a]pyrazin-8(7H)-one;

Trans-6-methyl-7-((4-methylcyclohexyl)methyl)-3-(tetrahydro-2H-pyran-4-yl)-[1,2,4]triazolo[4,3-a]pyrazin-8(7H)-one;

6-([1,1'-biphenyl]-4-ylmethyl)-7-(cyclohexylmethyl)-3-(tetrahydro-2H-pyran-4-yl)-[1,2,4]triazolo[4,3-a]pyrazin-8(7H)-one;

7-(3-fluorobenzyl)-6-(3-methylbenzyl)-3-(tetrahydro-2H-pyran-4-yl)-[1,2,4]triazolo[4,3-a]pyrazin-8(7H)-one;

7-(cyclohexylmethyl)-6-(3-methylbenzyl)-3-(tetrahydro-2H-pyran-4-yl)-[1,2,4]triazolo[4,3-a]pyrazin-8(7H)-one;

7-(cyclopentylmethyl)-6-(3-methylbenzyl)-3-(tetrahydro-2H-pyran-4-yl)-[1,2,4]triazolo[4,3-a]pyrazin-8(7H)-one;

7-(cycloheptylmethyl)-6-(4-fluorobenzyl)-3-(tetrahydro-2H-pyran-4-yl)-[1,2,4]triazolo[4,3-a]pyrazin-8(7H)-one;

6-benzyl-7-(cycloheptylmethyl)-3-(tetrahydro-2H-pyran-4-yl)-[1,2,4]triazolo[4,3-a]pyrazin-8(7H)-one;

6,7-bis(3-fluorobenzyl)-3-(tetrahydro-2H-pyran-4-yl)-[1,2,4]triazolo[4,3-a]pyrazin-8(7H)-one;

7-(cyclohexylmethyl)-6-(3-fluorobenzyl)-3-(tetrahydro-2H-pyran-4-yl)-[1,2,4]triazolo[4,3-a]pyrazin-8(7H)-one;

7-(cyclopentylmethyl)-6-(3-fluorobenzyl)-3-(tetrahydro-2H-pyran-4-yl)-[1,2,4]triazolo[4,3-a]pyrazin-8(7H)-one;

7-(3-fluorobenzyl)-6-(4-fluorobenzyl)-3-(tetrahydro-2H-pyran-4-yl)-[1,2,4]triazolo[4,3-a]pyrazin-8(7H)-one;

7-(cyclohexylmethyl)-6-(4-fluorobenzyl)-3-(tetrahydro-2H-pyran-4-yl)-[1,2,4]triazolo[4,3-a]pyrazin-8(7H)-one;

7-(cyclopentylmethyl)-6-(4-fluorobenzyl)-3-(tetrahydro-2H-pyran-4-yl)-[1,2,4]triazolo[4,3-a]pyrazin-8(7H)-one;

7-(cycloheptylmethyl)-6-(2-methylbenzyl)-3-(tetrahydro-2H-pyran-4-yl)-[1,2,4]triazolo[4,3-a]pyrazin-8(7H)-one;

7-(cycloheptylmethyl)-6-(4-methylbenzyl)-3-(tetrahydro-2H-pyran-4-yl)-[1,2,4]triazolo[4,3-a]pyrazin-8(7H)-one;

7-(cyclohexylmethyl)-6-(4-methylbenzyl)-3-(tetrahydro-2H-pyran-4-yl)-[1,2,4]triazolo[4,3-a]pyrazin-8(7H)-one;

7-(cyclopentylmethyl)-6-(4-methylbenzyl)-3-(tetrahydro-2H-pyran-4-yl)-[1,2,4]triazolo[4,3-a]pyrazin-8(7H)-one;

7-(cyclohexylmethyl)-6-(2-methylbenzyl)-3-(tetrahydro-2H-pyran-4-yl)-[1,2,4]triazolo[4,3-a]pyrazin-8(7H)-one;

7-(cyclopentylmethyl)-6-(2-methylbenzyl)-3-(tetrahydro-2H-pyran-4-yl)-[1,2,4]triazolo[4,3-a]pyrazin-8(7H)-one;

6-benzyl-7-(cyclopentylmethyl)-3-(tetrahydro-2H-pyran-4-yl)-[1,2,4]triazolo[4,3-a]pyrazin-8(7H)-one;

6-benzyl-7-(cyclohexylmethyl)-3-(tetrahydro-2H-pyran-4-yl)-[1,2,4]triazolo[4,3-a]pyrazin-8(7H)-one;

7-(3-fluorobenzyl)-6-(4-methylbenzyl)-3-(tetrahydro-2H-pyran-4-yl)-[1,2,4]triazolo[4,3-a]pyrazin-8(7H)-one;

7-(3-fluorobenzyl)-6-(2-methylbenzyl)-3-(tetrahydro-2H-pyran-4-yl)-[1,2,4]triazolo[4,3-a]pyrazin-8(7H)-one;

6-benzyl-7-(4-fluorobenzyl)-3-(tetrahydro-2H-pyran-4-yl)-[1,2,4]triazolo[4,3-a]pyrazin-8(7H)-one;

(R)-7-(3-fluorobenzyl)-3-propyl-6-(tetrahydrofuran-3-yl)-[1,2,4]triazolo[4,3-a]pyrazin-8(7H)-one;

(S)-7-(3-fluorobenzyl)-3-propyl-6-(tetrahydrofuran-3-yl)-[1,2,4]triazolo[4,3-a]pyrazin-8(7H)-one;

7-(3-fluorobenzyl)-6-methyl-3-propyl-[1,2,4]triazolo[4,3-a]pyrazin-8(7H)-one;

7-(3-fluorobenzyl)-6-ethyl-3-propyl-[1,2,4]triazolo[4,3-a]pyrazin-8(7H)-one;

6-benzyl-7-(3-fluorobenzyl)-3-(tetrahydro-2H-pyran-4-yl)-[1,2,4]triazolo[4,3-a]pyrazin-8(7H)-one;

(R)-7-(3-fluorobenzyl)-3-propyl-5-(tetrahydrofuran-3-yl)-[1,2,4]triazolo[4,3-a]pyrazin-8(7H)-one;

(S)-7-(3-fluorobenzyl)-3-propyl-5-(tetrahydrofuran-3-yl)-[1,2,4]triazolo[4,3-a]pyrazin-8(7H)-one;

7-(3-fluorobenzyl)-3-propyl-5-methyl-[1,2,4]triazolo[4,3-a]pyrazin-8(7H)-one;

7-(3-fluorobenzyl)-3-propyl-5-ethyl-[1,2,4]triazolo[4,3-a]pyrazin-8(7H)-one; and 5-bromo-7-(3-fluorobenzyl)-3-propyl-[1,2,4]triazolo[4,3-a]pyrazin-8(7H)-one;

and (B) pharmaceutically acceptable salts thereof.

2. A pharmaceutical composition comprising a therapeutically effective amount of the compound of claim 1, or a pharmaceutically acceptable salt thereof, and one or more pharmaceutically acceptable carriers, diluents and/or excipients.

3. The pharmaceutical composition of claim 2, wherein said composition comprises:

(A) the compound:

7-(Cycloheptylmethyl)-3-(tetrahydro-2H-pyran-4-yl)-[1,2,4]triazolo[4,3-a]pyrazin-8(7H)-one;
7-((4-Methylcyclohexyl)methyl)-3-propyl-[1,2,4]triazolo[4,3-a]pyrazin-8(7H)-one;
3-Propyl-7-(spiro[2.5]octan-6-ylmethyl)-[1,2,4]triazolo[4,3-a]pyrazin-8(7H)-one;
7-((3-Methylcyclohexyl)methyl)-3-propyl-[1,2,4]triazolo[4,3-a]pyrazin-8(7H)-one;
7-(((1s,4s)-4-methylcyclohexyl)methyl)-3-propyl-[1,2,4]triazolo[4,3-a]pyrazin-8(7H)-one;
7-(((1r,4r)-4-methylcyclohexyl)methyl)-3-propyl-[1,2,4]triazolo[4,3-a]pyrazin-8(7H)-one;
6-bromo-7-(3-fluorobenzyl)-3-propyl-[1,2,4]triazolo[4,3-a]pyrazin-8(7H)-one;
6-bromo-7-(3-fluorobenzyl)-3-(tetrahydro-2H-pyran-4-yl)-[1,2,4]triazolo[4,3-a]pyrazin-8(7H)-one;
6-bromo-7-(cyclopentylmethyl)-3-(tetrahydro-2H-pyran-4-yl)-[1,2,4]triazolo[4,3-a]pyrazin-8(7H)-one;
6-bromo-7-(cyclohexylmethyl)-3-(tetrahydro-2H-pyran-4-yl)-[1,2,4]triazolo[4,3-a]pyrazin-8(7H)-one;
6-bromo-7-(cycloheptylmethyl)-3-(tetrahydro-2H-pyran-4-yl)-[1,2,4]triazolo[4,3-a]pyrazin-8(7H)-one;
7-(4-methoxybenzyl)-6-methyl-3-(tetrahydro-2H-pyran-4-yl)-[1,2,4]triazolo[4,3-a]pyrazin-8(7H)-one;
7-(4-methoxybenzyl)-6-methyl-3-propyl-[1,2,4]triazolo[4,3-a]pyrazin-8(7H)-one;
6-([1,1'-biphenyl]-4-ylmethyl)-7-(cyclohexylmethyl)-3-(tetrahydro-2H-pyran-4-yl)-[1,2,4]triazolo[4,3-a]pyrazin-8(7H)-one;
7-(cyclohexylmethyl)-6-(3-methylbenzyl)-3-(tetrahydro-2H-pyran-4-yl)-[1,2,4]triazolo[4,3-a]pyrazin-8(7H)-one;
7-(cyclopentylmethyl)-6-(3-methylbenzyl)-3-(tetrahydro-2H-pyran-4-yl)-[1,2,4]triazolo[4,3-a]pyrazin-8(7H)-one;
7-(cycloheptylmethyl)-6-(4-fluorobenzyl)-3-(tetrahydro-2H-pyran-4-yl)-[1,2,4]triazolo[4,3-a]pyrazin-8(7H)-one;
6-benzyl-7-(cycloheptylmethyl)-3-(tetrahydro-2H-pyran-4-yl)-[1,2,4]triazolo[4,3-a]pyrazin-8(7H)-one;
6,7-bis(3-fluorobenzyl)-3-(tetrahydro-2H-pyran-4-yl)-[1,2,4]triazolo[4,3-a]pyrazin-8(7H)-one;
7-(cyclohexylmethyl)-6-(3-fluorobenzyl)-3-(tetrahydro-2H-pyran-4-yl)-[1,2,4]triazolo[4,3-a]pyrazin-8(7H)-one;
7-(cyclopentylmethyl)-6-(3-fluorobenzyl)-3-(tetrahydro-2H-pyran-4-yl)-[1,2,4]triazolo[4,3-a]pyrazin-8(7H)-one;
7-(3-fluorobenzyl)-6-(4-fluorobenzyl)-3-(tetrahydro-2H-pyran-4-yl)-[1,2,4]triazolo[4,3-a]pyrazin-8(7H)-one;
7-(cyclohexylmethyl)-6-(4-fluorobenzyl)-3-(tetrahydro-2H-pyran-4-yl)-[1,2,4]triazolo[4,3-a]pyrazin-8(7H)-one;
7-(cyclopentylmethyl)-6-(4-fluorobenzyl)-3-(tetrahydro-2H-pyran-4-yl)-[1,2,4]triazolo[4,3-a]pyrazin-8(7H)-one;
7-(cycloheptylmethyl)-6-(2-methylbenzyl)-3-(tetrahydro-2H-pyran-4-yl)-[1,2,4]triazolo[4,3-a]pyrazin-8(7H)-one;
7-(cycloheptylmethyl)-6-(4-methylbenzyl)-3-(tetrahydro-2H-pyran-4-yl)-[1,2,4]triazolo[4,3-a]pyrazin-8(7H)-one;
7-(cyclohexylmethyl)-6-(4-methylbenzyl)-3-(tetrahydro-2H-pyran-4-yl)-[1,2,4]triazolo[4,3-a]pyrazin-8(7H)-one;
7-(cyclopentylmethyl)-6-(4-methylbenzyl)-3-(tetrahydro-2H-pyran-4-yl)-[1,2,4]triazolo[4,3-a]pyrazin-8(7H)-one;
7-(cyclohexylmethyl)-6-(2-methylbenzyl)-3-(tetrahydro-2H-pyran-4-yl)-[1,2,4]triazolo[4,3-a]pyrazin-8(7H)-one;
7-(cyclopentylmethyl)-6-(2-methylbenzyl)-3-(tetrahydro-2H-pyran-4-yl)-[1,2,4]triazolo[4,3-a]pyrazin-8(7H)-one;
6-benzyl-7-(cyclopentylmethyl)-3-(tetrahydro-2H-pyran-4-yl)-[1,2,4]triazolo[4,3-a]pyrazin-8(7H)-one;
6-benzyl-7-(cyclohexylmethyl)-3-(tetrahydro-2H-pyran-4-yl)-[1,2,4]triazolo[4,3-a]pyrazin-8(7H)-one;
7-(3-fluorobenzyl)-6-(4-methylbenzyl)-3-(tetrahydro-2H-pyran-4-yl)-[1,2,4]triazolo[4,3-a]pyrazin-8(7H)-one;
7-(3-fluorobenzyl)-6-(2-methylbenzyl)-3-(tetrahydro-2H-pyran-4-yl)-[1,2,4]triazolo[4,3-a]pyrazin-8(7H)-one;
6-benzyl-7-(4-fluorobenzyl)-3-(tetrahydro-2H-pyran-4-yl)-[1,2,4]triazolo[4,3-a]pyrazin-8(7H)-one;
or
6-benzyl-7-(3-fluorobenzyl)-3-(tetrahydro-2H-pyran-4-yl)-[1,2,4]triazolo[4,3-a]pyrazin-8(7H)-one;
or
(B) a pharmaceutically acceptable salt thereof.

4. A method of treating a neurodegenerative disease, comprising administering the pharmaceutical composition of claim 2 to a patient in need thereof, wherein said neurodegenerative disease is Alzheimer's Disease, Parkinson's Disease, Huntington's Disease.

5. A method of treating a neurodegenerative disease, comprising administering the pharmaceutical composition of claim 3 to a patient in need thereof, wherein said neurodegenerative disease is Alzheimer's Disease, Parkinson's Disease, Huntington's Disease.

6. A method of treating a psychiatric disorder, comprising administering the pharmaceutical composition of claim 2 to a patient in need thereof, wherein said psychiatric disorder is attention-deficit/hyperactivity disorder (ADHD), depression, narcolepsy, schizophrenia, cognitive impairment, or restless leg syndrome.

7. A method of treating a psychiatric disorder, comprising administering the pharmaceutical composition of claim 3 to a patient in need thereof, wherein said psychiatric disorder is attention-deficit/hyperactivity disorder (ADHD), depression, narcolepsy, schizophrenia, cognitive impairment, or restless leg syndrome.

8. The method of claim 7, wherein said method treats cognitive impairment associated with schizophrenia (CIAS).

* * * * *

UNITED STATES PATENT AND TRADEMARK OFFICE
CERTIFICATE OF CORRECTION

PATENT NO. : 10,150,771 B2
APPLICATION NO. : 15/517348
DATED : December 11, 2018
INVENTOR(S) : Jan Kehler et al.

It is certified that error appears in the above-identified patent and that said Letters Patent is hereby corrected as shown below:

In the Claims

Column 88, Line 64, replace ((1 s,4s) with ((1s,4s)

Column 88, Line 66, replace ((1r,4s) with ((1r,4r)

Column 89, Line 1, replace (((1 s,4s) with (((1s,4s)

Signed and Sealed this
Nineteenth Day of March, 2019

Andrei Iancu
*Director of the United States Patent and Trademark Office*